United States Patent
Heckel et al.

(10) Patent No.: US 8,759,349 B2
(45) Date of Patent: Jun. 24, 2014

(54) HETEROCYCLIC COMPOUNDS, MEDICAMENTS CONTAINING SAID COMPOUNDS, USE THEREOF AND PROCESSES FOR THE PREPARATION THEREOF

(71) Applicants: Armin Heckel, Biberach an der Riss (DE); Sara Frattini, Castelleone (IT); Dieter Hamprecht, Pozzolengo (IT); Joerg Kley, Mittelbiberach (DE)

(72) Inventors: Armin Heckel, Biberach an der Riss (DE); Sara Frattini, Castelleone (IT); Dieter Hamprecht, Pozzolengo (IT); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 4 days.

(21) Appl. No.: 13/662,791

(22) Filed: Oct. 29, 2012

(65) Prior Publication Data
US 2013/0109697 A1 May 2, 2013

(30) Foreign Application Priority Data
Nov. 2, 2011 (EP) .................... 11187553

(51) Int. Cl.
*A61K 31/497* (2006.01)
(52) U.S. Cl.
USPC .................... 514/252.11; 544/407
(58) Field of Classification Search
CPC .................................... A61K 31/497
USPC ...................................... 544/407
See application file for complete search history.

(56) References Cited

FOREIGN PATENT DOCUMENTS

| GB | 1214408 A | 12/1970 |
|---|---|---|
| GB | 1214409 A | 12/1970 |
| WO | 2008135557 A1 | 11/2008 |
| WO | 2009138378 A1 | 11/2009 |

OTHER PUBLICATIONS

Berge, Stephen, M., et al; Review Article: Pharmaceutical Salts; Journal of Pharmaceutical Sciences (1977) vol. 66, No. 1 pp. 1-19.
European Search Report for EP 11187553 Date of Completion of the Search Feb. 10, 2012.
European Search Report for EP 11187566 Date of Completion of the Search May 10, 2012.
Hirsch, Andrew, J., et al; Design, Synthesis, and Structure-Activity relationships of Novel 2-Substituted Pyrazinoylguanidine Epithlial Sodium Channel Blockers: Drugs for Cystic Fibrosis and Chronic Brochitis; Journal of Medicinal Chemistry (2006) vol. 49, No. 14 pp. 4098-4115.
Li, Jack, H., et al; Stereoselective Blockade of Amphibian Epithelial Sodium Channels by Amiloride Analogs; The Journal of Pharmacology and Experimental Therapeutics (1993) vol. 267, No. 3 pp. 1081-1084.
Rogister, Francoise, et al; Novel Inhibitors of the Sodium-Calcium Exchanger: Benzene Ring Analogues of N-Guanidino Substituted Amiloride Derivatives; European Journal of Medicinal Chemistry (2001) vol. 36, No. 7-8 pp. 597-614.
Shepard, Kenneth, L. et al; 3,5-Diamino-6-Chloropyrazinecarboxylic Acid "Active Esters" and Their Reactions (1); Tetrahedron Letters (1969) vol. 54 pp. 4757-4760, Abstract.
Short, James, H. et al., Sympathetic Nervous System Blocking Agents. Derivates of Guanidine and Related Compounds; Journal of Medicinal Chemistry (1963) vol. 6 pp. 275-283.
U.S. Appl. No. 13/662,792, filed Oct. 29, 2012.

*Primary Examiner* — Jeffrey S. Lundgren
*Assistant Examiner* — Chris Simmons
(74) *Attorney, Agent, or Firm* — Michael P. Morris; Edward S. Lazer

(57) ABSTRACT

The present invention relates to compounds of general formula (I)

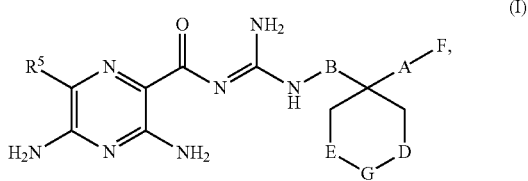

and the tautomers and the salts thereof, particularly the pharmaceutically acceptable salts thereof with inorganic or organic acids and bases, which have valuable pharmacological properties, particularly an inhibitory effect on epithelial sodium channels, and the use thereof for the treatment of diseases, particularly diseases of the lungs and airways.

11 Claims, No Drawings

HETEROCYCLIC COMPOUNDS, MEDICAMENTS CONTAINING SAID COMPOUNDS, USE THEREOF AND PROCESSES FOR THE PREPARATION THEREOF

1. FIELD OF THE INVENTION

The present invention relates to compounds of general formula (I)

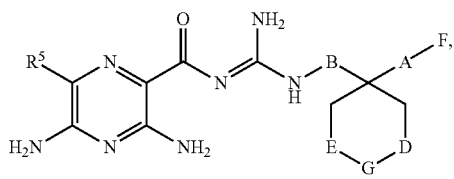

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2. BACKGROUND TO THE INVENTION

Amiloride type compounds are known from the prior art as active substances for example for the treatment of diseases of the lungs and airways (*J. Med. Chem.* 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

3. DETAILED DESCRIPTION OF THE INVENTION

It has surprisingly been found that the problem mentioned above is solved by compounds of formula (I) and (IC) of the present invention.

The present invention therefore relates to a compound of formula (I)

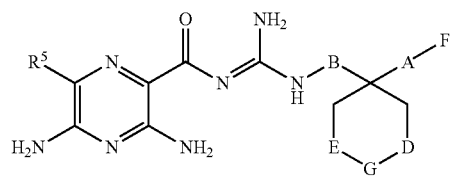

wherein
A denotes a bond or is selected from the group consisting of O, —$CH_2$—, —$CH_2CH_2$—, —$CH_2CH_2CH_2$—, —$CH_2$—O—, —$CH_2$—$NR^{41}$— and —$NR^{41}$—, preferably bond, —$CH_2$— and —$CH_2CH_2$—,
wherein
$R^{41}$ denotes hydrogen or $C_{1-6}$-alkyl, preferably hydrogen or $C_{1-2}$-alkyl,
B denotes
—$CH_2$— or —$CH_2CH_2$—, preferably —$CH_2$—, or provided that A is not O or —$NR^{41}$, B denotes a bond
D, E denote independently from each other a bond or —$CH_2$—, preferably —$CH_2$—,
F denotes optionally substituted aryl, preferably phenyl, preferably substituted by $R^2$, $R^3$, $R^4$, $R^6$, $R^7$, $R^{2a}$, $R^{3a}$, $R^{4a}$, $R^{6a}$ or $R^{7a}$,
or optionally substituted heteroaryl, preferably thiophenyl, pyridyl, pyrimidinyl or pyridonyl, preferably substituted by $R^2$, $R^3$, $R^4$, $R^6$, $R^7$, $R^{2a}$, $R^{3a}$, $R^{4a}$, $R^{6a}$ or $R^{7a}$.
F most preferably denotes phenyl, 4-halo-phenyl, particularly preferred phenyl,
G denotes a group of formula (g.1), (g.2) or (g.3)

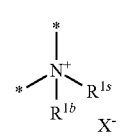

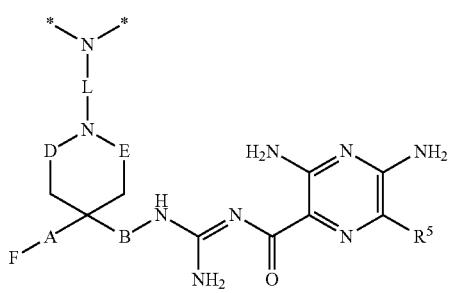

$R^1$ is selected from the group consisting of
hydrogen, $C_{1-6}$alkyl, optionally substituted piperidinyl-CO—, optionally substituted piperazinyl-CO—, optionally substituted piperidinyl-NH—CO—, $R^{1.1}$—$SO_2$—, $R^{1.2}$—$C_{2-4}$-alkyl-NH—CO—, $H_3C$—NH—CO—, $R^{1.2.4}$—O—CO—$CH_2$—NH—CO—, $R^{1.2}$—$C_{2-4}$-alkyl-N($C_{1-4}$-alkyl)-CO—, $H_3C$—N($C_{1-4}$-alkyl)-CO—, $R^{1.2.4}$—O—CO—$CH_2$—N($C_{1-4}$-alkyl)-CO—, $R^{1.3}$—$C_{1-6}$-alkyl-CO—, $R^{1.4}$—$C_{2-6}$-alkyl-, optionally substituted phenyl-$CH_2$—, $R^{1.4.3}$—O—CO—$CH_2$—, HO—CO—$CH_2$— and HO—$SO_2$—$CH_2$—,
$R^{1.5}$—$C_{1-6}$-alkyl-CO— and $R^{1.6}$—C(NH)—,
wherein
$R^{1.1}$ is selected from the group consisting of $C_{1-4}$-alkyl-, $H_2NC(NH)NH$—$C_{1-6}$-alkyl-, $R^{1.2.1}R^{1.2.2}N$—$C_{1-4}$-alkyl-, $R^{1.2.1}R^{1.2.2}R^{1.2.3}N^+$—$C_{1-4}$-alkyl, HOCO—$C_{1-4}$-alkyl- and $C_{1-3}$-alkyl-OCO—$C_{1-4}$-alkyl-,
$R^{1.2}$ is selected from the group consisting of hydrogen, $H_2NC(NH)NH$—, $R^{1.2.1}R^{1.2.2}N$—, $R^{1.2.1}R^{1.2.2}R^{1.2.3}N^+$—, $R^{1.2.3}$—HN—C($NR^{1.2.3}$)—NH—, $R^{1.2.4}$—O—CO—, $R^{1.2.3}$—O—CO—NH— and HO—CO—, $HOSO_2$—, preferably $R^{1.2.1}R^{1.2.2}N$—, $R^{1.2.1}R^{1.2.2}R^{1.2.3}N^+$—, $R^{1.2.3}$—HN—C($NR^{1.2.3}$)—NH— wherein
$R^{1.2.1}$ denotes hydrogen or $C_{1-6}$-alkyl, preferably hydrogen or $C_{1-4}$-alkyl, most preferably $C_{1-4}$-alkyl, $R^{1.2.2}$ denotes hydrogen or $C_{1-6}$-alkyl, preferably hydrogen or $C_{1-4}$-alkyl, most preferably $C_{1-4}$-alkyl, or $R^{1.2.1}$ and $R^{1.2.3}$ together build a 4- to 7-membered heterocyclic ring containing one N-atom, preferably a 6- or 5-membered heterocyclic ring $R^{1.2.3}$ denotes $C_{1-6}$-alkyl, preferably $C_{1-4}$-alkyl, $R^{1.2.4}$ denotes hydrogen or $C_{1-6}$-alkyl, preferably hydrogen or $C_{1-4}$-alkyl, $R^{1.2.5}$ denotes hydrogen or $C_{1-6}$-alkyl, preferably hydrogen or $C_{1-4}$-alkyl, $R^{1.3}$ is selected from the group consisting of hydrogen, $C_{1-6}$-alkyl, $C_{1-6}$-alkyl-O—, optionally substituted phenyl, $R^{1.3.1}R^{1.3.2}N$—, $R^{1.2.1}R^{1.2.2}R^{1.2.3}N^+$—, $R^{1.2.3}$—HN—C(NR$^{1.2.3}$)—NH—, H$_2$NC(NH)NH—, $R^{1.2.4}$—O—CO, HO—CO— and HOSO$_2$—, wherein $R^{1.3.1}$ denotes hydrogen or $C_{1-6}$-alkyl, preferably hydrogen or $C_{1-4}$-alkyl, $R^{1.3.2}$ denotes hydrogen or $C_{1-6}$-alkyl, or $R^{1.3.1}$ and $R^{1.3.2}$ together form a 4- to 7-membered heterocyclic ring containing one N-atom, preferably a 6-membered heterocyclic ring containing one N-atom, preferably hydrogen or $C_{1-4}$-alkyl, $R^{1.4}$ is selected from the group consisting of hydrogen, $R^{1.4.1}R^{1.4.2}N$—, $R^{1.4.1}R^{1.4.2}R^{1.4.3}N^+$—, H$_2$N—C(NH)—NH—, $R^{1.4.3}$—HN—C(NR$^{1.4.4}$)—NH, optionally substituted phenyl, $R^{1.4.3}$—O—CO—, $R^{1.4.4}$—O—CO—NH—, HO—CO— and HOSO$_2$—, wherein $R^{1.4.1}$ denotes hydrogen or $C_{1-6}$-alkyl, preferably hydrogen or $C_{1-4}$-alkyl, $R^{1.4.2}$ denotes hydrogen or $C_{1-6}$-alkyl, preferably hydrogen or $C_{1-4}$-alkyl, $R^{1.4.3}$ denotes hydrogen or $C_{1-6}$-alkyl, preferably hydrogen or $C_{1-4}$-alkyl, most preferably $C_{1-4}$-alkyl, $R^{1.4.4}$ denotes hydrogen or $C_{1-6}$-alkyl, preferably hydrogen or $C_{1-4}$-alkyl, most preferably $C_{1-4}$-alkyl, $R^{1.5}$ is selected from the group consisting of hydrogen, $C_{1-6}$-alkyl-O—, $R^{1.5.1}R^{1.5.2}N$—, $R^{1.5.1}R^{1.5.2}R^{1.5.3}N^+$—, H$_2$N—C(NH)—NH—, optionally substituted phenyl, $R^{1.5.3}$—O—CO—, $R^{1.5.4}$—O—CO—NH—, HO—CO—, HOSO$_2$—, wherein $R^{1.5.1}$ denotes hydrogen or $C_{1-6}$-alkyl, preferably hydrogen or $C_{1-4}$-alkyl, $R^{1.5.2}$ denotes hydrogen or $C_{1-6}$-alkyl, preferably hydrogen or $C_{1-4}$-alkyl, most preferably $C_{1-4}$-alkyl, $R^{1.5.3}$ denotes hydrogen or $C_{1-6}$-alkyl preferably hydrogen or $C_{1-4}$-alkyl, most preferably $C_{1-4}$-alkyl, $R^{1.5.4}$ denotes hydrogen or $C_{1-6}$-alkyl, preferably hydrogen or $C_{1-4}$-alkyl, $R^{1.6}$ denotes $R^{1.6.1}R^{1.6.2}N$—, wherein $R^{1.6.1}$ denotes hydrogen or $C_{1-6}$-alkyl; preferably hydrogen or methyl, $R^{1.6.2}$ denotes hydrogen or $C_{1-6}$-alkyl; preferably hydrogen or methyl, $R^{1b}$ is selected from the group consisting of $C_{1-4}$-alkyl, $R^{1.4}$—$C_{2-6}$-alkyl-, optionally substituted phenyl-CH$_2$—, $R^{1.4.3}$—O—CO—CH$_2$— and HO—CO—CH$_2$—, preferably $C_{1-4}$-alkyl, particularly preferred methyl, wherein $R^{1.4}$ is selected from the group consisting of hydrogen, $R^{1.4.1}R^{1.4.2}N$—, $R^{1.4.1}R^{1.4.2}R^{1.4.3}N^+$—, H$_2$N—C(NH)—NH—, $R^{1.4.3}$—HN—C(NR$^{1.4.4}$)—NH, optionally substituted phenyl, $R^{1.4.3}$—O—CO—, $R^{1.4.4}$—O—CO—NH—, HO—CO— and HOSO$_2$—, wherein $R^{1.4.1}$ denotes hydrogen or $C_{1-6}$-alkyl, preferably hydrogen or $C_{1-4}$-alkyl, $R^{1.4.2}$ denotes hydrogen or $C_{1-6}$-alkyl, preferably hydrogen or $C_{1-4}$-alkyl, $R^{1.4.3}$ denotes hydrogen or $C_{1-6}$-alkyl, preferably hydrogen or $C_{1-4}$-alkyl, most preferably $C_{1-4}$-alkyl, $R^{1.4.4}$ denotes hydrogen or $C_{1-6}$-alkyl, preferably hydrogen or $C_{1-4}$-alkyl, most preferably $C_{1-4}$-alkyl, $R^{1s}$ denotes $C_{1-6}$-alkyl, preferably methyl, $X^-$ denotes any anion forming a pharmaceutically acceptable salt, preferably selected from among CF$_3$—COO$^-$, Cl$^-$, I$^-$, Br$^-$, HCOO$^-$ and CH$_3$—COO$^-$, most preferably Cl$^-$ and CF$_3$—COO$^-$, L denotes a bridging group —CO—NH—$C_{2-6}$-alkyl-NH—CO—, —COC$_{1-6}$-alkyl-CO—, or —$C_{2-6}$-alkyl-, forming a compound of formula (IC), whereby the molecular entities of formula (IC) connected by L may be identical or different (IC)

$R^5$ denotes Cl or Br, preferably Cl, optionally in the form of the tautomers, the racemates, the enantiomers, the diastereomers and the mixtures thereof, optionally in form of the hydrates, solvates or prodrugs thereof and optionally the pharmacologically acceptable acid addition salts thereof.

Preferred compounds of formula (IA), (IB) or (IC.1) are those wherein (IA)

-continued

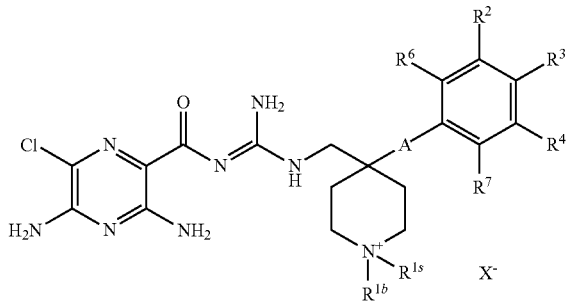
(IB)

A denotes a bond, —$CH_2$—, —$CH_2CH_2$— or $CH_2$—O—, preferably —$CH_2CH_2$—, $R^1$ is selected from the group consisting of
hydrogen, $C_{1-6}$alkyl, $R^{1.1}$—$SO_2$—, $R^{1.2}$—$C_{2-4}$-alkyl-NH—CO—, $H_3C$—NH—CO—, $R^{1.2.4}$—O—CO—$CH_2$—NH—CO—, $R^{1.2}$—$C_{2-4}$-alkyl-N($C_{1-4}$-alkyl)-CO—, $H_3C$—N($C_{1-4}$-alkyl)-CO—, $R^{1.2.4}$—O—CO—$CH_2$—N($C_{1-4}$-alkyl)-CO—, $R^{1.3}$—$C_{1-6}$-alkyl-CO—, $R^{1.4}$—$C_{2-6}$-alkyl-, optionally substituted phenyl-$CH_2$—, $R^{1.4.3}$—O—CO—$CH_2$—, HO—CO—$CH_2$— and $HOSO_2$—$CH_2$—, $R^{1.5}$—$C_{1-6}$-alkyl-CO— and $R^{1.6}$—C(NH)—,
wherein
$R^{1.1}$ denotes $C_{1-4}$-alkyl-;
$R^{1.2}$ is selected from the group consisting of
hydrogen, $R^{1.2.1}R^{1.2.2}N$—, $R^{1.2.1}R^{1.2.2}R^{1.2.3}N^+$—, $R^{1.2.4}$—O—CO—, HO—CO— and $R^{1.2.5}$—O—CO—NH—,
wherein
$R^{1.2.1}$ denotes hydrogen or $C_{1-6}$-alkyl; preferably hydrogen or $C_{1-4}$-alkyl,
$R^{1.2.2}$ denotes hydrogen or $C_{1-6}$-alkyl; preferably hydrogen or $C_{1-4}$-alkyl,
$R^{1.2.3}$ denotes hydrogen or $C_{1-6}$-alkyl; preferably hydrogen or $C_{1-4}$-alkyl,
$R^{1.2.4}$ denotes $C_{1-6}$-alkyl; preferably $C_{1-4}$-alkyl,
$R^{1.2.5}$ denotes $C_{1-6}$-alkyl; preferably $C_{1-4}$-alkyl,
$R^{1.3}$ is selected from the group consisting of hydrogen, $C_{1-6}$-alkyl, $C_{1-6}$-alkyl-O—, and optionally substituted phenyl
$R^{1.4}$ is selected from the group consisting of hydrogen, $R^{1.4.1}R^{1.4.2}N$—, $R^{1.4.1}R^{1.4.2}R^{1.4.3}N^+$—, $H_2N$—C(NH)—NH—, $R^{1.4.3}$—HN—C($NR^{1.4.4}$)—NH—, optionally substituted phenyl, $R^{1.4.3}$—O—CO—, $R^{1.4.4}$—O—CO—NH—, HO—CO— and $HOSO_2$—,
wherein
$R^{1.4.1}$ denotes hydrogen or $C_{1-6}$-alkyl, preferably hydrogen or $C_{1-4}$-alkyl,
$R^{1.4.2}$ denotes hydrogen or $C_{1-6}$-alkyl, preferably hydrogen or $C_{1-4}$-alkyl,
$R^{1.4.3}$ denotes hydrogen or $C_{1-6}$-alkyl, preferably hydrogen or $C_{1-4}$-alkyl, most preferably $C_{1-4}$-alkyl,
$R^{1.4.4}$ denotes hydrogen or $C_{1-6}$-alkyl, preferably hydrogen or $C_{1-4}$-alkyl, most preferably $C_{1-4}$-alkyl,
$R^{1.5}$ is selected from the group consisting of hydrogen, $C_{1-6}$-alkyl-O—, $R^{1.5.1}R^{1.5.2}N$—, $R^{1.2.1}R^{1.2.2}R^{1.2.3}N^+$—, $H_2N$—C(NH)—NH—, $R^{1.5.3}$—O—CO—, $R^{1.5.4}$—O—CO—NH—, optionally substituted phenyl,
wherein
$R^{1.5.1}$ denotes hydrogen or $C_{1-6}$-alkyl, preferably hydrogen or $C_{1-4}$-alkyl,
$R^{1.5.2}$ denotes hydrogen or $C_{1-6}$-alkyl, preferably hydrogen or $C_{1-4}$-alkyl, most preferably $C_{1-4}$-alkyl,
$R^{1.5.3}$ denotes hydrogen or $C_{1-6}$-alkyl, preferably hydrogen or $C_{1-4}$-alkyl, most preferably $C_{1-4}$-alkyl,
$R^{1.5.4}$ denotes hydrogen or $C_{1-6}$-alkyl, preferably hydrogen or $C_{1-4}$-alkyl,
$R^{1.6}$ denotes $R^{1.6.1}R^{1.6.2}N$—,
wherein
$R^{1.6.1}$ denotes hydrogen or $C_{1-6}$-alkyl; preferably hydrogen or methyl,
$R^{1.6.2}$ denotes hydrogen or $C_{1-6}$-alkyl; preferably hydrogen or methyl,
$R^{1b}$ denotes $C_{1-4}$-alkyl, preferably methyl,
$R^{1s}$ denotes $C_{1-6}$-alkyl, preferably methyl,
$X^-$ denotes any anion forming a pharmaceutically acceptable salt, preferably selected from among $CF_3$—$COO^-$, $Cl^-$, $Br^-$, $HCOO^-$ and $CH_3$—$COO^-$, most preferably $Cl^-$ and $CF_3$—$COO^-$,
L denotes a bridging group —CO—NH—$C_{2-6}$-alkyl-NH—CO—, —$COC_{1-6}$-alkyl-CO— or —$C_{2-6}$-alkyl-, forming a compound of formula (IC.1),
whereby the molecular entities of formula (IC.1) connected by L may be identical or different

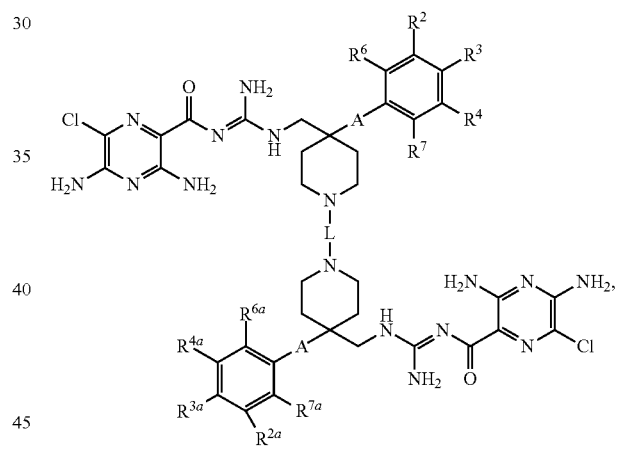
(IC.1)

$R^2, R^3, R^4, R^6, R^7, R^{2a}, R^{3a}, R^{4a}, R^{6a}, R^{7a}$ independently from each other are selected from the group consisting of hydrogen, halogen, CN, $C_{1-4}$alkyl, $C_{1-3}$-alkyl-O—, $C_{1-3}$-alkyl-OCO—, —$COOR^{4.1}$, —$CONR^{4.2}R^{4.3}$ and —$OR^{4.1}$, preferably hydrogen,
wherein
$R^{4.1}$ denotes hydrogen or $C_{1-4}$-alkyl, preferably hydrogen or $C_{1-2}$-alkyl, particularly preferred hydrogen or methyl
$R^{4.2}$ denotes hydrogen or $C_{1-4}$-alkyl, preferably hydrogen or $C_{1-2}$-alkyl, particularly preferred hydrogen or methyl
$R^{4.3}$ denotes hydrogen or $C_{1-4}$-alkyl, preferably hydrogen or $C_{1-2}$-alkyl, particularly preferred hydrogen or methyl
or
$R^3$ and $R^4$ or $R^{3a}$ and $R^{4a}$ together denote —O—$C_{1-3}$-alkyl-O—; preferably —O—$C_{1-2}$-alkyl-O—,
optionally in the form of the tautomers, the racemates, the enantiomers, the diastereomers and the mixtures thereof, optionally in form of the hydrates, solvates or prodrugs thereof and optionally the pharmacologically acceptable acid addition salts thereof.

Particularly preferred are compounds of formula (IA), wherein
A denotes a bond, —CH$_2$— or —CH$_2$CH$_2$—,
R$^1$ is selected from the group consisting of
hydrogen, C$_{1-6}$-alkyl, C$_{1-4}$-alkyl-SO$_2$—, C$_{1-4}$-alkyl-NH—CO—, H$_2$N—CO—, H$_2$N—C$_{1-4}$-alkyl-, H$_2$N—C$_{1-4}$-alkyl-CO—, H$_2$N—C$_{1-4}$-alkyl-NH—CO—, Phenyl-CO—, Phenyl-CH$_2$—CO—, Phenyl-CH$_2$—, C$_{1-6}$-alkyl-CO—, C$_{1-6}$-alkyl-O—C$_{1-4}$-alkyl-CO—, (CH$_3$)$_2$N—C$_{1-4}$-alkyl-, (CH$_3$)$_2$N—C$_{1-4}$-alkyl-NH—CO—, (CH$_3$)$_3$N$^+$—C$_{1-4}$-alkyl-NH—CO—, (CH$_3$)$_3$N$^+$—C$_{1-4}$-alkyl-CO—, (CH$_3$)$_3$N$^+$—C$_{2-4}$-alkyl-, (CH$_3$)N$^+$—C$_{1-4}$-alkyl-N(C$_{1-4}$-alkyl)-CO—, H$_2$N—C(NH)—NH—C$_{1-6}$—NH—CO—, C$_{1-6}$-alkyl-O—CO—, C$_{1-6}$-alkyl-O—CO—C$_{1-4}$-alkyl-, C$_{1-6}$-alkyl-O—CO—C$_{1-4}$-alkyl-CO—, C$_{1-6}$-alkyl-O—CO—C$_{1-4}$-alkyl-NH—CO—, C$_{1-6}$-alkyl-O—CO—NH—C$_{1-4}$-alkyl-, C$_{1-6}$-alkyl-O—CO—NH—C$_{1-4}$-alkyl-CO—, C$_{1-6}$-alkyl-O—CO—NH—C$_{1-4}$-alkyl-NH—CO—, HOCO—C$_{1-4}$-alkyl-, HOCO—C$_{1-4}$-alkyl-CO—, HOCO—C$_{1-4}$-alkyl-NH—CO—, H$_2$N—CNH— and H$_2$NC(NH)NH—C$_{1-6}$-alkyl-CO—,
R$^2$ independently from each other are selected from the group consisting of hydrogen, halogen, CN, C$_{1-4}$-alkyl and C$_1$-alkyl-O—,
R$^6$ independently from each other are selected from the group consisting of hydrogen, halogen, CN, C$_{1-4}$-alkyl and C$_1$-alkyl-O—
R$^3$ are selected from the group consisting of hydrogen, halogen, CN and C$_{1-4}$-alkyl,
R$^4$ independently from each other are selected from the group consisting of hydrogen, halogen, CN, C$_{1-4}$-alkyl, C$_{1-4}$-alkyl-OCO—, —COOR$^{4.1}$ and —CONR$^{4.2}$R$^{4.3}$, wherein
R$^{4.1}$ denotes hydrogen or C$_{1-4}$-alkyl, preferably hydrogen or methyl;
R$^{4.2}$ denotes hydrogen or C$_{1-4}$-alkyl, preferably hydrogen or methyl;
R$^{4.3}$ denotes hydrogen or C$_{1-4}$-alkyl, preferably hydrogen or methyl; or
R$^3$ and R$^4$ together denote —O—C$_{1-3}$-alkyl-O—; preferably —O—C$_{1-2}$-alkyl-O—;
optionally in the form of the tautomers, the racemates, the enantiomers, the diastereomers and the mixtures thereof, and optionally the pharmacologically acceptable acid addition salts thereof.

Also particularly preferred are compounds of formula (IC.1) wherein
A denotes a bond, —CH$_2$— or —CH$_2$CH$_2$—,
L denotes a bridging group —CO—NH—C$_{2-6}$-alkyl-NH—CO—,
forming a compound of formula IC or IC.1,
R$^2$, R$^{2a}$ independently from each other are selected from the group consisting of hydrogen, halogen, CN, C$_{1-4}$-alkyl and C$_1$alkyl-O—,
R$^6$, R$^{6a}$ independently from each other are selected from the group consisting of hydrogen, halogen, CN, C$_{1-4}$-alkyl and C$_1$alkyl-O—
R$^3$, R$^{3a}$ are selected from the group consisting of hydrogen halogen, CN and C$_{1-4}$-alkyl,
R$^4$, R$^{4a}$ independently from each other are selected from the group consisting of hydrogen halogen, CN, C$_{1-4}$-alkyl, C$_{1-4}$-alkyl-OCO—, —COOR$^{4.1}$ and —CONR$^{4.2}$R$^{4.3}$, wherein
R$^{4.1}$ denotes hydrogen or C$_{1-4}$-alkyl, preferably hydrogen or methyl;
R$^{4.2}$ denotes hydrogen or C$_{1-4}$-alkyl, preferably hydrogen or methyl;
R$^{4.3}$ denotes hydrogen or C$_{1-4}$-alkyl, preferably hydrogen or methyl; or
R$^3$ and R$^4$ or R$^{3a}$ and R$^{4a}$ together denote —O—C$_{1-3}$-alkyl-O—; preferably O—C$_{1-2}$-alkyl-O—;
optionally in the form of the tautomers, the racemates, the enantiomers, the diastereomers and the mixtures thereof, and optionally the pharmacologically acceptable acid addition salts thereof.

Also particularly preferred are compounds of formula (IB) wherein
R$^{1b}$ denotes C$_{1-4}$-alkyl, preferrably methyl, and
R$^{1s}$ denotes C$_{1-6}$-alkyl, preferably methyl,
optionally in the form of the tautomers, the racemates, the enantiomers, the diastereomers and the mixtures thereof, optionally in form of the hydrates, solvates or prodrugs thereof and optionally the pharmacologically acceptable acid addition salts thereof.

Also particularly preferred are compounds of formula (IC) wherein
L denotes a bridging group —CO—NH—C$_{2-6}$-alkyl-NH—CO—,
forming a compound of formula (IC) or (IC.1),
optionally in the form of the tautomers, the racemates, the enantiomers, the diastereomers and the mixtures thereof, optionally in form of the hydrates, solvates or prodrugs thereof and optionally the pharmacologically acceptable acid addition salts thereof.

Especially preferred are compounds of formula (IA), (IB) or (IC.1), wherein
R$^2$, R$^3$, R$^4$, R$^6$ and R$^7$ denote hydrogen.

Also especially preferred are compounds of formula (IA), (IB) or (IC.1), wherein
R$^2$, R$^3$, R$^4$, R$^6$, R$^7$, R$^{2a}$, R$^{3a}$, R$^{4a}$, R$^{6a}$ and R$^{7a}$ denote hydrogen.

Also especially preferred are compounds of formula (IA), (IB) or (IC), wherein
A denotes —CH$_2$CH$_2$—, and
E, D denote —CH$_2$—

A further embodiment of the current invention are compounds of formula (I), (IA), (IB) or (IC) or a pharmaceutically acceptable salt thereof as a medicament, preferably compounds of formula (IA), (IB) or (IC)

A further embodiment of the current invention are compounds of formula (I), (IA), (IB) or (IC), preferably compounds of formula (IA), (IB) or (IC), or a pharmaceutically acceptable salt thereof for the treatment of respiratory diseases or complaints, and allergic diseases of the airways.

Preferred are compounds of formula (I) or (IC), preferably compounds of formula (IA), (IB) or (IC), or a pharmaceutically acceptable salt thereof for the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, e.g. radiation-induced or caused by aspiration or infectious pneumonitis, preferably chronic bronchitis, acute bronchitis, bronchitis, chronic obstructive bronchitis (COPD), asthma (intrinsic or allergic), cystic fibrosis and pediatric asthma, preferably chronic bronchitis, COPD and cystic fibrosis.

A pharmaceutical composition comprising at least one compound according to the invention or a pharmaceutically acceptable salt thereof and a pharmaceutically acceptable carrier.

A further embodiment of the current invention is medicament combinations which contain, besides one or more compounds according to the invention, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, and cystic fibrosis transmembrane regulator (CFTR) and CFTR potentiators, preferably VX-770 and VX-809, or double or triple combinations thereof.

4. USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last or first named subgroup hyphenated at the end is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

When a compound of the present invention is depicted in the form of a chemical name and as a formula, in case of any discrepancy the formula shall prevail. An asterisk may be used in sub-formulas to indicate the bond which is connected to the core molecule as defined.

For example, the term "3-carboxypropyl-group" represents the following substituent:

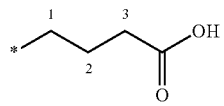

wherein the carboxy group is attached to the third carbon atom of the propyl group. The terms "1-methylpropyl-", "2,2-dimethylpropyl-" or "cyclopropylmethyl-" group represent the following groups:

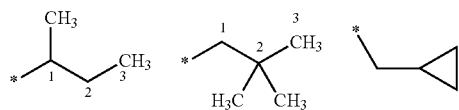

The asterisk may be used in sub-formulas to indicate the bond which is connected to the core molecule as defined.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as is well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxyide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulf uric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds.

The prodrug is formulated with the objectives of improved chemical stability, improved patient acceptance and compliance, improved bioavailability, prolonged duration of action, improved organ selectivity, improved formulation (e.g., increased hydro-solubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocyclic ring" means a saturated or unsaturated mono- or polycyclic-ring system containing one or more heteroatoms selected from N, O or $S(O)_r$, wherein r=0, 1 or 2, consisting of 3 to 14 ring atoms. The term "heterocycle" is intended to include all the possible isomeric forms.

Thus, the term "heterocyclyl" or "heterocyclic ring" includes the following exemplary structures which are not depicted as radicals as each form may be attached through a covalent bond to any atom so long as appropriate valences are maintained:

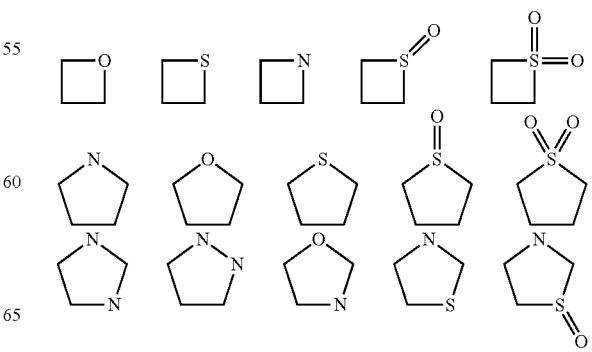

-continued
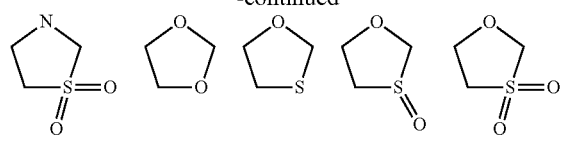
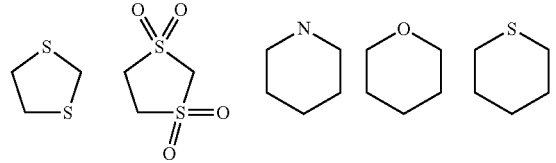
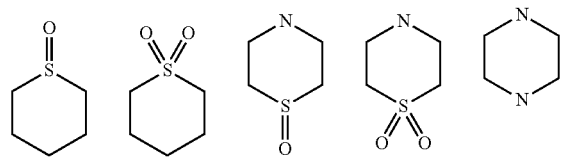
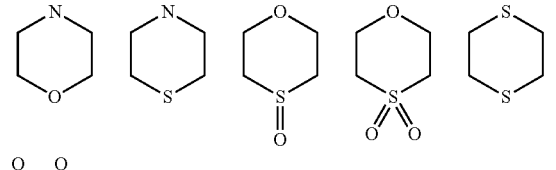
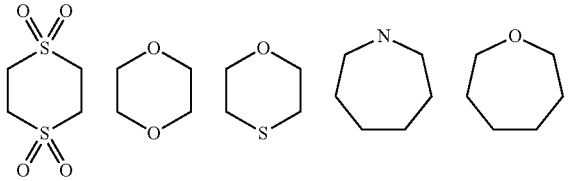
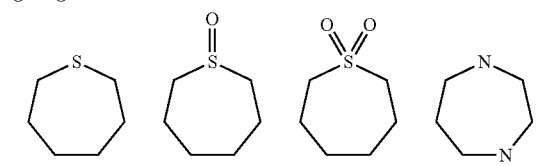
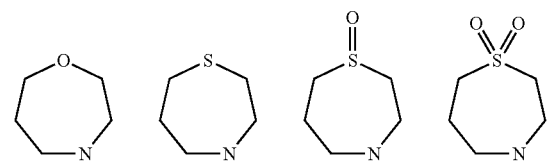
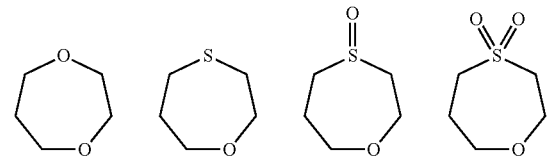
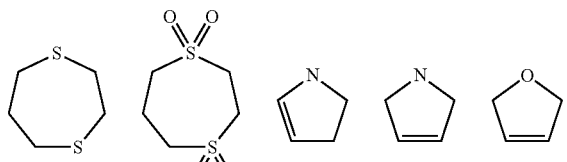
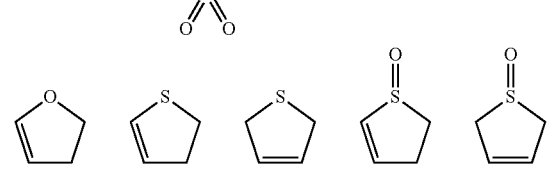
-continued
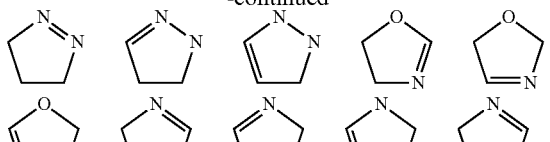
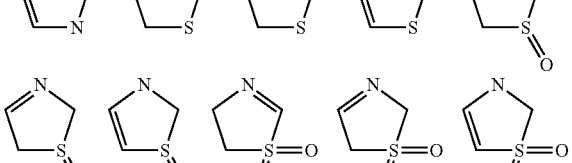
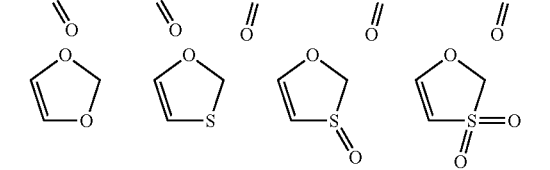
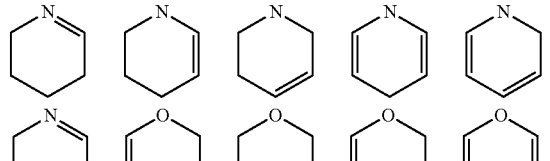
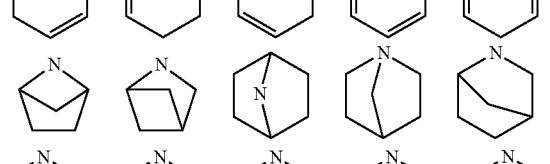
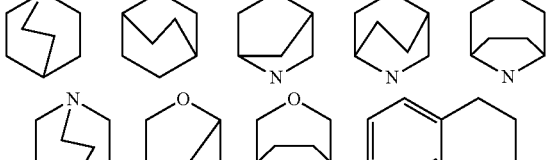
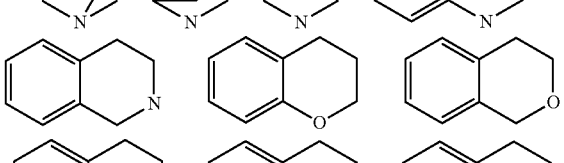
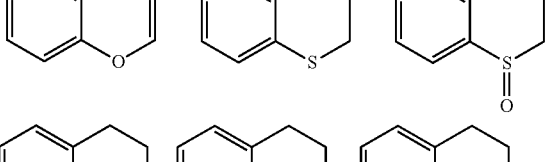
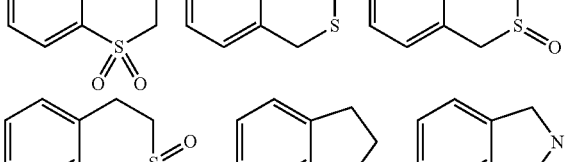
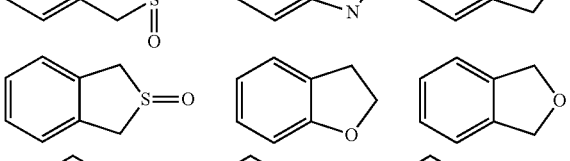

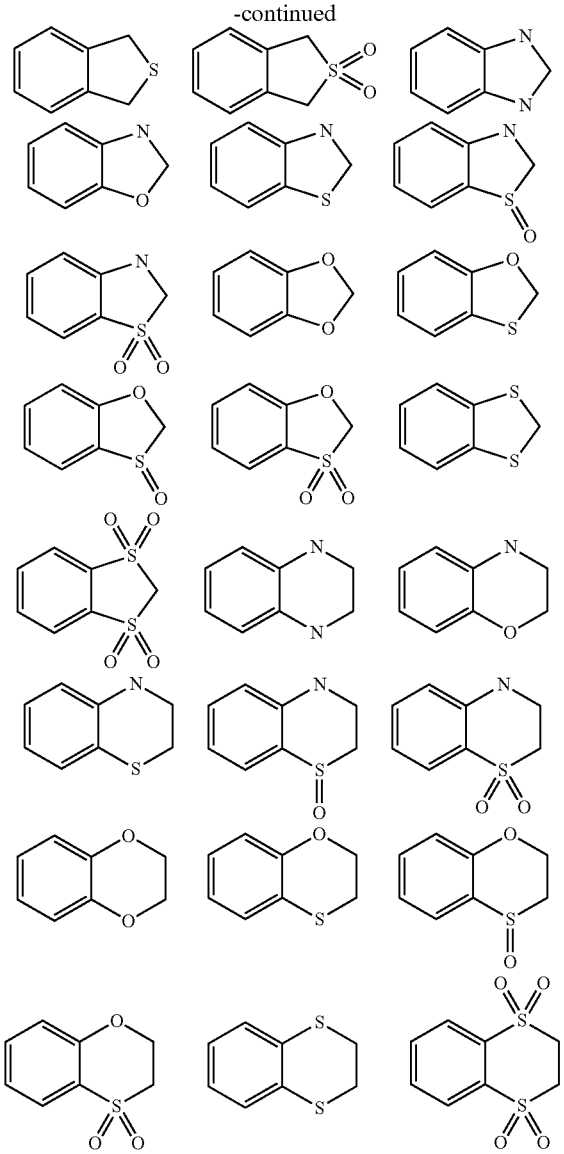

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

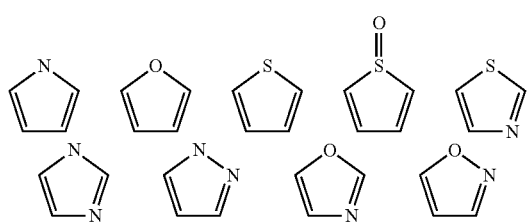

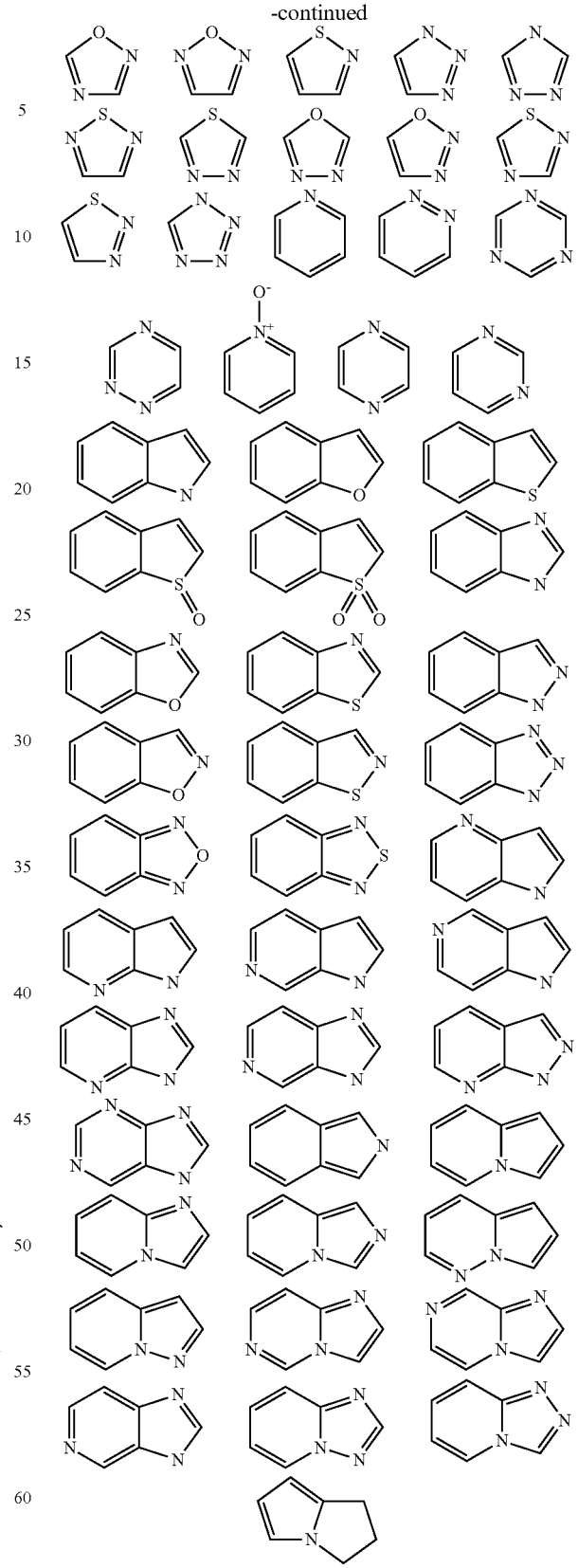

The term "monocyclic C$_{5-7}$-heterocyclyl" means a saturated or unsaturated non-aromatic monocyclic-ring system containing one or more heteroatoms selected from N, O or S(O)$_r$, wherein r=0, 1 or 2, consisting of 5 to 7 ring atoms. The term "monocyclic C$_{5-7}$-heterocyclyl" is intended to include all the possible isomeric forms.

Thus, the term "monocyclic C$_{5-7}$-heterocyclyl" includes the following exemplary structures is which are not depicted as radicals as each form may be attached through a covalent bond to any atom so long as appropriate valences are maintained:

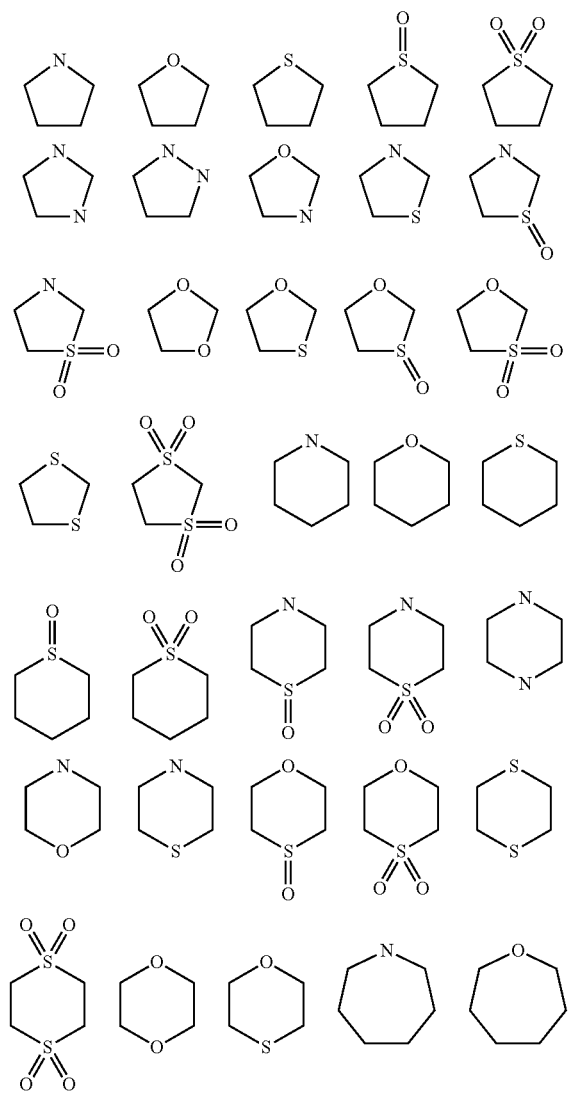

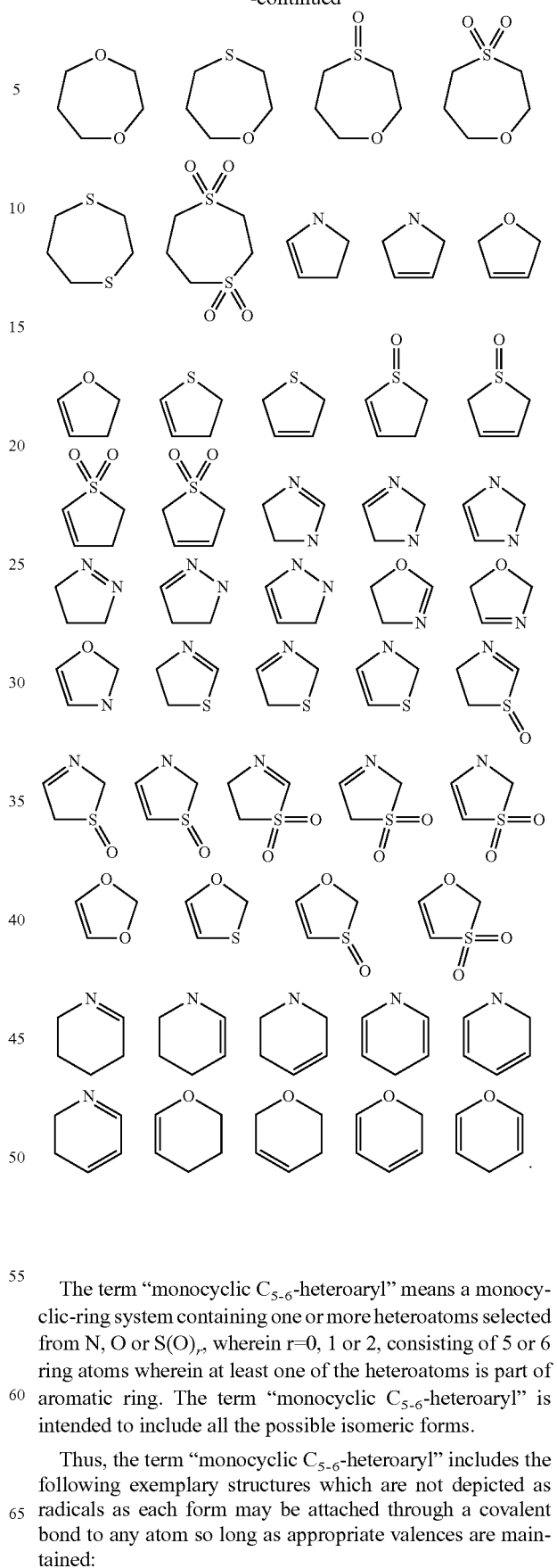

The term "monocyclic C$_{5-6}$-heteroaryl" means a monocyclic-ring system containing one or more heteroatoms selected from N, O or S(O)$_r$, wherein r=0, 1 or 2, consisting of 5 or 6 ring atoms wherein at least one of the heteroatoms is part of aromatic ring. The term "monocyclic C$_{5-6}$-heteroaryl" is intended to include all the possible isomeric forms.

Thus, the term "monocyclic C$_{5-6}$-heteroaryl" includes the following exemplary structures which are not depicted as radicals as each form may be attached through a covalent bond to any atom so long as appropriate valences are maintained:

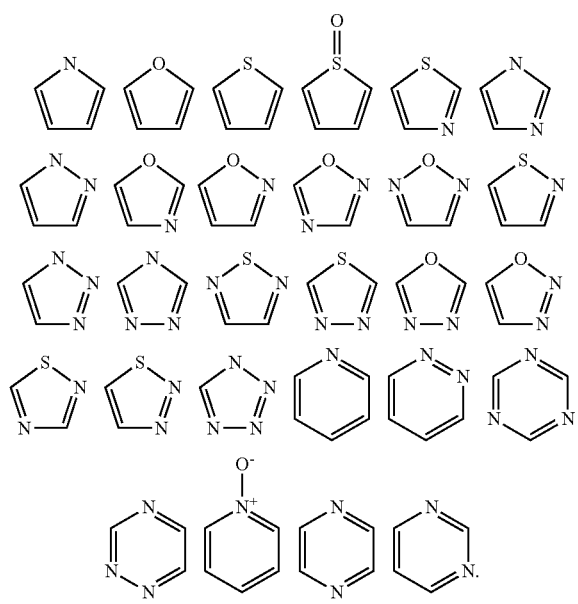

The term "bicyclic $C_{8-10}$-heterocyclyl" means a saturated or unsaturated bicyclic-ring system including aromatic ring systems containing one or more heteroatoms selected from N, O or $S(O)_r$, wherein r=0, 1 or 2, consisting of 8 to 10 ring atoms wherein the heteroatoms is optionally part of the aromatic ring. The term "bicyclic $C_{8-10}$-heterocyclyl" is intended to include all the possible isomeric forms.

Thus, the term "bicyclic $C_{8-10}$-heterocyclyl" includes the following exemplary structures which are not depicted as radicals as each form may be attached through a covalent bond to any atom so long as appropriate valences are maintained:

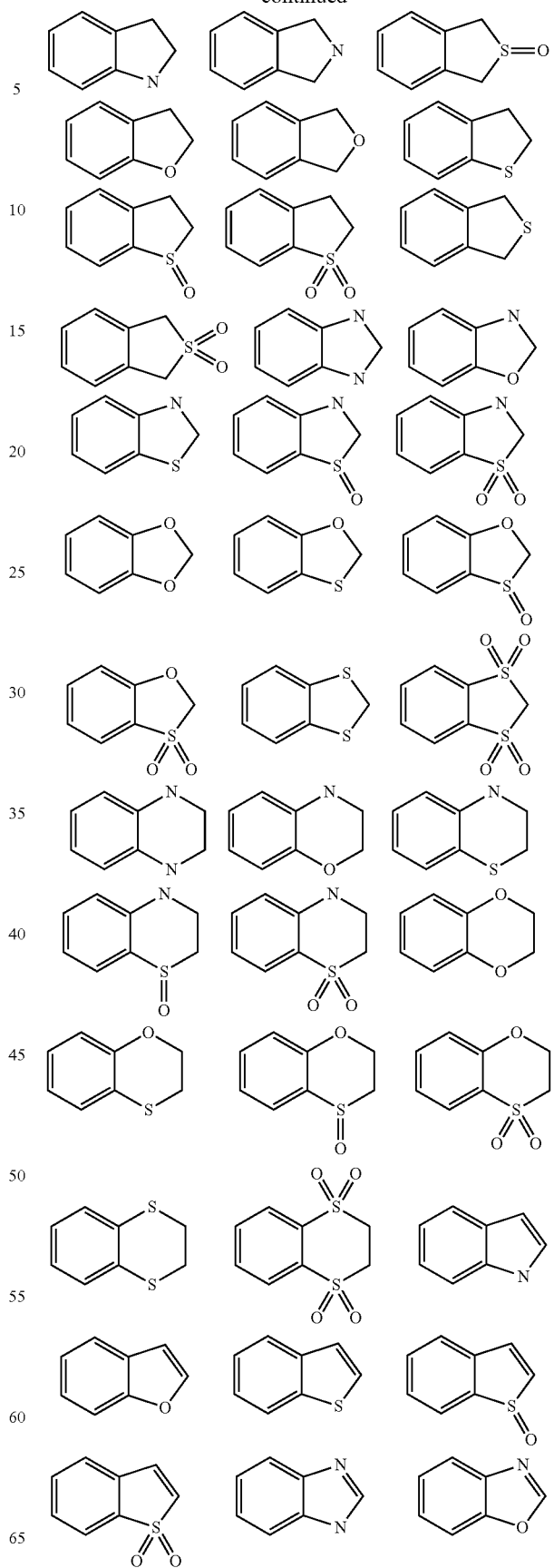

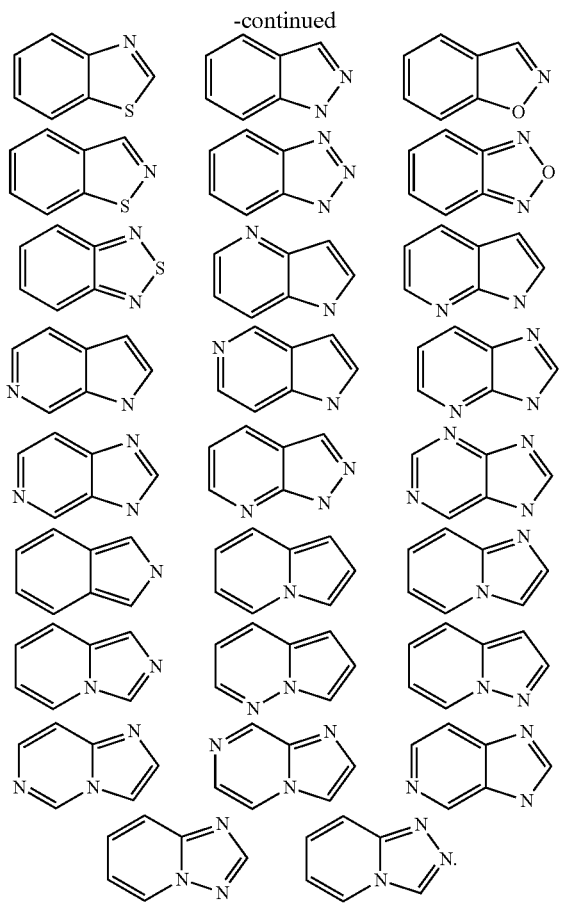

The term "annelated species of aryl or heterocyclyl" as used herein, either alone or in combination with another substituent wherein the annelated species presents as an aryl-het (a), a het-aryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of an annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂, H₃C—CH₂—CH₂—CH₂—CH₂—, H₃C—CH₂—CH₂—CH(CH₃)—, H₃C—CH₂—CH(CH₃)—CH₂, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

In all cases of contradictions between structure and their naming structure shall prevail.

5. PREFERRED EMBODIMENTS

The symbol A denotes a bond or is selected from the group consisting of O, —CH₂—, —CH₂CH₂—, —CH₂CH₂CH₂—, —CH₂—O—, —CH₂—NR$^{41}$— and —NR$^{41}$—, preferably bond, —CH₂— and —CH₂CH₂—, wherein $R^{41}$ denotes hydrogen or $C_{1-6}$-alkyl, preferably hydrogen or $C_{1-2}$-alkyl.

The symbol B denotes —CH₂— or —CH₂CH₂—, preferably —CH₂—, or provided that A is not O or —NR$^{41}$, a bond.

The symbol D denotes a bond or —CH₂—, preferably —CH₂—.

The symbol E denotes a bond or —CH₂—, preferably —CH₂—.

The symbol F denotes optionally substituted aryl, preferably phenyl, preferably substituted by $R^2$, $R^3$, $R^4$, $R^6$, $R^7$, $R^{2a}$, $R^{3a}$, $R^{4a}$, $R^{6a}$ or $R^{7a}$ or optionally substituted heteroaryl, preferably thiophenyl, pyridyl, pyrimidinyl or pyridonyl, most preferably phenyl, 4-halo-phenyl or pyridyl, particularly preferred phenyl.

The symbol G denotes a group of formula (g.1), (g.2) or (g.3)

(g.1)

(g.2)

-continued

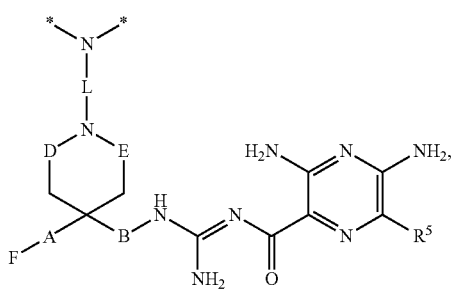
(g.3)

The substituent $R^1$ is selected from the group consisting of hydrogen, $C_{1-6}$alkyl, optionally substituted piperidinyl-CO—, optionally substituted piperazinyl-CO—, optionally substituted piperidinyl-NH—CO—, $R^{1.1}$—$SO_2$—, $R^{1.2}$—$C_{2-4}$-alkyl-NH—CO—, $H_3C$—NH—CO—, $R^{1.2.4}$—O—CO—$CH_2$—NH—CO—, $R^{1.2}$—$C_{2-4}$-alkyl-N($C_{1-4}$-alkyl)-CO—, $H_3C$—N($C_{1-4}$-alkyl)-CO—, $R^{1.2.4}$—O—CO—$CH_2$—N($C_{1-4}$-alkyl)-CO—, $R^{1.3}$—$C_{1-6}$-alkyl-CO—, $R^{1.4}$—$C_{2-6}$-alkyl-, optionally substituted phenyl-$CH_2$—, $R^{1.4.3}$—O—CO—$CH_2$—, HO—CO—$CH_2$— and HO—$SO_2$—$CH_2$—, $R^{1.5}$—$C_{1-6}$-alkyl-CO— and $R^{1.6}$—C(NH)—, wherein $R^{1.1}$ is selected from the group consisting of $C_{1-4}$-alkyl-, $H_2NC(NH)NH$—$C_{1-6}$-alkyl-, $R^{1.2.1}R^{1.2.2}N$—$C_{1-4}$-alkyl-, $R^{1.2.1}R^{1.2.2}R^{1.2.3}N^+$—$C_{1-4}$-alkyl, HOCO—$C_{1-4}$-alkyl- and $C_{1-3}$-alkyl-OCO—$C_{1-4}$-alkyl-, $R^{1.2}$ is selected from the group consisting of hydrogen, $H_2NC(NH)NH$—, $R^{1.2.1}R^{1.2.2}N$—, $R^{1.2.1}R^{1.2.2}R^{1.2.3}N^+$—, $R^{1.2.3}$—HN—C(N$R^{1.2.3}$)—NH—, $R^{1.2.4}$—O—CO—, $R^{1.2.5}$—O—CO—NH— and HO—CO—, $HOSO_2$—, preferably $R^{1.2.1}R^{1.2.2}N$—, $R^{1.2.1}R^{1.2.2}R^{1.2.3}N^+$—, $R^{1.2.3}$—HN—C(N$R^{1.2.3}$)—NH—, wherein $R^{1.2.1}$ denotes hydrogen or $C_{1-6}$-alkyl, preferably hydrogen or $C_{1-4}$-alkyl, more preferably $C_{1-4}$-alkyl, most preferably methyl $R^{1.2.2}$ denotes hydrogen or $C_{1-6}$-alkyl, preferably hydrogen or $C_{1-4}$-alkyl, More preferably $C_{1-4}$-alkyl, most preferably methyl or $R^{1.2.1}$ and $R^{1.2.2}$ together build a 4- to 7-membered heterocyclic ring containing one N-atom, preferably a 5- or 6-membered heterocyclic ring $R^{1.2.3}$ denotes $C_{1-6}$-alkyl, preferably $C_{1-4}$-alkyl, most preferably methyl $R^{1.2.4}$ denotes hydrogen or $C_{1-6}$-alkyl, preferably hydrogen or $C_{1-4}$-alkyl, $R^{1.2.5}$ denotes hydrogen or $C_{1-6}$-alkyl, preferably hydrogen or $C_{1-4}$-alkyl, $R^{1.3}$ is selected from the group consisting of hydrogen, $C_{1-6}$-alkyl, $C_{1-6}$-alkyl-O—, optionally substituted phenyl, $R^{1.3.1}R^{1.3.2}N$—, $R^{1.2.1}R^{1.2.2}R^{1.2.3}N^+$—, $R^{1.2.3}$—HN—C(N$R^{1.2.3}$)—NH, $H_2NC(NH)NH$—, $R^{1.2.4}$—O—CO, HO—CO— and $HOSO_2$—, wherein $R^{1.3.1}$ denotes hydrogen or $C_{1-6}$-alkyl, preferably hydrogen or $C_{1-4}$-alkyl, $R^{1.3.2}$ denotes hydrogen or $C_{1-6}$-alkyl, or $R^{1.3.1}$ and $R^{1.3.2}$ together build a 4- to 7-membered heterocyclic ring containing one N-atom, preferably a 5- or 6-membered heterocyclic ring containing one N-atom, preferably hydrogen or $C_{1-4}$-alkyl, $R^{1.4}$ is selected from the group consisting of hydrogen, $R^{1.4.1}R^{1.4.2}N$—, $R^{1.4.1}R^{1.4.2}R^{1.4.3}N^+$—, $H_2N$—C(NH)—NH—, $R^{1.4.3}$—HN—C(N$R^{1.4.4}$)—NH—, optionally substituted phenyl, $R^{1.4.3}$—O—CO—, $R^{1.4.4}$—O—CO—NH—, HO—CO— and $HOSO_2$—, wherein $R^{1.4.1}$ denotes hydrogen or $C_{1-6}$-alkyl, preferably hydrogen or $C_{1-4}$-alkyl, $R^{1.4.2}$ denotes hydrogen or $C_{1-6}$-alkyl, preferably hydrogen or $C_{1-4}$-alkyl, $R^{1.4.3}$ denotes hydrogen or $C_{1-6}$-alkyl, preferably hydrogen or $C_{1-4}$-alkyl, most preferably $C_{1-4}$-alkyl, $R^{1.4.4}$ denotes hydrogen or $C_{1-6}$-alkyl, preferably hydrogen or $C_{1-4}$-alkyl, most preferably $C_{1-4}$-alkyl, $R^{1.5}$ is selected from the group consisting of hydrogen, $C_{1-6}$-alkyl-O—, $R^{1.5.1}R^{1.5.2}N$—, $R^{1.5.1}R^{1.5.2}R^{1.5.3}N^+$—, $H_2N$—C(NH)—NH—, optionally substituted phenyl, $R^{1.5.3}$—O—CO—, $R^{1.5.4}$—O—CO—NH—, HO—CO—, $HOSO_2$—, wherein $R^{1.5.1}$ denotes hydrogen or $C_{1-6}$-alkyl, preferably hydrogen or $C_{1-4}$-alkyl, $R^{1.5.2}$ denotes hydrogen or $C_{1-6}$-alkyl, preferably hydrogen or $C_{1-4}$-alkyl, most preferably $C_{1-4}$-alkyl, $R^{1.5.3}$ denotes hydrogen or $C_{1-6}$-alkyl preferably hydrogen or $C_{1-4}$-alkyl, most preferably $C_{1-4}$-alkyl, $R^{1.5.4}$ denotes hydrogen or $C_{1-6}$-alkyl, preferably hydrogen or $C_{1-4}$-alkyl, $R^{1.6}$ denotes $R^{1.6.1}R^{1.6.2}N$—, wherein $R^{1.6.1}$ denotes hydrogen or $C_{1-6}$-alkyl, preferably hydrogen or methyl, $R^{1.6.2}$ denotes hydrogen or $C_{1-6}$-alkyl, preferably hydrogen or methyl.

Preferably $R^1$ is selected from the group consisting of hydrogen, $C_{1-6}$-alkyl, $C_{1-4}$-alkyl-$SO_2$—, $C_{1-4}$-alkyl-NH—CO—, $H_2N$—CO—, $H_2N$—$C_{1-4}$-alkyl-, $H_2N$—$C_{1-4}$-alkyl-CO—, $H_2N$—$C_{1-4}$-alkyl-NH—CO—, Phenyl-CO—, Phenyl-$CH_2$—CO—, Phenyl-$CH_2$—, $C_{1-6}$-alkyl-CO—, $C_{1-6}$-alkyl-O—$C_{1-4}$-alkyl-CO—, $(CH_3)_2N$—$C_{1-4}$-alkyl-, $(CH_3)_2N$—$C_{1-4}$-alkyl-NH—CO—, $(CH_3)_3N^+$—$C_{1-4}$-alkyl-NH—CO—, $(CH_3)_3N^+$—$C_{1-4}$-alkyl-N($C_{1-4}$-alkyl)-CO—, $(CH_3)_3N^+$—$C_{2-4}$-alkyl-, $(CH_3)_3N^+$—$C_{1-4}$-alkyl-CO—, $H_2N$—C(NH)—NH—$C_{1-6}$—NH—CO—, $C_{1-6}$-alkyl-O—CO—, $C_{1-6}$-alkyl-O—CO—$C_{1-4}$-alkyl-, $C_{1-6}$-alkyl-O—CO—$C_{1-4}$-alkyl-CO—, $C_{1-6}$-alkyl-O—CO—$C_{1-4}$-alkyl-NH—CO—, $C_{1-6}$-alkyl-O—CO—NH—$C_{1-4}$-alkyl-, $C_{1-6}$-alkyl-O—CO—NH—$C_{1-4}$-alkyl-CO—, $C_{1-6}$-alkyl-O—CO—NH—$C_{1-4}$-alkyl-NH—CO—, HOCO—$C_{1-4}$-alkyl-, HOCO—$C_{1-4}$-alkyl-CO—, HOCO—$C_{1-4}$-alkyl-NH—CO—, $H_2N$—CNH— and $H_2NC(NH)NH$—$C_{1-6}$-alkyl-CO—.

or

Also preferred $R^1$ is selected from among a group of below listed formulas (c1) to (c5):

(c1) 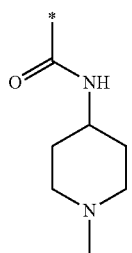

(c2) 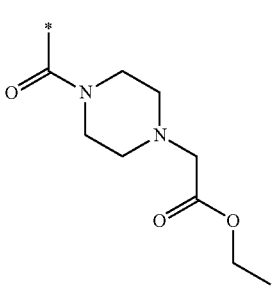

(c3) 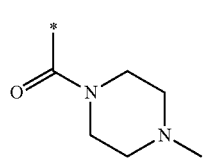

(c4) 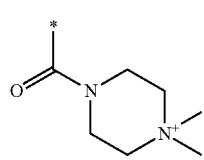

(c5) 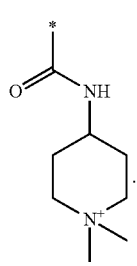

Particularly preferred $R^1$ denotes hydrogen or is selected from the group consisting of $C_{1-6}$-alkyl, $C_{1-4}$-alkyl-$SO_2$—, $C_{1-4}$-alkyl-NH—CO—, $H_2N$—CO—, $H_2N$—$C_{1-4}$-alkyl-, $H_2N$—$C_{1-4}$-alkyl-CO—, $H_2N$—$C_{1-4}$-alkyl-NH—CO—, Phenyl-CO—, Phenyl-$CH_2$—CO—, Phenyl-$CH_2$—, $C_{1-6}$-alkyl-CO—, $C_{1-6}$-alkyl-O—$C_{1-4}$-alkyl-CO—, $(CH_3)_2N$—$C_{1-4}$-alkyl-, $(CH_3)_2N$—$C_{1-4}$-alkyl-NH—CO—, $(CH_3)_3N^+$—$C_{1-4}$-alkyl-NH—CO—, $(CH_3)_3N^+$—$C_{2-4}$-alkyl-, $(CH_3)_3N^+$—$C_{1-4}$-alkyl-CO—, $H_2N$—C(NH)—NH—$C_{1-6}$—NH—CO—, $C_{1-6}$-alkyl-O—CO—, $C_{1-6}$-alkyl-O—CO—$C_{1-4}$-alkyl-, $C_{1-6}$-alkyl-O—CO—$C_{1-4}$-alkyl-CO—, $C_{1-6}$-alkyl-O—CO—$C_{1-4}$-alkyl-NH—CO—, $C_{1-6}$-alkyl-O—CO—NH—$C_{1-4}$-alkyl-, $C_{1-6}$-alkyl-O—CO—NH—$C_{1-4}$-alkyl-CO—, $C_{1-6}$-alkyl-O—CO—NH—$C_{1-4}$-alkyl-NH—CO—, HOCO—$C_{1-4}$-alkyl-, HOCO—$C_{1-4}$-alkyl-CO—, HOCO—$C_{1-4}$-alkyl-NH—CO— and $H_2N$—CNH—.

The substituent $R^{1s}$ denotes $C_{1-6}$-alkyl, preferably methyl.

$X^-$ denotes any anion forming a pharmaceutically acceptable salt, preferably selected from among $CF_3$—$COO^-$, $Cl^-$, $I^-$, $Br^-$, $HCOO^-$ and $CH_3$—$COO^-$, most preferably $Cl_-$ and $CF_3$—$COO^-$.

The substituent $R^{1b}$ is selected from the group consisting of $C_{1-4}$-alkyl,
$R^{1.4}$—$C_{2-6}$-alkyl-, optionally substituted phenyl-$CH_2$—, $R^{1.4.3}$—O—CO—$CH_2$— and HO—CO—$CH_2$—, preferably $C_{1-4}$-alkyl, particularly preferred methyl, wherein $R^{1.4}$ is selected from the group consisting of hydrogen, $R^{1.4.1}R^{1.4.2}N$—, $R^{1.4.1}R^{1.4.2}R^{1.4.3}N^+$—, $H_2N$—C(NH)—NH—, $R^{1.4.3}$—HN—C($NR^{1.4.4}$)—NH, optionally substituted phenyl, $R^{1.4.3}$—O—CO—, $R^{1.4.4}$—O—CO—HH—, HO—CO— and $HOSO_2$—, wherein $R^{1.4.1}$ denotes hydrogen or $C_{1-6}$-alkyl, preferably hydrogen or $C_{1-4}$-alkyl, $R^{1.4.2}$ denotes hydrogen or $C_{1-6}$-alkyl, preferably hydrogen or $C_{1-4}$-alkyl, $R^{1.4.3}$ denotes hydrogen or $C_{1-6}$-alkyl, preferably hydrogen or $C_{1-4}$-alkyl, most preferably $C_{1-4}$-alkyl, $R^{1.4.4}$ denotes hydrogen or $C_{1-6}$-alkyl, preferably hydrogen or $C_{1-4}$-alkyl, most preferably $C_{1-4}$-alkyl.

The symbol L denotes a bridging group —CO—NH—$C_{2-6}$-alkyl-NH—CO—, —CO$C_{1-6}$-alkyl-CO— or forming a compound of formula (IC), whereby the molecular entities of formula (IC) connected by L may be identical or different, (IC)
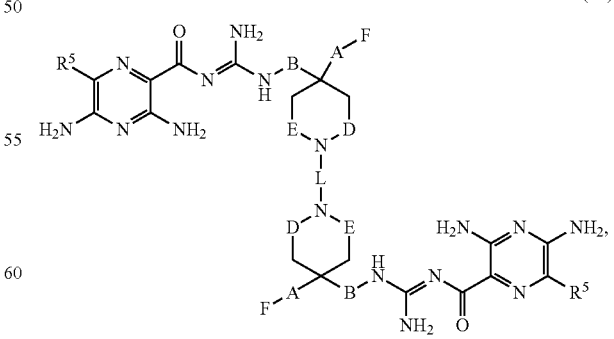

preferably forming a compound of formula (IC.1), whereby the molecular entities of formula (IC.1) connected by L may be identical or different, (IC.1)

[Chemical structure diagram showing formula IC.1 with substituents Cl, H₂N, NH₂, R², R³, R⁴, R⁶, R⁷, A, R²ᵃ, R³ᵃ, R⁴ᵃ, R⁶ᵃ, R⁷ᵃ]

The substituents $R^2$ and $R^{2a}$ independently from each other are selected from the group consisting of hydrogen, halogen, CN, $C_{1-6}$alkyl, $C_{1-3}$-alkyl-O—, $C_{1-3}$-alkyl-OCO—, —COOR$^{4.1}$, —CONR$^{4.2}$R$^{4.3}$ and —OR$^{4.1}$, preferably hydrogen, wherein
  $R^{4.1}$ denotes hydrogen or $C_{1-4}$-alkyl, preferably hydrogen or $C_{1-2}$-alkyl, particularly preferred hydrogen or methyl,
  $R^{4.2}$ denotes hydrogen or $C_{1-4}$-alkyl, preferably hydrogen or $C_{1-2}$-alkyl, particularly preferred hydrogen or methyl,
  $R^{4.3}$ denotes hydrogen or $C_{1-4}$-alkyl, preferably hydrogen or $C_{1-2}$-alkyl, particularly preferred hydrogen or methyl.

The substituents $R^3$ and $R^{3a}$ independently from each other are selected from the group consisting of hydrogen, halogen, CN, $C_{1-4}$alkyl, $C_{1-3}$-alkyl-O, —$C_{1-3}$-alkyl-OCO—, —COOR$^{4.1}$, —CONR$^{4.2}$R$^{4.3}$ and —OR$^{4.1}$, preferably hydrogen, wherein
  $R^{4.1}$ denotes hydrogen or $C_{1-4}$-alkyl, preferably hydrogen or $C_{1-2}$-alkyl, particularly preferred hydrogen or methyl,
  $R^{4.2}$ denotes hydrogen or $C_{1-4}$-alkyl, preferably hydrogen or $C_{1-2}$-alkyl, particularly preferred hydrogen or methyl,
  $R^{4.3}$ denotes hydrogen or $C_{1-4}$-alkyl, preferably hydrogen or $C_{1-2}$-alkyl, particularly preferred hydrogen or methyl.

The substituents $R^4$ and $R^{4a}$ independently from each other are selected from the group consisting of hydrogen, halogen, CN, $C_{1-3}$-alkyl-O—$C_{1-3}$-alkyl-OCO—, —COOR$^{4.1}$, —CONR$^{4.2}$R$^{4.3}$ and —OR$^{4.1}$, preferably hydrogen, wherein
  $R^{4.1}$ denotes hydrogen or $C_{1-4}$-alkyl, preferably hydrogen or $C_{1-2}$-alkyl, particularly preferred hydrogen or methyl,
  $R^{4.2}$ denotes hydrogen or $C_{1-4}$-alkyl, preferably hydrogen or $C_{1-2}$-alkyl, particularly preferred hydrogen or methyl,
  $R^{4.3}$ denotes hydrogen or $C_{1-4}$-alkyl, preferably hydrogen or $C_{1-2}$-alkyl, particularly preferred hydrogen or methyl, or $R^3$ and $R^4$ or $R^{3a}$ and $R^{4a}$ together denote —O—$C_{1-3}$-alkyl-O—; preferably —O—$C_{1-2}$-alkyl-O—.

The substituent $R^5$ denotes Cl or Br, preferably Cl.

The substituent $R^6$ and $R^{6a}$ independently from each other are selected from the group consisting of hydrogen, halogen, CN, $C_{1-4}$alkyl, $C_{1-3}$-alkyl-O—, $C_{1-3}$-alkyl-OCO—, —COOR$^{4.1}$, —CONR$^{4.2}$R$^{4.3}$ and —OR$^{4.1}$, preferably hydrogen, wherein
  $R^{4.1}$ denotes hydrogen or $C_{1-4}$-alkyl, preferably hydrogen or $C_{1-2}$-alkyl, particularly preferred hydrogen or methyl,
  $R^{4.2}$ denotes hydrogen or $C_{1-4}$-alkyl, preferably hydrogen or $C_{1-2}$-alkyl, particularly preferred hydrogen or methyl,
  $R^{4.3}$ denotes hydrogen or $C_{1-4}$-alkyl, preferably hydrogen or $C_{1-2}$-alkyl, particularly preferred hydrogen or methyl.

The substituent $R^7$ and $R^{7a}$ independently from each other are selected from the group consisting of hydrogen, halogen, CN, $C_{1-4}$alkyl, $C_{1-3}$-alkyl-O—, $C_{1-3}$-alkyl-OCO—, —COOR$^{4.1}$, —CONR$^{4.2}$R$^{4.3}$ and —OR$^{4.1}$, preferably hydrogen, wherein
  $R^{4.1}$ denotes hydrogen or $C_{1-4}$-alkyl, preferably hydrogen or $C_{1-2}$-alkyl, particularly preferred hydrogen or methyl,
  $R^{4.2}$ denotes hydrogen or $C_{1-4}$-alkyl, preferably hydrogen or $C_{1-2}$-alkyl, particularly preferred hydrogen or methyl,
  $R^{4.3}$ denotes hydrogen or $C_{1-4}$-alkyl, preferably hydrogen or $C_{1-2}$-alkyl, particularly preferred hydrogen or methyl.

Any of the definitions of $R^1$ to $R^7$ described above may be combined with each other to form an embodiment of the invention.

6. PREPARATION

The following methods are suitable for preparing compounds of general formula (IA), (IB) or (IC).

The compounds according to the invention may be obtained using methods of synthesis which are known to one skilled in the art and described in the literature of organic synthesis. General methods for functional groups protection and deprotection steps are described e.g. in: Greene, T. W. and Wuts, P. G. M. (eds.): *Protective Groups in Organic Synthesis, third edition* 1999; John Wiley and Sons, inc. Preferably the compounds are obtained analogously to the methods of preparation explained more fully hereinafter, in particular as described in the experimental section.

Compounds of general formula (I) can be prepared by reacting S-methylisothioureas of formula (II) with primary amines of formula (III) in a solvent like THF, acetonitrile or DMF or in a solvent mixture, preferably in the presence of a base, especially when the primary amine (III) is applied as an acid addition salt, preferably at between 18° C. to 90° C.

Compounds of general formula (I) can be converted into compounds of general formula (Ia) by reaction with BOC₂O in the presence of a base, preferably triethylamine, in a solvent like e.g. THF.

Compounds of general formulas (I) and (Ia) can be modified using methods of synthesis which are known to the one skilled in the art and described in the literature of organic synthesis, preferably by functional group protection or deprotection steps, or hydrogenations. Furthermore, the group $R^1$ in compounds of general formula (Ia) can be modified under conditions not compatible with the acylguanidine group present in compounds of general formula I, preferably by alkylation of tertiary amino groups to yield quaternary ammonium compounds.

Compounds of general formula (Ia) can be converted into compounds of general formula (I) by removal of the BOC moiety under standard acidic deprotection conditions.

Scheme 1:

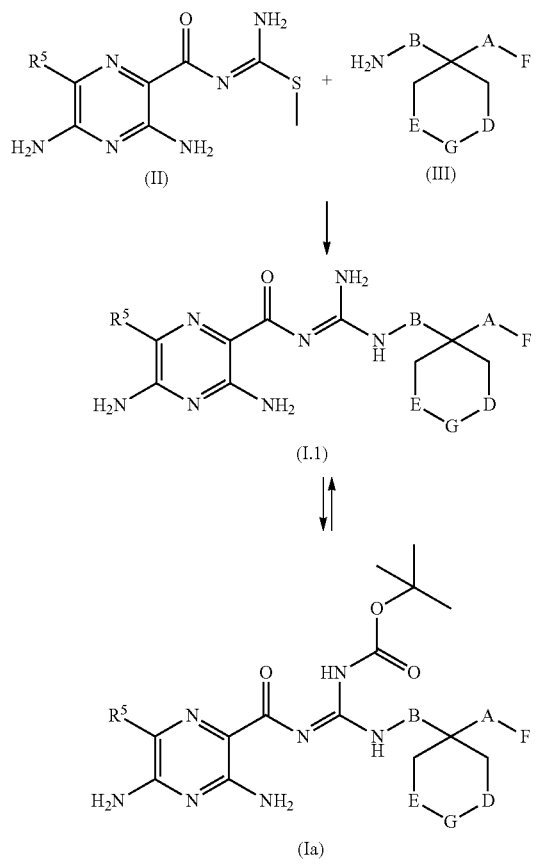

A preferred realization of Scheme 1 is Scheme 1.1.

Scheme 1.1:

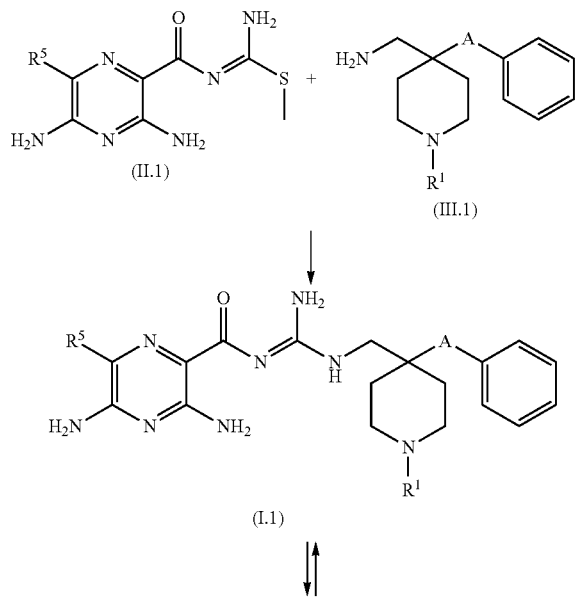

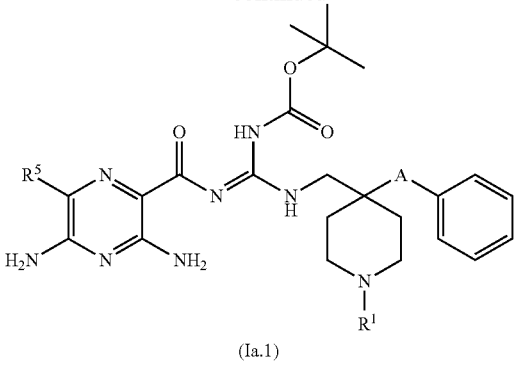

Compounds of general formula (II) can be prepared by reacting S-methylisothiourea (which may be generated in situ from its salt by addition of base) with a 1-(tert-butylcarbamoyl)prop1-en-2-yl carboxylate of general formula (IV) in a solvent like DCM, THF or a mixture of these solvents, preferably at between −10° C. to 25° C.

Compounds of general formula (IV) can be prepared from the respective carboxylic acid of general formula (V) and a 2-tert-butyl-5-methyl-isoxazolium salt of general formula (VI), which can be applied as an isolated salt (e.g. the hexafluorophosphate salt; $X=PF_6$) or generated in situ from tert-butanol, 5-methylisoxazole and trifluoromethanesulfonic acid. The latter reaction is preferably performed in a solvent like DMF or in a solvent mixture with the addition of triethylamine or another base, preferably while cooling to 0-10° C.

Scheme 2:

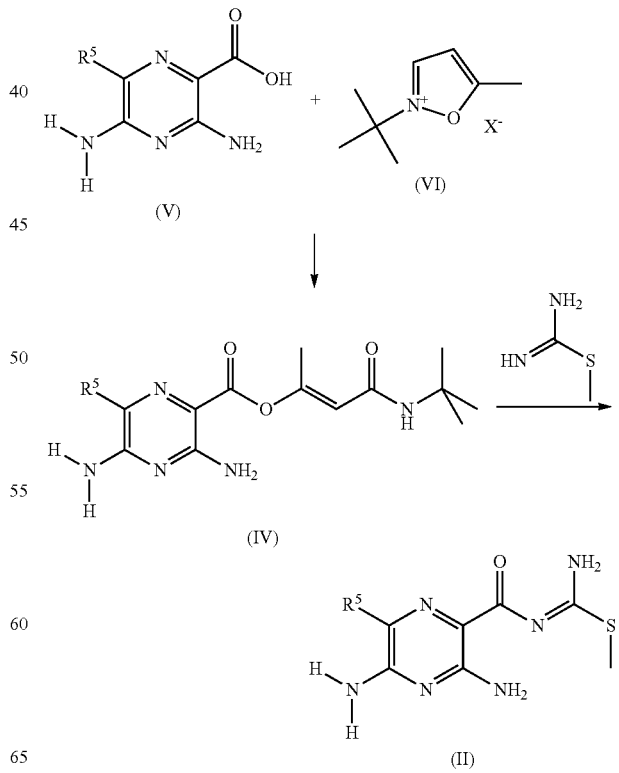

Compounds of general formula (III) can be obtained from compounds of general formula (XV) by reduction of the nitrile group, preferably by hydrogenation with raney-nickel as catalyst under hydrogen pressure in the presence of excess ammonia in a solvent like e.g. methanol. The group $R^c$ in compounds of general formula (XV) can be modified using methods of synthesis which are known to the one skilled in the art and described in the literature of organic synthesis, preferably by functional group protection or deprotection steps, esterifications, amidations, or hydrogenations. Depending on the nature of $R^c$, this moiety can be removed using methods of synthesis which are known to the one skilled in the art and described in the literature of organic synthesis, especially of protective group removal to yield compounds of general formula (XVI). Compounds of general formula (XVI) can be converted into compounds of general formula (XV) using methods of synthesis which are known to the is one skilled in the art and described in the literature of organic synthesis, especially by acylation, alkylation, or reductive amination.

Compounds of general formula (XV), wherein D represents —CH$_2$— or —CH$_2$—CH$_2$— can be prepared by reaction of alkylating agents of general formula (VI) with 4-cyanopiperidines of general formula (VII) in a solvent like THF, wherein the compound of general formula (VII) is deprotonated by a base, preferably LDA, n-BuLi or NaH, preferably at a temperature between −80° C. and 0° C. and wherein LG represents a leaving group, preferably Cl, Br, I, mesylate or tosylate and wherein G represents an acyl moiety, preferably the BOC group.

Compounds of general formula (XV), wherein A represents a bond can be prepared by double alkylation of phenylacetonitriles of general formula (IX) with bis-chloroethylamines of general formula (VIII) with the addition of a base, preferably NaH in a solvent, preferably DMF, wherein $R^c$ represents an acyl moiety, preferably the BOC group.

Scheme 3:

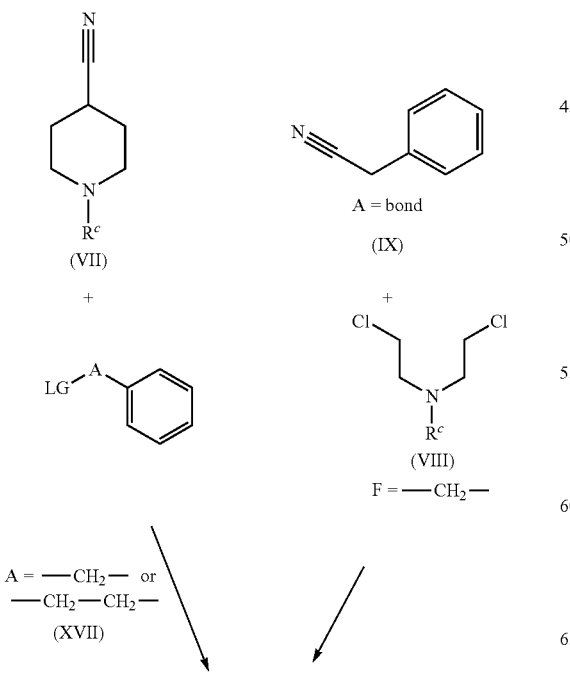

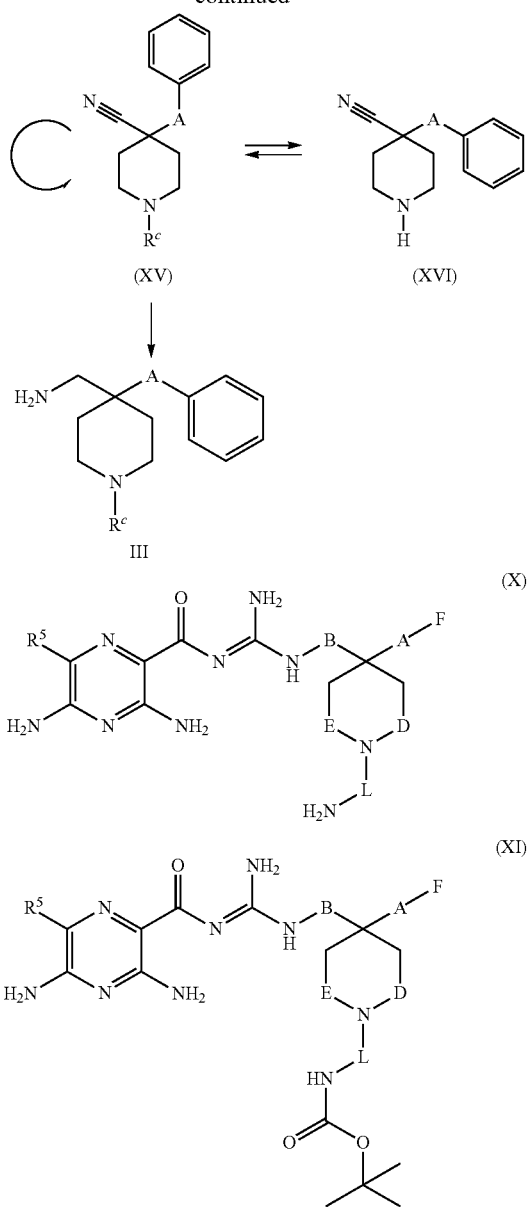

Compounds of general formula (X), wherein L represents chain with at least 2 carbon atoms, can be prepared by reaction of (XI) with an acid preferably TFA or HCl in a solvent like THF, dioxane, dichloromethane, DMF or water, preferably at a temperature between 10° C. and 50° C.

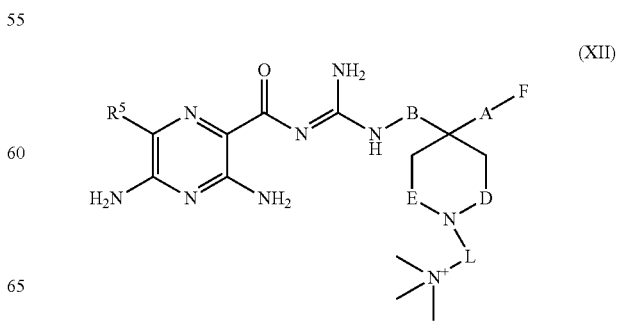

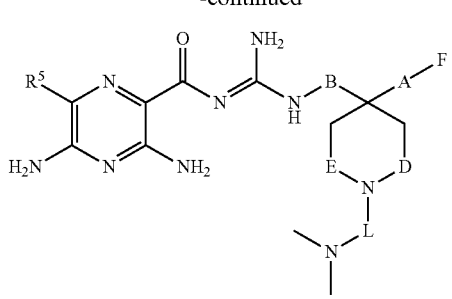

(XIII)

Compounds of general formula (XII), wherein L represents chain with at least 2 carbon atoms can be prepared by a reaction sequence starting with (XIII) protecting it with BOC anhydride, quaternization with alkylhalogenide preferably alkyliodide in a solvent like acetone, THF, dioxane or dichloromethane, preferably at a temperature between 10° C. and 50° C. followed by deprotection with acids.

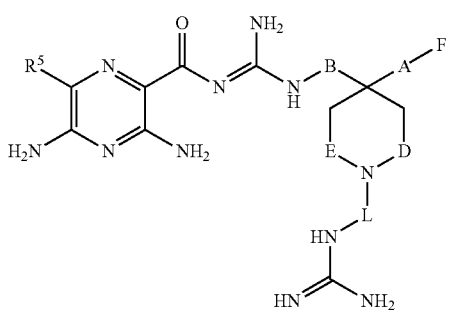

(XIV)

Compounds of general formula (XIV), wherein L represents chain with at least 2 carbon atoms can be prepared by reaction compounds of general formule (X) with 1H-1.2.4-triazole-1-carboxamidine or S-methylisothioureas in DMF preferably at a temperature between 50° C. and 90° C.

7. EXAMPLES 7.1 Synthesis of Intermediates

Intermediate A.61

3,5-Diamino-6-chloropyrazine-2-carboxylic acid

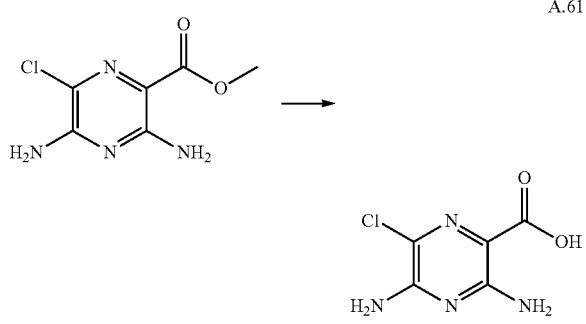

A.61

A mixture of methyl 3,5-diamino-6-chloropyrazine-2-carboxylate (100 g; 494 mmol), methanol (1 l) and NaOH (6 mol/l in water; 240 mL; 1.44 mol) is refluxed for 3 h. The mixture is allowed to cool to r.t. and then neutralized by addition of hydrochloric acid (6 mol/l in water; approx. 240 mL). Water (200 mL) is added. The precipitate formed is filtered off with suction, washed with water and dried at 60° C.

Yield: 99.6 g (107% of theory)

$C_5H_5ClN_4O_2$ ESI Mass spectrum: m/z=189 [M+H]+; m/z=187 [M−H]−

Intermediate A.62

3,5-Diamino-6-bromopyrazine-2-carboxylic acid is prepared from methyl 3,5-diamino-6-bromopyrazine-2-carboxylate (which is prepared from methyl 3,5-diamino-6-chloropyrazine-2-carboxylate as described in J. Med. Chem. 1967, 10, 66-75) analogously to the procedure described for the synthesis of intermediate A.61

Intermediate B.61

1-(tert-Butylcarbamoyl)prop-1-en-2-yl 3,5-diamino-6-chloropyrazine-2-carboxylate

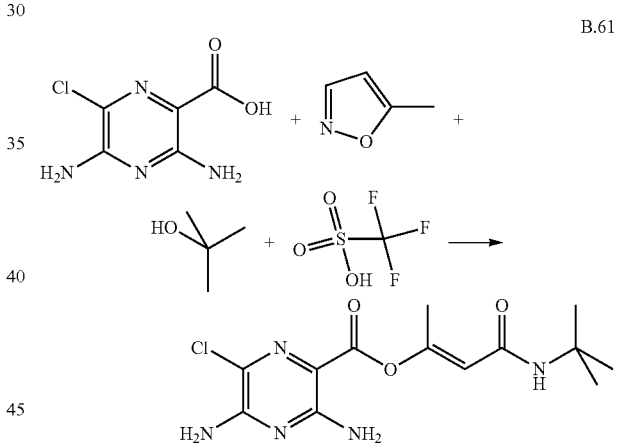

B.61

Stage 1:

A mixture of tert-butanol (21.0 mL; 226 mmol) and 5-methylisoxazole (18.0 mL; 221 mmol) is cooled with an ice-bath. Trifluoromethanesulfonic acid (20.0 mL; 221 mmol) is added dropwise with continued cooling. The resulting mixture is stirred for 1 h without further cooling.

Stage 2:

To a solution or suspension of 3,5-diamino-6-chloropyrazine-2-carboxylic acid (Intermediate A.61; 14.0 g; 74.2 mmol) and triethylamine (31.0 mL; 222 mmol) in DMF (100 mL) is added is the mixture prepared in stage 1. The resulting mixture is stirred for 4 h at r.t. Ice-water is added with stirring. The precipitate formed is filtered off with suction, washed with water and dried at 65° C. to yield the title compound.

Yield: 18.2 g (75% of theory)

$C_{13}H_{18}ClN_5O_3$ ESI Mass spectrum: m/z=328 [M+H]+; m/z=326 [M−H]−

TLC (Silica; DCM/MeOH 9:1): $R_f$=0.4

Intermediate B.62

1-(2-Methyl-2-butyl-carbamoyl)prop-1-en-2-yl 3,5-diamino-6-bromopyrazine-2-carboxylate

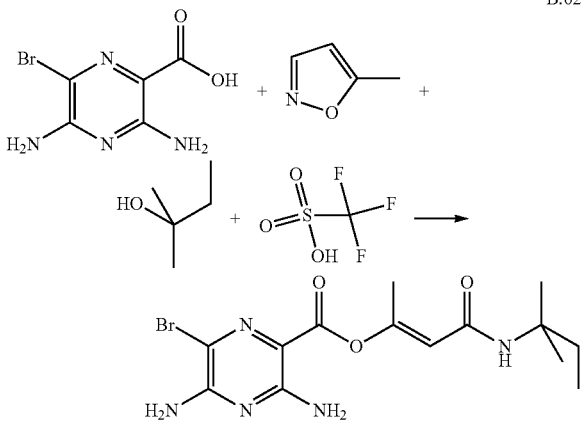

B.62

Stage 1:

A mixture of 2-methyl-2-butanol (5.75 mL; 51 mmol) and 5-methylisoxazole (4.42 mL; 51 mmol) is cooled with an ice-bath. Trifluoromethanesulfonic acid (4.84 mL; 54 mmol) is added dropwise with continued cooling. The resulting mixture is stirred over night without further cooling.

Stage 2:

To a solution or suspension of 3,5-diamino-6-bromopyrazine-2-carboxylic acid (Intermediate A.62; 5.00 g; 21.5 mmol) and triethylamine (7.48 mL; 54 mmol) in DMF (50 mL) cooled with an ice-bath is added dropwise the mixture prepared in stage 1. The resulting mixture is stirred for 4 h at r.t., then poured on ice-water. The precipitate formed is filtered off with suction, washed with water and dried at 50° C. to yield the title compound.

Yield: 7.53 g (91% of theory)

$C_{14}H_{20}BrN_5O_3$ ESI Mass spectrum: m/z=386 [M+H]+; m/z=384 [M−H]−

Intermediate C.61

3,5-Diamino-6-chloro-N-[(methylsulfanyl)methanimidoyl]pyrazine-2-carboxamide

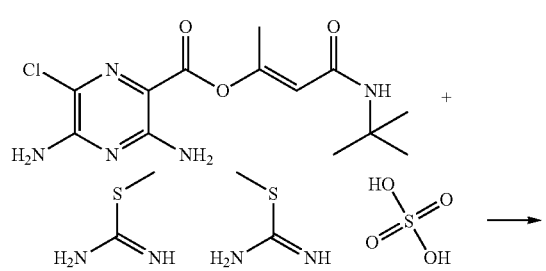

C.61

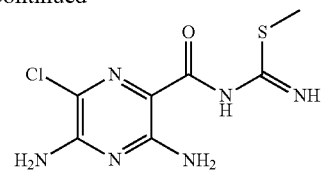

To NaOH (1 mol/l in water; 9.2 mL; 9.2 mmol) is added S-methylisothiourea sulfate (1.78 g; 6.1 mmol. The mixture is stirred until complete solution is achieved. TBME/THF (1:1; 30 mL) and then 1-(tert-butylcarbamoyl)prop-1-en-2-yl 3,5-diamino-6-chloropyrazine-2-carboxylate (Intermediate B.61; 2.00 g; 6.10 mmol) are added and the mixture is stirred at r.t. over night, then water (6 mL) is added. The precipitate formed is filtered off with suction, washed successively with water, methanol and then with diethyl ether and then dried at 50° C. to yield the title compound.

Yield: 1.33 g (84% of theory)

$C_7H_9ClN_6OS$ ESI Mass spectrum: m/z=261 [M+H]+; m/z=259 [M−H]−

Intermediate C.62

3,5-Diamino-6-bromo-N-[(methylsulfanyl)methanimidoyl]pyrazine-2-carboxamide

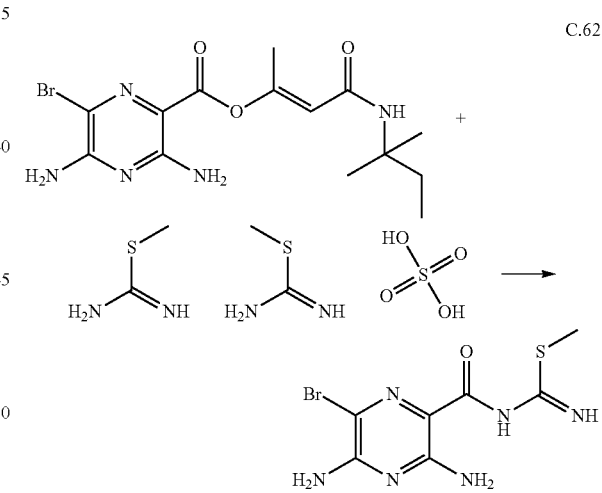

C.62

To NaOH (1 mol/l in water; 30 mL; 30 mmol) is added S-methylisothiourea sulfate (5.42 g; 19.5 mmol. The mixture is stirred until complete solution is achieved. TBME/THF (1:1; 100 mL) and then 1-(2-methyl-2-butyl-carbamoyl)prop-1-en-2-yl 3,5-diamino-6-bromopyrazine-2-carboxylate (Intermediate B.62; 7.52 g; 19.5 mmol) are added and the mixture is stirred at r.t. over night, then water (100 mL) is added. The precipitate formed is filtered off with suction, washed with THF/water (1:2) and then dried at 50° C. to yield the title compound.

Yield: 5.44 g (92% of theory)

$C_7H_9BrN_6OS$ ESI Mass spectrum: m/z=305 [M+H]+

D.2

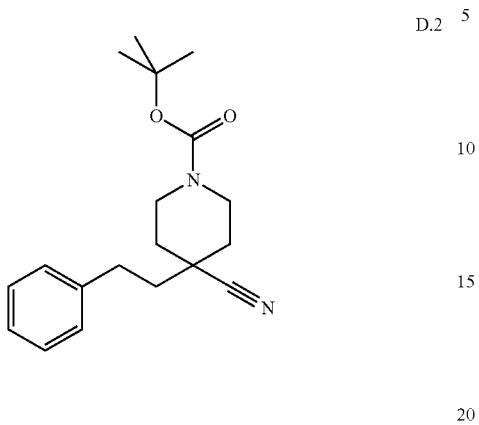

To a solution of 21.10 g di-isopropylamine in 300 mL anhydrous THF is added 83.7 mL 2.5 M solution of n-butyl lithium in THF dropwise at −78° C. The resultant solution is stirred at this temperature for 30 min. Then a solution of 40.00 g 1-N—BOC-4-cyanopiperidine in 300 mL THF is added dropwise. After 1 h stirring 51.99 ml (2-bromo-ethyl)-benzene is added dropwise. After the addition the reaction mixture is allowed to warm up to room temperature and stirred overnight. 100 mL water is added to quench the reaction. THF is removed to leave a slurry which is partitioned between ethyl acetate and water. After a separation the organic layer is washed with sat. aq. NH$_4$Cl and brine, dried with Na$_2$SO$_4$ and concentrated under reduced pressure. Purification by column chromatography results in 57.23 g of intermediate D.2. TLC (EA/PE 1/8) R$_f$:0.4.

D.8

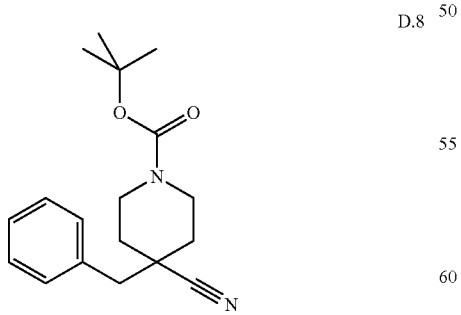

Intermediate D.8 is obtained using a similar procedure as described for intermediate D.2 utilizing benzyl bromide as alkylating agent. TLC (ethylacetate (EA)/petroleum ether (PE)) 1/9) R$_f$: 0.3.

C.17

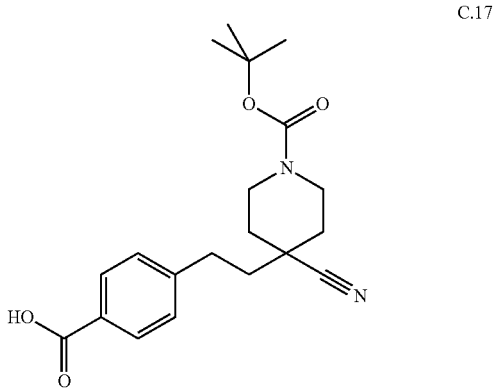 [SMILES: CC(C)(C)OC(=O)N1CCC(C#N)(CCc2ccc(C(=O)O)cc2)CC1]

Intermediate C.17 is obtained using a similar procedure as described for intermediate D.2 using 4-(2-bromoethyl)benzoic acid as alkylating agent. TLC (MeOH/dichloromethane (DCM) 5/95) R$_f$: 0.4.

C.18

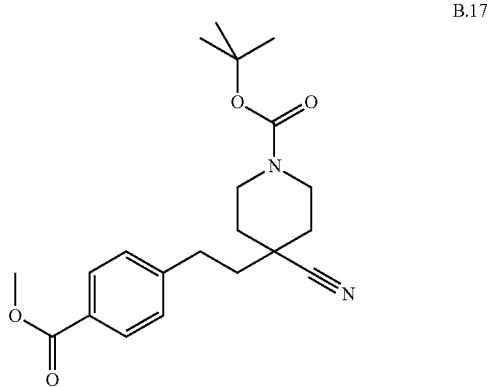 [SMILES: COC(=O)c1ccc(CCC2(C#N)CCN(C(=O)OC(C)(C)C)CC2)cc1]

Intermediate C.18 is obtained treating C.17 with ammonia and TBTU in dichloromethane.

B.17

To a solution of 4.00 g intermediate C.17 in 40 ml dry DMF are added 5.40 g K$_2$CO$_3$ and then 2.40 ml methyl iodide dropwise. The reaction mixture is stirred at room temperature for 12 h. Then water is added and the mixture is extracted with diethyl ether. The organic phases are is pooled, dried over Na$_2$SO$_4$ and evaporated. The resulting crude product is purified by FC resulting in 3.40 g of intermediate B.17. TLC (EA/PE 2/3) R$_f$: 0.6.

D.45

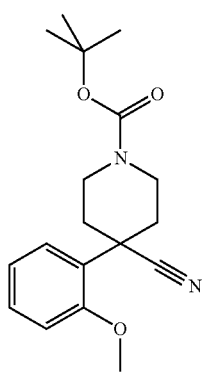

D.45

To a solution of 2.00 g N—BOC—N,N-bis(2-chloroethyl)amine and 1.10 g (2-methoxyphenyl)-acetonitrile in 15 ml THF and 5 ml DMF is added 0.78 g of NaH in portions at r.t. and the mixture is stirred at 55° C. for 16 h. The reaction is quenched by addition of cold water and extracted with ethyl acetate. The organic layer is washed with brine and water, dried over Na$_2$SO$_4$ filtered and evaporated under reduced pressure. The crude solid is triturated with a mixture of CHCl$_3$ and ether filtered and dried resulting in 1.0 g of intermediate D.45. TLC (EA:PE 3/7) R$_f$: 0.6.

D.43 and D.44

D.43 and D.44 are obtained using a similar procedure as described for intermediate D.45 utilizing the corresponding benzyl cyanides.

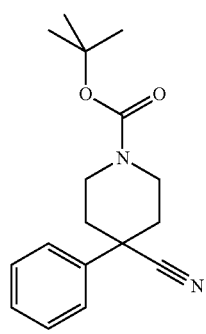

D.43

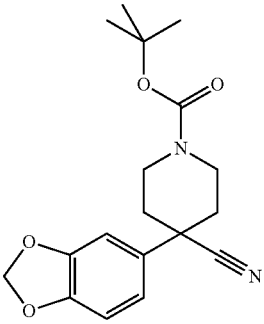

D.44

C.2

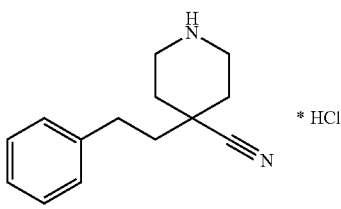

C.2

A mixture of 2.50 g of piperidine D.2 and 40 ml 25% TFA in dichloromethane are stirred for 1.5 h at room temperature. The solvent is evaporated, methanolic hydrochloric acid is added and the solvent evaporated again giving rise to 2.53 g of intermediate C.2.

ESI-MS m/z: 215. The corresponding TFA salt of C.2 is obtained by purification of the crude product by preparative reversed-phase HPLC with TFA as modifier.

C.8, C.43, C.44 and C.45

The following intermediates are obtained using a similar procedure as described for intermediate C.2 with a modified workup: neutralization of the reaction mixture with saturated NaH—CO$_3$ solution followed by an aqueous workup.

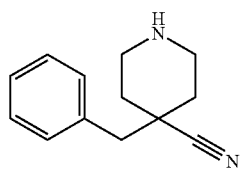

C.8

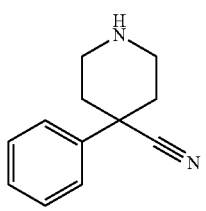

C.43

-continued

C.44
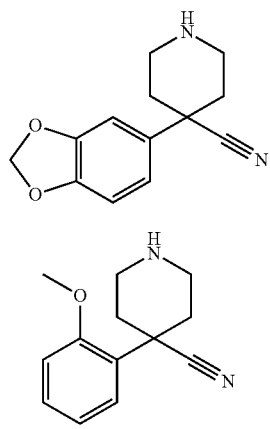

C.45
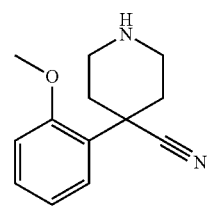

B.2
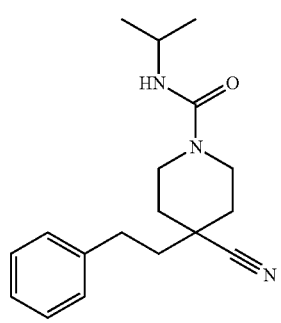

A mixture of 2.30 g piperidine hydrochloride C.2, 1.08 ml 2-isocyanato-propane, 1.99 ml triethylamine and 50 ml THF are stirred at 50° C. for 2 h. The reaction mixture is concentrated under reduced pressure and water is added and finally extracted with dichloromethane. The combined organic phases are dried over MgSO$_4$ and evaporated yielding 1.65 g of intermediate B.2.

ESI-MS m/z: 300, 344

B.4, B.8, B.12, B.18, B.19, B.43, B.44, B.45, B.48 and B.49

The following intermediates are obtained using a similar procedure as described for intermediate B.2 utilizing the corresponding isocyanates. DCM can be used as an alternative solvent.

B.4
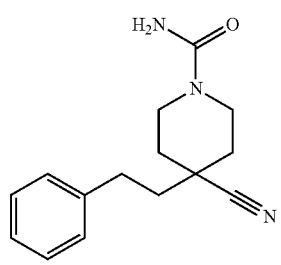

-continued

B.8
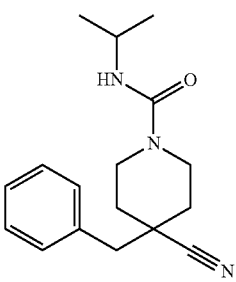

B.12
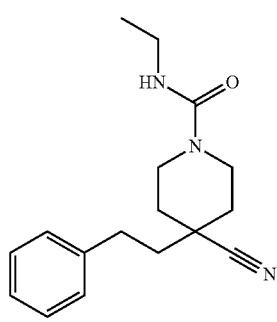

B.18
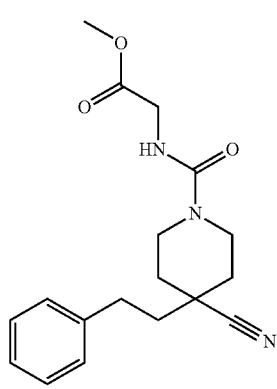

B.19
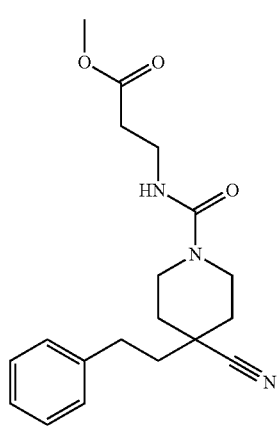

B.43

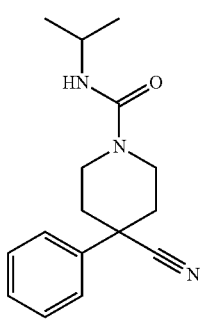

B.44

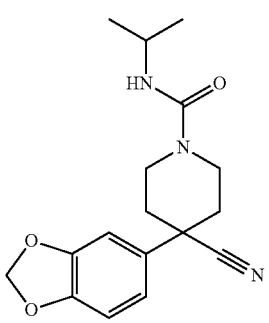

B.45

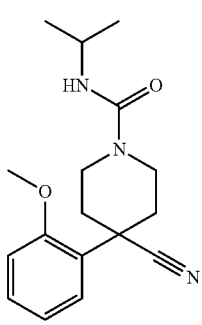

B.48

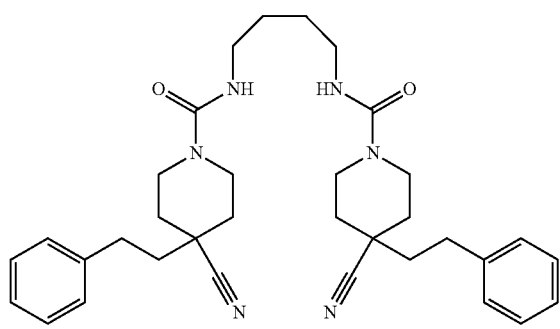

B.49

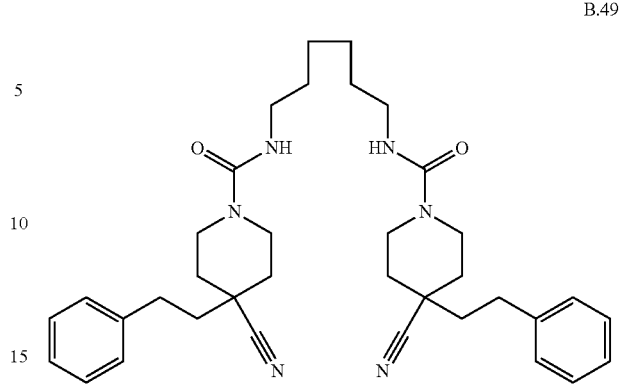

B.10

B.10

0.22 ml Triethylamine is added slowly to a mixture of 0.34 g piperidine trifluoroacetate C.2, 0.32 g triphosgene and 5 ml dichloromethane. The mixture is stirred at room temperature for 4 h and 0.17 ml N,N-dimethyl-ethylendiamine are added and the reaction mixture is stirred at room temperature overnight. The reaction mixture is concentrated under reduced pressure, a mixture of DMF, methanol and TFA is added, and the resulting mixture is filtered and purified by preparative reversed-phase HPLC. The product-containing fractions are pooled and evaporated. The resulting residue is taken up with dichloromethane and a 4N NaOH solution is added. The organic phase is separated by a phase separator cartridge. Evaporation gives rise to 0.22 g of intermediate B.10. ESI-MS m/z: 329.

B.33 B.34 B.39 B.35 B.36 B.38 B.40, B.51, B.52, B.53, B.54, B.55 and B.56

The following intermediates are obtained using a similar procedure as described for intermediate B.10 using the corresponding amines.

B.33 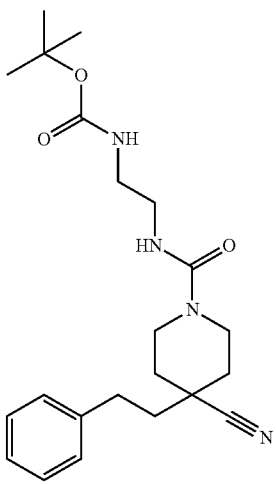
B.35 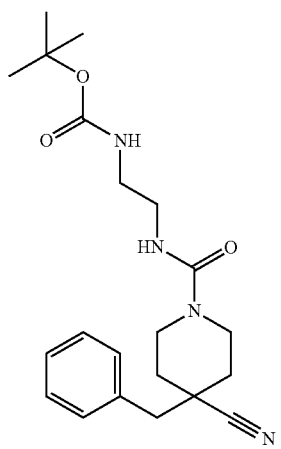
B.34 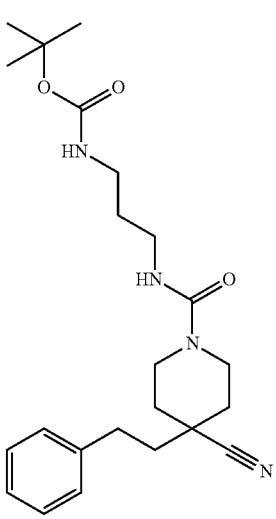
B.36 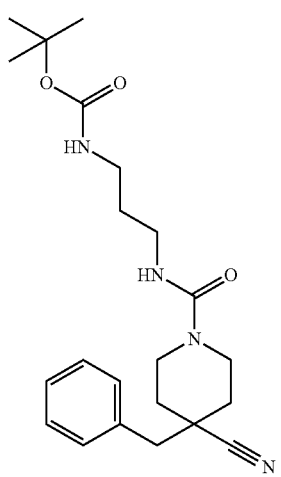
B.38 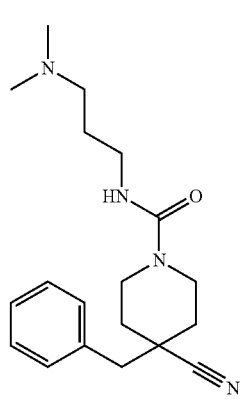
B.39 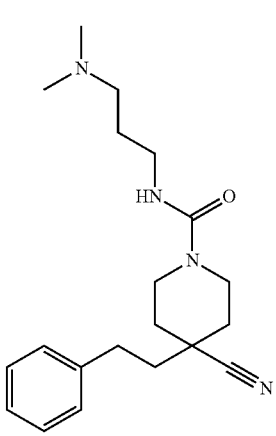
B.40

B.51

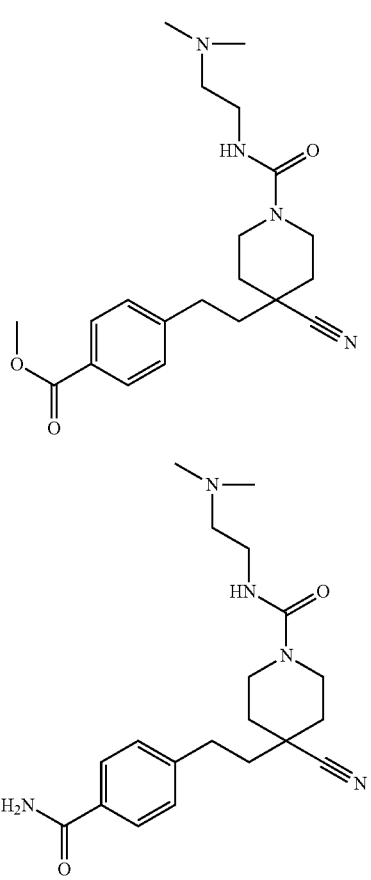

B.52

B.53

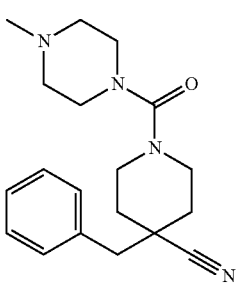

B.53

To a suspension of 0.75 g of 1,1'-carbonyldi(1,2,4-triazole) in 5 ml of THF, a solution of 0.5 ml of 1-methylpiperazine dissolved in 5 ml of THF is added dropwise. The reaction mixture is stirred at room temperature for 40 minutes, then a solution of 0.5 g of intermediate C.2 (as free base) in 5 ml of THF is added dropwise and the reaction mixture is stirred at 60° C. overnight. The solvent is evaporated, the crude product obtained is partitioned between dichloromethane and water and the organic phase is separated, dried over sodium sulfate and concentrated under vacuum. The crude product is purified by flash chromatography (eluent: AcOEt/MeOH=80/20) and re-purified by preparative LC-MS (reverse phase; NH₄COOH) 150 mg of intermediate B.53 are obtained.

B.54 and B.55

The following intermediates are obtained using a similar procedure as described for intermediate B.53 using the corresponding amines

B.54

B.55

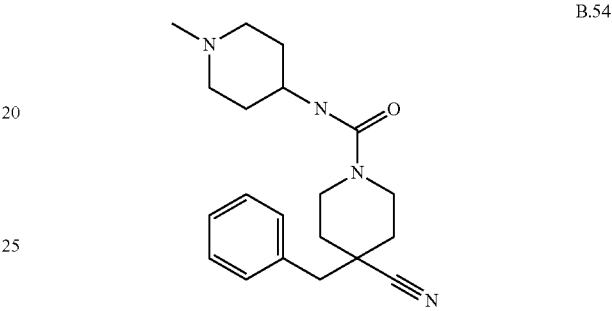

B.56

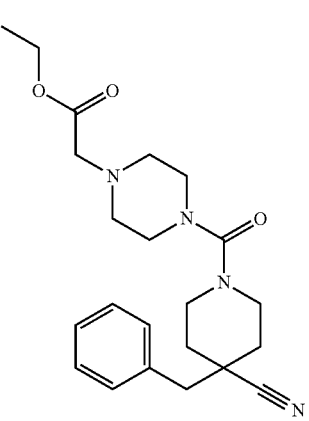

B.56

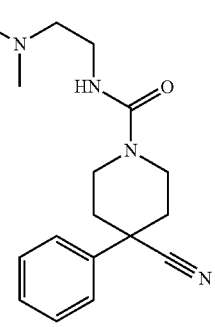

B.56 is prepared following a similar procedure as in the preparation of B.53 starting from commercially available 4-cyano-4-phenylpiperidine and N,N-dimethylethylenediamine.

B.3

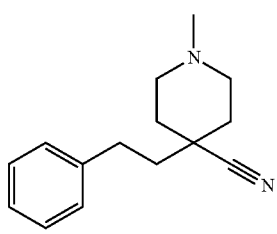

Intermediate B.3 is prepared by reductive amination of intermediate C.2 with formaldehyde and NaCNBH$_3$ in THF.

B.7 and B.21

The following intermediates are obtained using a similar procedure as described for intermediate B.3 utilizing the corresponding carbonyl compounds.

B.7

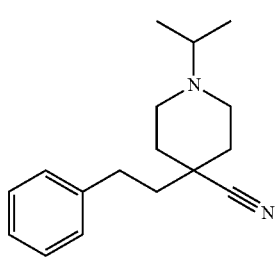

B.21

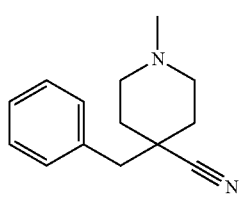

B.5

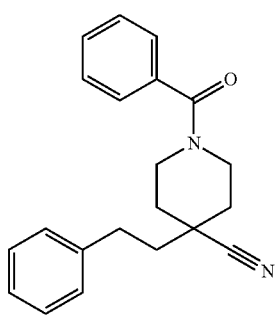

Intermediate B.5 is prepared by acylation of intermediate C.2 with benzoyl chloride and triethylamine in dichloromethane.

B.1, B.11, B.13, B.14, B.9, B.20 and B.47

The following intermediates are obtained using a similar procedure as described for intermediate B.5 using the corresponding acid chlorides.

B.1

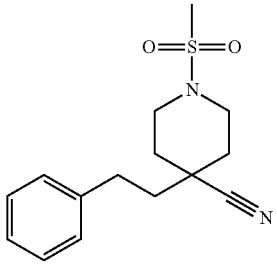

B.11

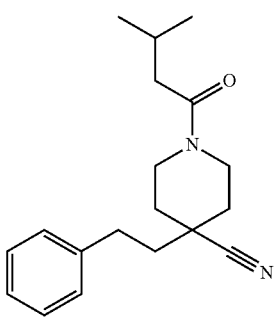

B.13

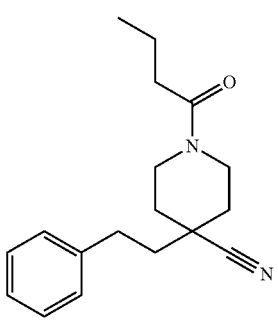

B.14

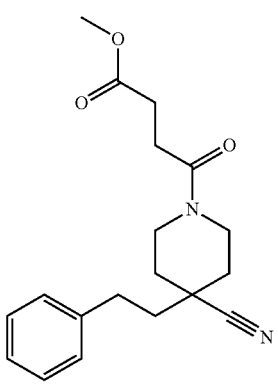

-continued

B.9
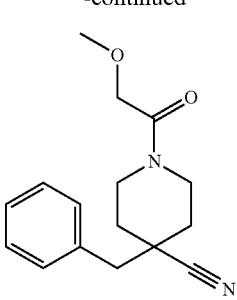

B.20
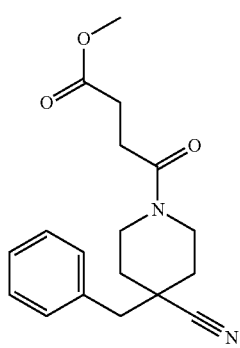

B.47
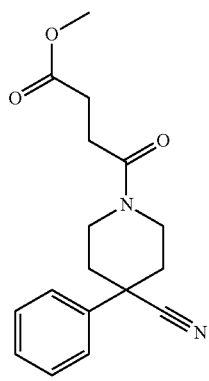

B.22

B.22
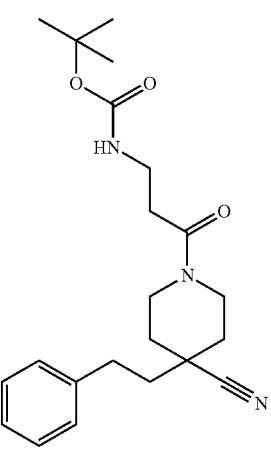

To a mixture of 1.07 g intermediate C.2, 1.42 g N—BOC-beta alanine, 2.5 g EDCI in 50 ml anhydrous THF is added 4.90 ml triethylamine and 0.1 g DMAP. The reaction mixture is stirred at r.t. overnight. Water is added and the mixture concentrated and extracted with ethyl acetate. The combined organic phases are washed with sat. aq. $NH_4Cl$ and brine, dried over $Na_2SO_4$ and concentrated. The residual crude product is purified by FC giving rise to intermediate B.22

B.23, B.25, B.24, B.26, B.27 and B.42

The following intermediates are obtained using a similar procedure as described for intermediate B.22 using the corresponding acids.

B.23
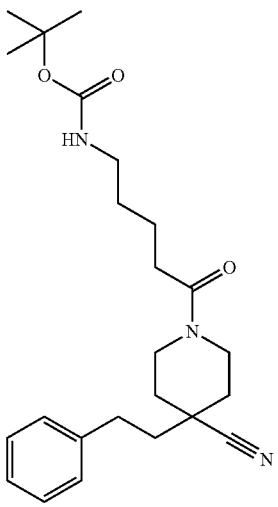

B.25
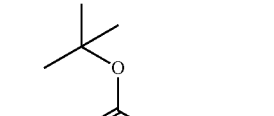

B.24
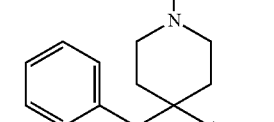

53
-continued

B.26
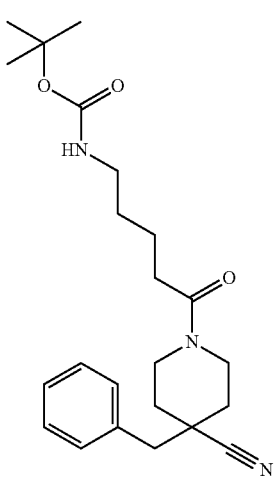

B.27
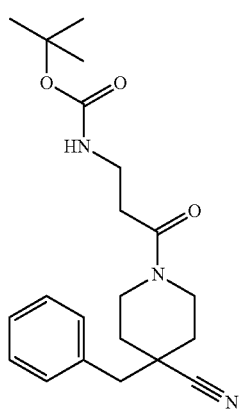

B.42
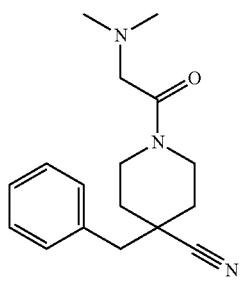

B.6
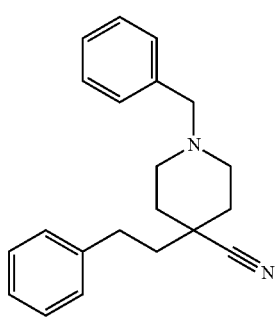

54

Intermediate B.6 is prepared by alkylation of intermediate C.2 with benzyl bromide and $Cs_2CO_3$ in acetonitrile.

B.15

The intermediate B.15 was obtained using the following procedure.

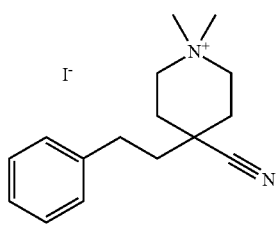
B.15

0.1 g C.2 was dissolved in 5 ml acetone and 0.1 g $K_2CO_3$ followed by drop wise addition of methyl iodide at room temperature. The resulting reaction mixture was stirred for 16 hours. Then the reaction mixture was diluted with ethyl acetate, washed with water followed by brine. The organic layer was dried over $Na_2So_4$ and concentrated under reduced pressure. The crude product was purified by chromatography eluting with 18% ethyl acetate/petroleum ether on a silica gel column

B.50

The following intermediates are obtained using a similar procedure as described for intermediate B.15 using methyl iodide.

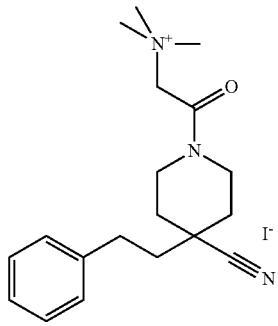
B.50

B.16, B.28, B.29, B.30, B.31, B.32, B.37, B.41 and B.46

The following intermediates are obtained using a similar procedure as described for intermediate B.6 using the corresponding alkyl halides as alkylating agents, $K_2CO_3$ and acetone.

B.16

B.28

B.29

B.32

B.30

B.31

B.37

B.41

-continued

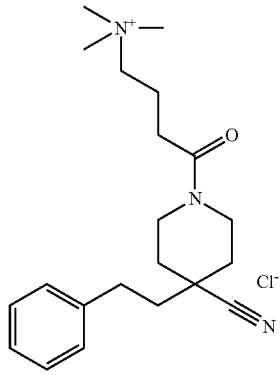

B.46

Starting material:
3-Carboxy-propyl-trimethyl-ammonium chloride

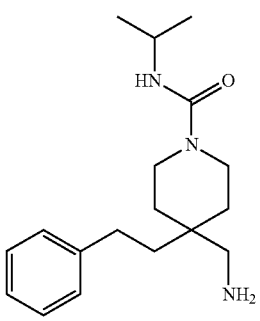

A.2

A.2

A suspension of 1.83 g of nitrile B.2, 0.40 g Raney-Nickel and 40 ml of a methanolic solution of ammonia are hydrogenated at room temperature and 3 bar $H_2$ for 23 h. In case of incomplete conversion additional catalyst and solvent are added and hydrogenation is continued for 5 h at 50° C. The catalyst is removed by filtration and the filtrate evaporated giving rise to 1.95 g of intermediate A.2. ESI-MS m/z: 304

A.1, A.3, A.4, A.5, A.6, A.7, A.10, A.11, A.12, A.13, A.14, A.15, A.16, A.17, A.18, A.19, A.22, A.23, A.25, A.28, A.29, A.32, A.33, A.34, A.39, A.48, A.51, A.52, A.53, A.54, A.55, A.56 and A.57

The following intermediates are obtained from the corresponding nitriles using a similar procedure as described for intermediate A.2.

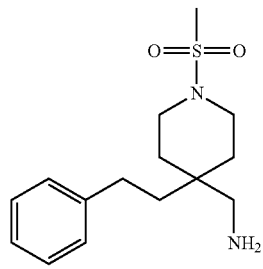

A.1

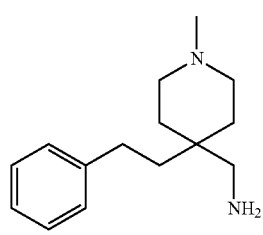

A.3

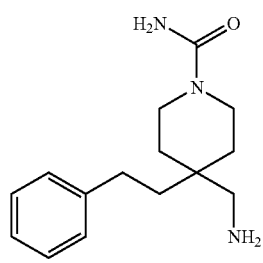

A.4

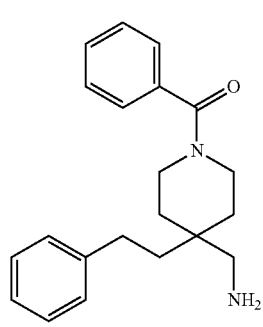

A.5

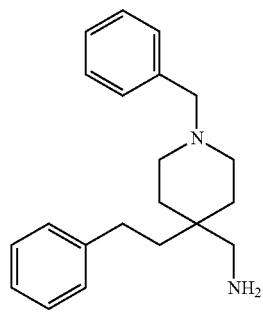

A.6

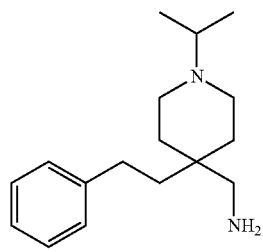

A.7

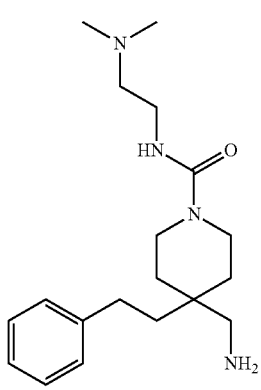 A.10
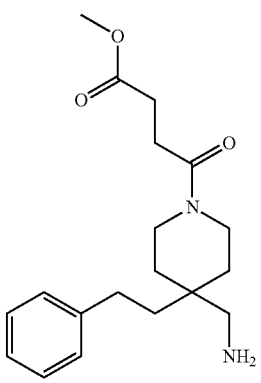 A.14
A.11
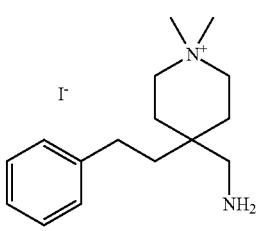 A.15
A.12
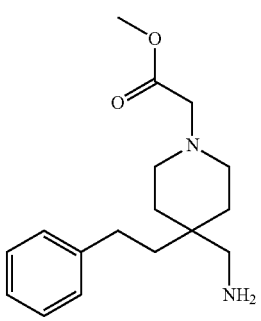 A.16
A.13
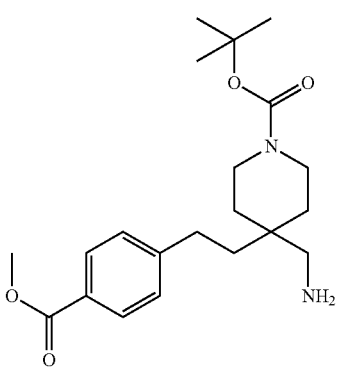 A.17

A.18
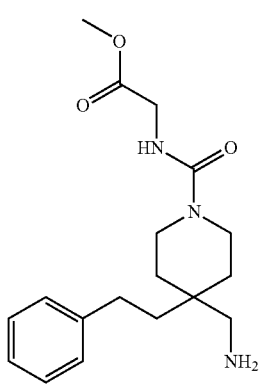
A.19
A.57
A.58
A.22
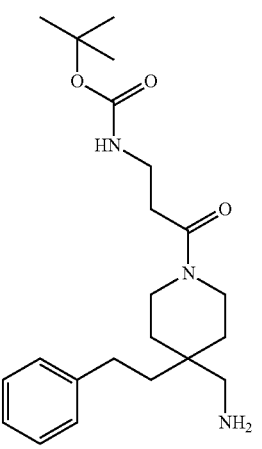
A.23
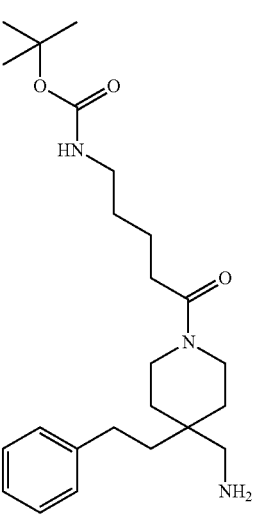
A.25
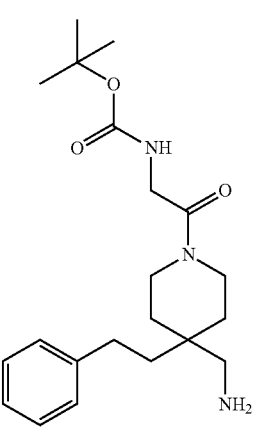

A.28
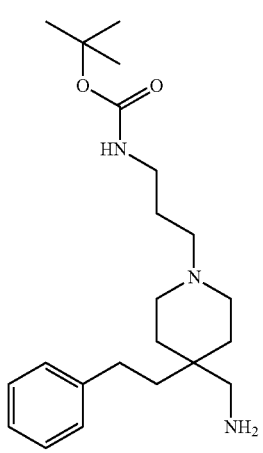
A.29
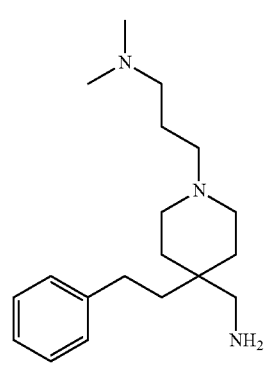
A.32
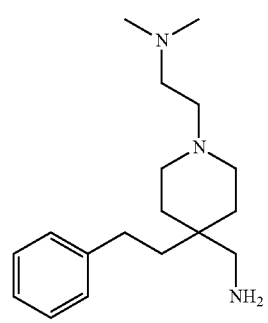
A.33
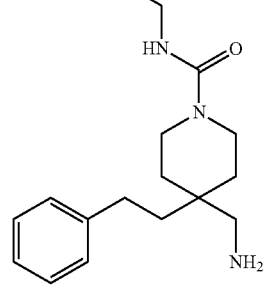
A.34
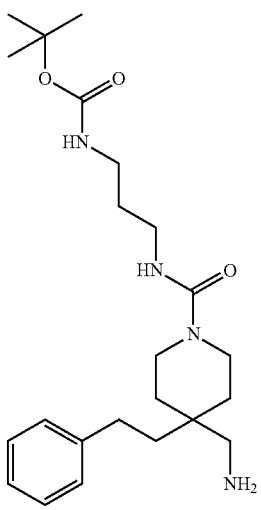
A.39
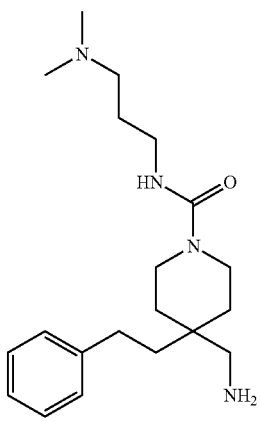
A.48
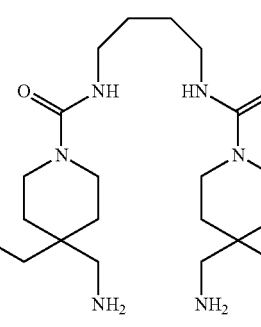
A.49
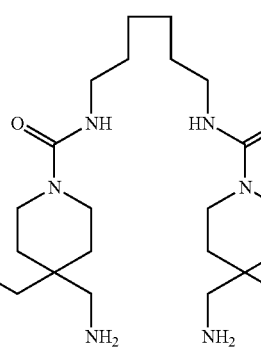

-continued
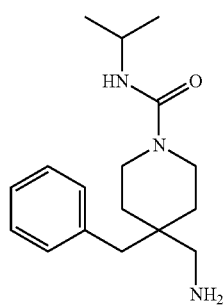
A.8
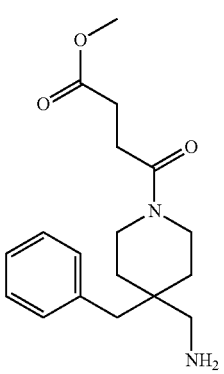
A.9
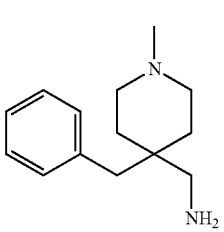
A.20
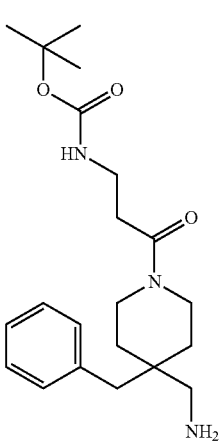
A.21
A.24
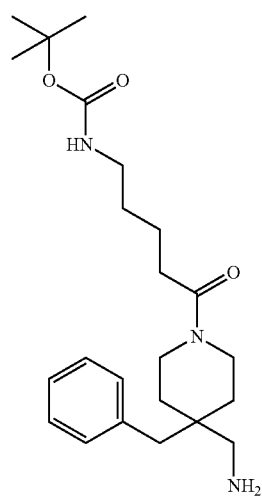
A.26
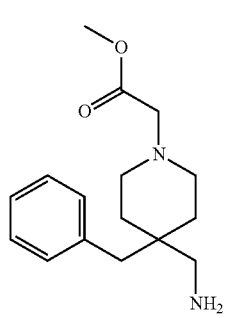
A.27
A.30
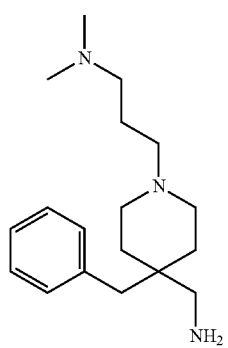
A.31

A.35
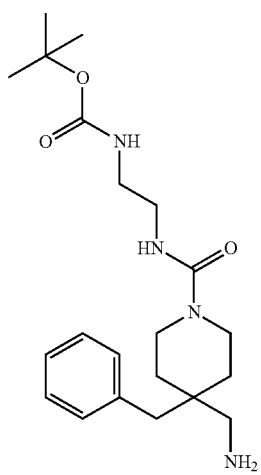
A.36
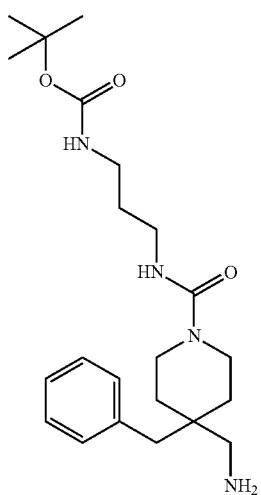
A.37
A.38
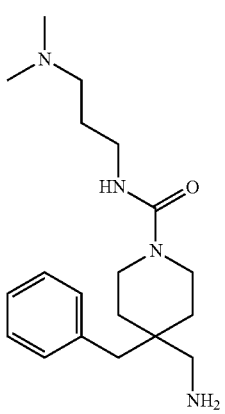
A.40
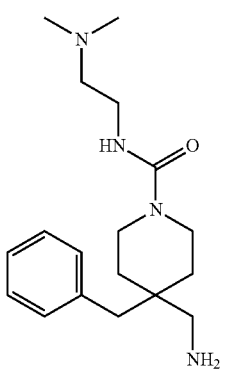
A.41
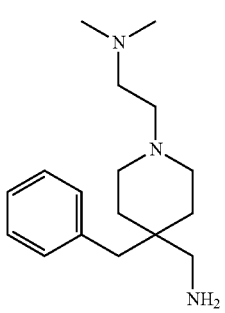
A.46
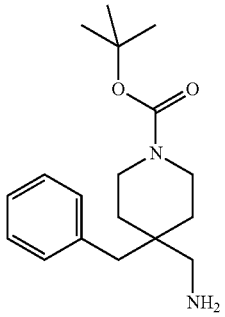

-continued

A.42

A.43

A.44

A.45

-continued

A.47

A.55

A.50

A.51

A.52

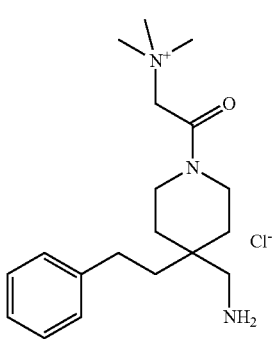

A.53

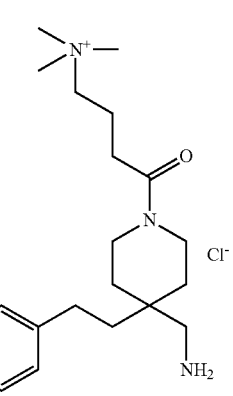

(Starting material: B.46)

A.54

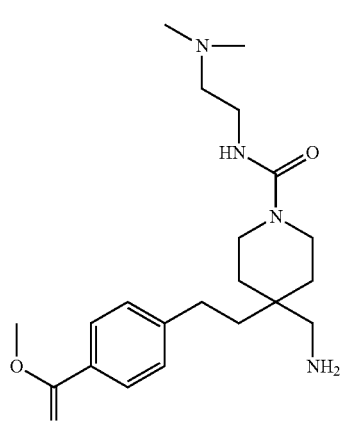

(Starting material: B.51)

A.56

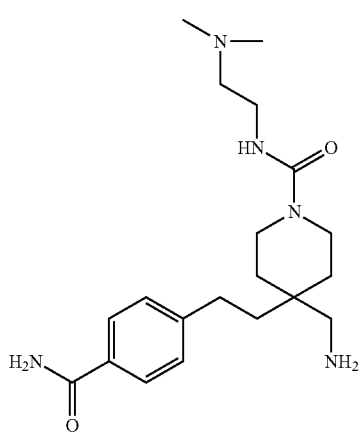

(Starting material: B.52)

A.59

A.59

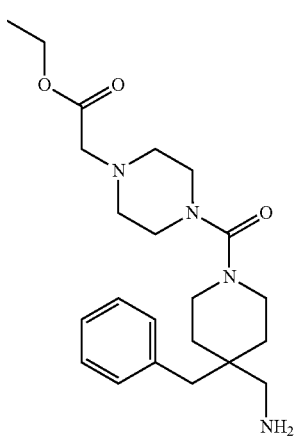

To a solution of 50 mg of intermediate B.55 in 3 ml of THF, 0.1 ml of borane tetrahydrofuran complex is added dropwise. The reaction mixture is stirred at room temperature for 30 min, then at 40° C. for 3 h. 0.1 ml of borane tetrahydrofuran complex is added again and the reacton mixture is stirred at 50° C. overnight. The reaction mixture is partitioned between dichloromethane and water, the organic phase is washed with a saturated NaHCO₃ water solution, dried over phase separator and concentrated under vacuum to give 42 mg of intermediate A.59.

A.60

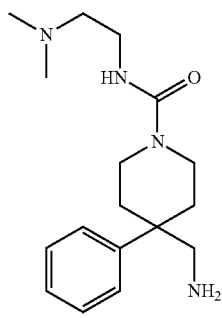

To a solution of 1 g of intermediate B.56 in 20 ml of THF stirred at −78° C., 1.2 ml of a 2M solution of lithium aluminium hydride in THF is added dropwise. The mixture is allowed to reach is room temperature and stirred overnight. The solvent is concentrated, the reaction mixture is partitioned between dichloromethane and water and organic phase is dried over phase separator and concentrated under vacuum to give 500 mg of crude product. 200 mg of this crude product are purified by preparative LC-MS (reverse phase; NH₄COOH). 60 mg of pure intermediate A.60 are obtained.

7.2 Synthesis of Examples

Example 1

4-[N'-(3,5-Diamino-6-chloro-pyrazine-2-carbonyl)-guanidinomethyl]-4-phenethyl-piperidine-1-carboxylic acid tert-butyl ester

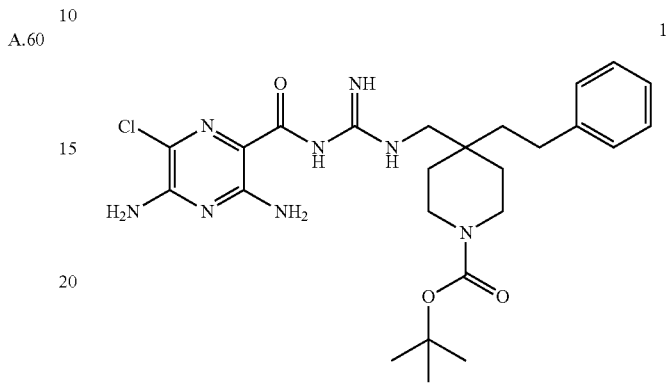

A mixture of 80 mg (0.3 mmol) 4-aminomethyl-4-phenethyl-piperidine-1-carbocylic acid tert-butyl ester (A.55) and 104 mg (0.3 mmol) 1-(3,5-diamino-6-chloro-pyrazine-2-carbonyl)-2-methyl-isothiourea (intermediate C.61) in 2 ml acetonitrile is stirred at 70° C. for 48 hours. Then the reaction mixture is concentrated under reduced pressure and the residue is purified by preparative reverse phase HPLC (gradient of acetonitrile and water+0.2% trifluoroacetic acid, 25° C.). Fractions containing the title compound were concentrated under reduced pressure.
Yield: 116 mg.
ESI mass spectrum: $[M+H]^+$=531
Retention time HPLC: 2.51 min (method M1).
The following compounds are prepared accordingly from starting materials as indicated:

TABLE 1

| Example | A | R¹ | R² | R³ | R⁴ | Starting material | IC50 [μM] | ESI+ (M + H)+ | Ret. [min] | HPLC Method |
|---------|------|------|------|------|------|------|-------|------|------|------|
| 1.1 | —CH₂—CH₂— | O=S(=O)—* | H | H | H | A.1 | 0.034 | 509 | 1.21 | M2 |
| 1.2 | —CH₂—CH₂— | HN—C(=O)—CH(CH₃)₂ * | H | H | H | A.2 | 0.008 | 516 | 1.28 | M2 |
| 1.3 | —CH₂—CH₂— | isopropyl * | H | H | H | A.3 | 0.033 | 445 | 1.67 | M1 |

TABLE 1-continued

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.4 | —CH₂—CH₂— | *-C(O)NH₂ | H | H | H | A.4 | 0.027 | 474 | 1.21 | M2 |
| 1.5 | —CH₂—CH₂— | *-C(O)-phenyl | H | H | H | A.5 | 0.034 | 535 | 2.23 | M1 |
| 1.6 | —CH₂—CH₂— | *-CH₂-phenyl | H | H | H | A.6 | 0.040 | 521 | 1.90 | M2 |
| 1.7 | —CH₂—CH₂— | *-CH(CH₃)₂ (isobutyl) | H | H | H | A.7 | 0.063 | 473 | 0.95 | M2 |
| 1.8 | CH2 | *-C(O)NH-iPr | H | H | H | A.8 | 0.017 | 502 | 1.25 | M2 |
| 1.9 | —CH₂—CH₂— | *-C(O)CH₂OCH₃ | H | H | H | A.9 | 0.011 | 503 | 1.41 | M2 |
| 1.10 | —CH₂—CH₂— | *-C(O)NH-CH₂CH₂-N(CH₃)₂ | H | H | H | A.10 | 0.036 | 545 | 1.42 | M4 |
| 1.11 | —CH₂—CH₂— | *-C(O)-CH₂-CH(CH₃)₂ | H | H | H | A.11 | 0.017 | 515 | 1.49 | M2 |

TABLE 1-continued

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.12 | —CH₂—CH₂— | *-CH₂-CH₂-NH-C(=O)- (ethylcarbamoyl) | H | H | H | A.12 | 0.012 | 502 | 1.30 | M2 |
| 1.13 | —CH₂—CH₂— | *-C(=O)-CH₂-CH₂-CH₃ (butanoyl) | H | H | H | A.13 | 0.013 | 501 | 1.36 | M2 |
| 1.14 | —CH₂—CH₂— | *-C(=O)-CH₂-CH₂-C(=O)-OMe | H | H | H | A.14 | 0.020 | 545 | 1.23 | M2 |
| 1.15 | —CH₂—CH₂— | cyclopropyl with CF₃ and COO— | H | H | H | A.15 | 0.091 | 459 (M+) | 1.05 | M2 |
| 1.16 | —CH₂—CH₂— | *-CH₂-C(=O)-OMe | H | H | H | A.16 | 0.002 | 503 | 1.07 | M2 |
| 1.17 | —CH₂—CH₂— | *-C(=O)-O-C(CH₃)₃ (Boc) | H | H | COOMe | A.17 | 0.056 | 589 | | |
| 1.18 | —CH₂—CH₂— | *-C(=O)-NH-CH₂-C(=O)-OMe | H | H | H | A.18 | 0.028 | 546 | 1.30 | M2 |

TABLE 1-continued

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.19 | —CH₂—CH₂— | (3-methoxycarbonylpropanoylamino-methyl, *-NH-C(O)-CH₂-CH₂-C(O)-O-CH₃) | H | H | H | A.19 | 0.024 | 560 | 1.33 | M2 |
| 1.20 | —CH₂— | (*-C(O)-CH₂-CH₂-C(O)-O-CH₃) | H | H | H | A.20 | 0.075 | 531 | 1.04 | M6 |
| 1.21 | —CH₂— | (*-CH₃) | H | H | H | A.21 | 0.089 | 431 | | |
| 1.22 | —CH₂—CH₂— | (*-C(O)-CH₂-CH₂-NH-C(O)-O-C(CH₃)₃) | H | H | H | A.22 | 0.037 | 602 | 1.26 | M7 |
| 1.23 | —CH₂—CH₂— | (*-C(O)-CH₂-CH₂-CH₂-NH-C(O)-O-C(CH₃)₃) | H | H | H | A.23 | 0.026 | 502 | 1.19 | M6 |

TABLE 1-continued

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.24 | —CH₂— | tert-butyl (2-oxoethyl)carbamate group | H | H | H | A.24 | 0.027 | 574 | 1.19 | M8 |
| 1.25 | —CH₂—CH₂— | tert-butyl (2-oxoethyl)carbamate group | H | H | H | A.25 | 0.018 | 588 | 1.27 | M7 |
| 1.26 | —CH₂— | tert-butyl (5-oxopentyl)carbamate group | H | H | H | A.26 | 0.019 | 616 | 1.27 | M7 |
| 1.27 | —CH₂— | tert-butyl (3-oxopropyl)carbamate group | H | H | H | A.27 | 0.033 | 588 | 1.24 | M7 |

TABLE 1-continued
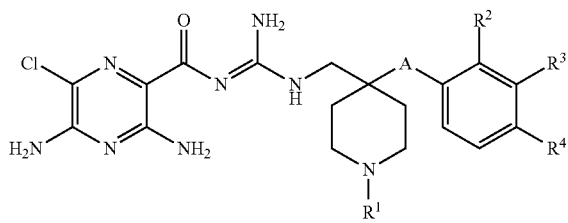
| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.28 | —CH₂—CH₂— | 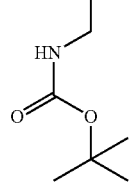 | H | H | H | A.28 | 0.036 | 588 | 1.08 | M7 |
| 1.29 | —CH₂—CH₂— | 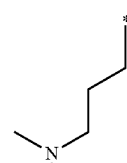 | H | H | H | A.29 | 0.086 | 516 | 0.90 | M7 |
| 1.30 | —CH₂— | 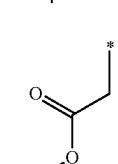 | H | H | H | A.30 | 0.070 | 489 | 1.13 | M8 |
| 1.31 | —CH₂— | 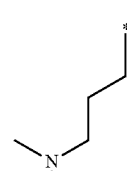 | H | H | H | A.31 | 0.287 | 502 | 0.87 | M7 |
| 1.32 | —CH₂—CH₂— | 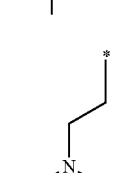 | H | H | H | A.32 | 0.046 | 502 | 0.90 | M7 |
| 1.33 | —CH₂—CH₂— | 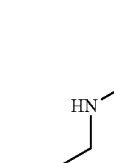 | H | H | H | A.33 | 0.007 | 617 | 1.14 | M6 |

TABLE 1-continued
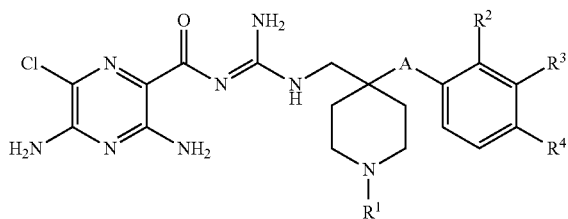
| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.34 | —CH₂—CH₂— | (3-Boc-aminopropylcarbamoyl) | H | H | H | A.34 | 0.010 | 631 | 1.18 | M6 |
| 1.35 | —CH₂— | (2-Boc-aminoethylcarbamoyl) | H | H | H | A.35 | 0.011 | 603 | 1.65 | M5 |
| 1.36 | —CH₂— | (3-Boc-aminopropylcarbamoyl) | H | H | H | A.36 | 0.018 | 617 | 1.68 | M5 |
| 1.37 | —CH₂— | (3-Boc-aminopropyl) | H | H | H | A.37 | 0.064 | 574 | 1.42 | M5 |

TABLE 1-continued

| Example | A | R¹ | R² | R³ | R⁴ | Starting material | IC50 [μM] | ESI+ (M+H)+ | Ret. [min] | HPLC Method |
|---|---|---|---|---|---|---|---|---|---|---|
| 1.38 | —CH₂— | *-CH₂-CH₂-CH₂-NH-C(O)-N(CH₃)₂ (see structure) | H | H | H | A.38 | 0.042 | 545 | 1.38 | M4 |
| 1.39 | —CH₂—CH₂— | *-CH₂-CH₂-CH₂-NH-C(O)-N(CH₃)₂ (see structure) | H | H | H | A.39 | 0.023 | 559 | 1.44 | M4 |
| 1.40 | —CH₂— | *-CH₂-CH₂-NH-C(O)-N(CH₃)₂ (see structure) | H | H | H | A.40 | 0.029 | 531 | 1.35 | M5 |
| 1.41 | —CH₂— | *-CH₂-CH₂-N(CH₃)₂ (see structure) | H | H | H | A.41 | 0.091 | 488 | 1.20 | M5 |
| 1.42 | bond | *-C(O)-O-C(CH₃)₃ (see structure) | H | H | H | A.42 | 0.025 | 503 | 2.28 | M1 |
| 1.43 | bond | *-C(O)-NH-CH(CH₃)₂ (see structure) | H | H | H | A.43 | 0.041 | 488 | 1.52 | M3 |

TABLE 1-continued
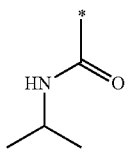
| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.44 | bond | 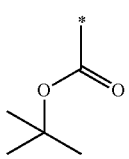 | H | —O—CH2—O— | | A.44 | 0.046 | 532 | 1.56 | M3 |
| 1.45 | bond | 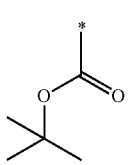 | O—Me | H | H | A.45 | 0.066 | 533 | 1.78 | M3 |
| 1.46 | —CH₂— | 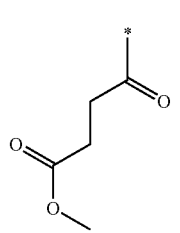 | H | H | H | A.46 | 0.061 | 517 | 1.83 | M3 |
| 1.47 | bond | 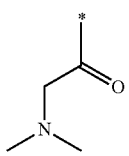 | H | H | H | A.47 | 0.029 | 517 | 1.000 | M6 |
| 1.48 | —CH₂—CH₂— | 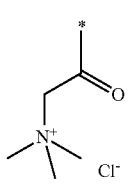 | H | H | H | A.51 | 0.13 | 516 | 1.0 | M7 |
| 1.49 | —CH₂—CH₂— | 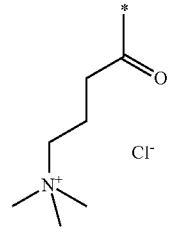 | H | H | H | A.52 | 0.022 | 530 | 1.01 | M7 |
| 1.50 | —CH₂—CH₂— |  | H | H | H | A.53 | 0.015 | 558 | 1.50 | M5 |

TABLE 1-continued

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.51 | —CH₂—CH₂— | (*-C(O)-NH-CH₂-CH₂-N(CH₃)₂) | H | H | COOMe | A.54 | | | | |
| 1.52 | —CH₂—CH₂— | (*-C(O)-NH-CH₂-CH₂-N(CH₃)₂) | H | H | CONH2 | A.56 | | | | |

Example 1.53

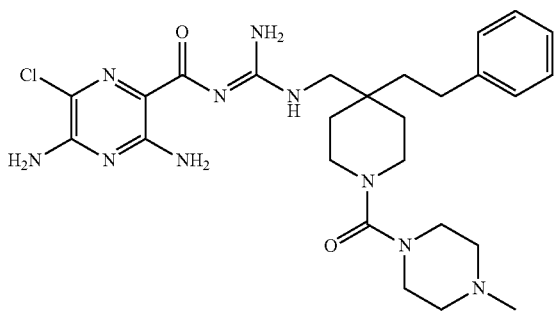 [SMILES: CN1CCN(C(=O)N2CCC(CCc3ccccc3)(CN/C(N)=N/C(=O)c3nc(Cl)c(N)nc3N)CC2)CC1]

To a solution of 140 mg (0.36 mmol) of intermediate A.57 in 2.5 ml of DMF, 0.13 ml of N,N-diisopropylethilamine is added. The reaction mixture is stirred at room temperature for 10 minutes then 85 mg (0.33 mmol) of 1-(3,5-diamino-6-chloro-pyrazine-2-carbonyl)-2-methylisothiourea is added. The reaction mixture is heated at 70° C. for 3 hours. The solvent is removed and the crude product obtained is purified by flash chromatography (first eluent: AcOEt/MeOH=90/10 in order to remove impurities; second eluent dichloromethane/MeOH/NH3 from 90/10/0.1 to 50/50/0.1 to give the desired product).

Yield: 55 mg.

IC50[μM]=0.014

ESI mass spectrum: [M+H]⁺=557

Retention time HPLC: 5.60 min (method M9).

The following compounds are prepared accordingly from starting materials as indicated:

TABLE 1.1

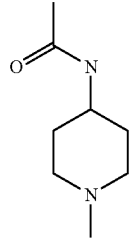

| Example | A | R¹ | R² | R³ | R⁴ | Starting material | IC50 [μM] | ESI+ (M + H)+ | Ret. [min] | HPLC Method |
|---|---|---|---|---|---|---|---|---|---|---|
| 1.54 | —CH₂—CH₂— | 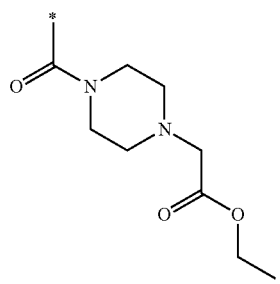 | H | H | H | A.58 | 0.046 | 571 | 5.38 | M10 |
| 1.55 | —CH₂—CH₂— | 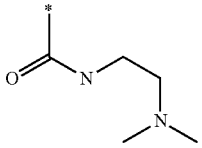 | H | H | H | A.59 | n.a. | 629 | 3.52 | M11 |
| 1.56 | bond | 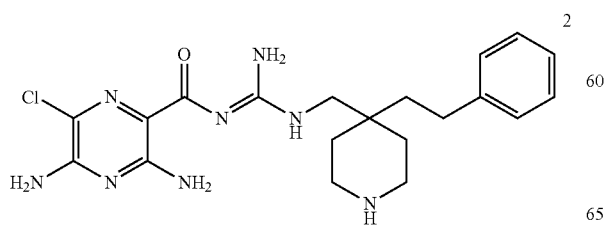 | H | H | H | A.60 | n.a. | 517 | 3.08 | M11 |

Example 2

N-(3,5-Diamino-6-chloro-pyrazine-2-carbonyl)-N'-(4-phenethyl-piperidin-4-ylmethyl-guanidine A mixture of 50 mg (0.3 mmol) 4-[N'-(3,5-diamino-6-chloro-pyrazine-2-carbonyl)-guanidinomethyl]-4-phenethyl-piperidine-1-carboxylic acid tert-butyl ester (Example 1) in 1 ml dichloromethane is stirred with 250 μl trifluoroacetic acid at room temperature for 2 h. Then the reaction mixture is concentrated under reduced pressure.

Yield: 40 mg.

ESI mass spectrum: [M+H]⁺=431

Retention time HPLC: 1.78 min (method M1).

The following compounds are prepared accordingly from starting materials as indicated:

TABLE 2
| Example | A | R¹ | R² | R³ | R⁴ | Starting material | IC50 [μM] | ESI+ (M + H)+ | Ret. [min] | Methode HPLC |
|---|---|---|---|---|---|---|---|---|---|---|
| 2.1 | —CH₂—CH₂— | *—H | H | H | COOMe | 1.17 | 0.394 | 489 | | |
| 2.2 | —CH₂—CH₂— | *—C(O)—CH₂—CH₂—NH₂ | H | H | H | 1.22 | 0.019 | 502 | | |
| 2.3 | —CH₂—CH₂— | *—C(O)—CH₂—CH₂—CH₂—NH₂ | H | H | H | 1.23 | 0.023 | 530 | 1.03 | M7 |
| 2.4 | —CH₂— | *—C(O)—CH₂—NH₂ | H | H | H | 1.24 | 0.059 | 508 (M + CL)− | 0.90 | M6 |
| 2.5 | —CH₂—CH₂— | *—CH₂—CH₂—CH₂—NH₂ | H | H | H | 1.28 | 0.065 | 488 | 0.89 | M6 |
| 2.6 | —CH₂—CH₂— | *—C(O)—NH—CH₂—CH₂—CH₂—NH₂ | H | H | H | 1.34 | 0.028 | 531 | 1.57 | M4 |
| 2.7 | —CH₂—CH₂— | *—C(O)—NH—CH₂—CH₂—NH₂ | H | H | H | 1.33 | 0.016 | 517 | 1.56 | M4 |

TABLE 2-continued
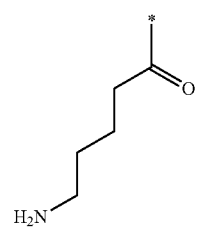
| Example | A | R¹ | R² | R³ | R⁴ | Starting material | IC50 [μM] | ESI+ (M + H)+ | Ret. [min] | Methode HPLC |
|---|---|---|---|---|---|---|---|---|---|---|
| 2.8 | —CH₂— | 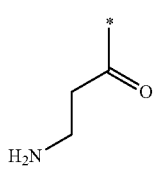 | H | H | H | 1.26 | 0.061 | 516 | 0.97 | M7 |
| 2.9 | —CH₂— | 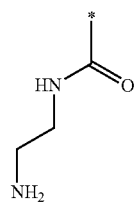 | H | H | H | 1.27 | 0.093 | 488 | 0.96 | M7 |
| 2.10 | bond | H | O—Me | H | H | 1.45 | 0.200 | 433 | 1.26 | M3 |
| 2.11 | —CH₂— | H | H | H | H | 1.46 | 0.055 | 417 | 1.31 | M3 |
| 2.12 | —CH₂— | 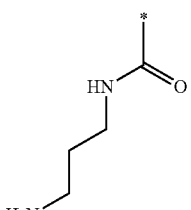 | H | H | H | 1.35 | 0.017 | 503 | 0.93 | M6 |
| 2.13 | —CH₂— | 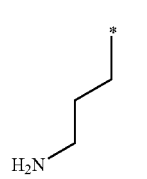 | H | H | H | 1.36 | 0.025 | 517 | 0.93 | M6 |
| 2.14 | —CH₂— |  | H | H | H | 1.37 | 0.12 | 474 | 0.85 | M6 |

Example 3

(4-(N'-(3,5-Diamino-6-chloro-pyrazine-2-carbonyl)-guanidinomethyl]-4-phenethyl-piperidin-1-yl)acetic acid

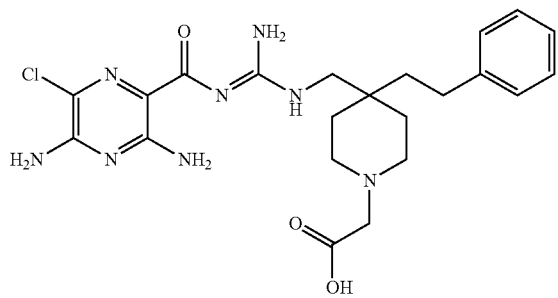

A mixture of 145 mg (0.23 mmol) {4-[N'-(3,5-diamino-6-chloro-pyrazine-2-carbonyl)-guanidinomethyl]-4-phenethyl-piperidin-1-yl}-acetic acid methyl ester (Example 1.16) in 5 ml methanol and 235 µl 4 N NaOH is stirred at 50° C. for 1 hour. Then the solution is acidified with 470 µl 4 N HCl and concentrated under reduced pressure. The residue is purified by preparative reverse phase HPLC (gradient of acetonitrile and water+0.2% trifluoroacetic acid, 25° C.). Fractions containing the title compound were concentrated under reduced pressure.

Yield: 35 mg.

ESI mass spectrum: $[M+H]^+=489$

Retention time HPLC: 1.33 min (method M2)

The following compounds are prepared accordingly from starting materials as indicated:

TABLE 3

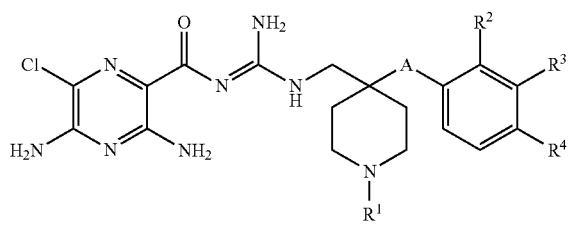

| Example | A | R1 | R2 | R3 | R4 | Starting material | IC50 [µM] | ESI+ (M + H)+ | Ret. [min] | Methode HPLC |
|---|---|---|---|---|---|---|---|---|---|---|
| 3.1 | —CH₂—CH₂— | * (see structure) | H | H | H | 1.14 | 0.040 | 531 | 1.21 | M2 |
| 3.2 | —CH₂—CH₂— | * (see structure) | H | H | H | 1.19 | 0.149 | 546 | 1.43 | M2 |
| 3.3 | —CH₂—CH₂— | * (see structure) | H | H | H | 1.18 | 0.0101 | 532 | 1.27 | M2 |

Example 4

4-[N'-(3,5-Diamino-6-chloro-pyrazine-2-carbonyl)-guanidinomethyl]-4-phenethyl-piperidine-1-carboxamidine

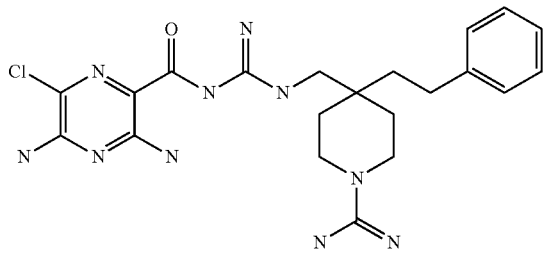 [SMILES: N=C(NCC1(CCc2ccccc2)CCN(C(=N)N)CC1)NC(=O)c1nc(Cl)c(N)nc1N]

A mixture of 70 mg (0.15 mmol) N-(3,5-diamino-6-chloro-pyrazine-2-carbonyl)-N'-(4-phenethyl-piperidin-4-ylmethyl-guanidine (Example 2), 124 μl triethylamine and 28 mg (0.19 mmol) 1H-1.2.4-triazole-1-carboxamidine mono-hydrochloride in 5 ml DMF is stirred at 70° C. for 2 hours. Then 1 ml methanol is added and the mixture is purified by preparative reverse phase HPLC (gradient of acetonitrile and water+0.2% trifluoroacetic acid, 25° C.). Fractions containing the title compound were concentrated under reduced pressure.

Yield: 15 mg.
ESI mass spectrum: $[M+H]^+=473$
Retention time HPLC: 0.93 min (method M7)

The following compounds are prepared accordingly from starting materials as indicated:

TABLE 4

| Example | A | R¹ | R² | R³ | R⁴ | Starting material | IC50 [μM] | ESI+ (M + H)+ | Ret. [min] | Methode HPLC |
|---|---|---|---|---|---|---|---|---|---|---|
| 4.1 | —CH₂—CH₂— | (guanidino-propanoyl) | H | H | H | 2.2 | 0.012 | 544 | 1.01 | M7 |
| 4.2 | —CH₂—CH₂— | (guanidino-butanoyl) | H | H | H | 2.3 | 0.018 | 570 (M − H)− | 1.51 | M4 |

Example 5

(2-((4-[N'-(3,5-Diamino-6-chloro-pyrazine-2-carbonyl)-guanidinomethyl]-4-phenethyl-piperidine-1-carbonyl)-amino)-ethyl]-trimethyl-ammonium chloride Ex. 5.A

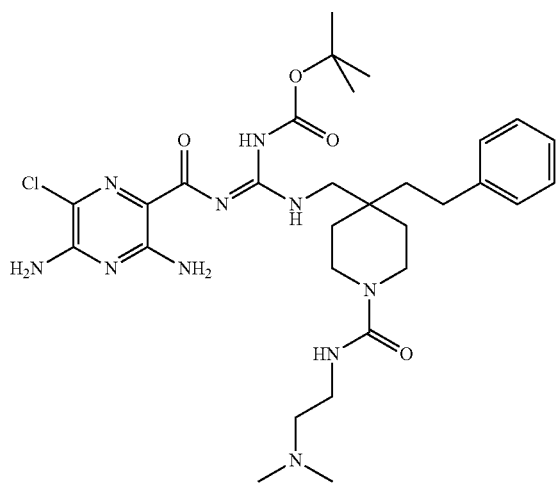

1.55 g 4-[N'-(3,5-Diamino-6-chloro-pyrazine-2-carbonyl)-guanidinomethyl]-4-phenethyl-piperidine-1-carboxylic acid (2-dimethylamino-ethyl)-amide (example 1.40), 0.9 ml triethylamine and 1.1 g BOC anhydride were dissolved in 50 ml THF and stirred over night. The organic layer is separated and concentrated under reduced pressure.

Yield: 1.3 g

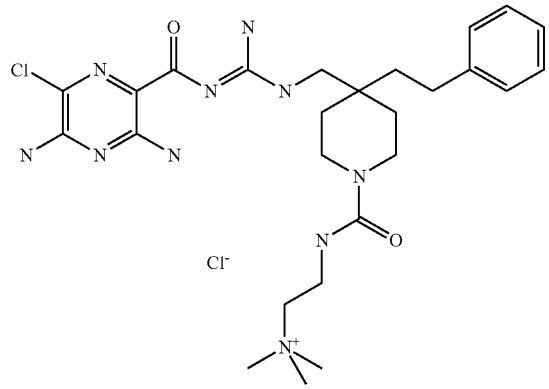

A mixture of 1.3 g Ex. 5.A and 200 µl methyl iodide in 10 ml acetone is stirred overnight at room temperature. Then the reaction mixture is concentrated under reduced pressure and 5 ml of a 50% solution of trifluoroacetic acid in dichloromethane is added and stirred for 2 h at room temperature. Then the mixture is co-evaporated with methanolic hydrochloric acid. The is residue is purified via preparative reverse phase HPLC (gradient of acetonitrile and water+0.2% trifluoroacetic acid, 25° C.). Fractions containing the title compound were concentrated under reduced pressure and finally co-evaporated with methanolic hydrochloric acid.

Yield: 820 mg.
ESI mass spectrum: [M]+=559
Retention time HPLC: 0.97 min (method M7)

The following compounds are prepared accordingly from starting materials as indicated:

TABLE 5

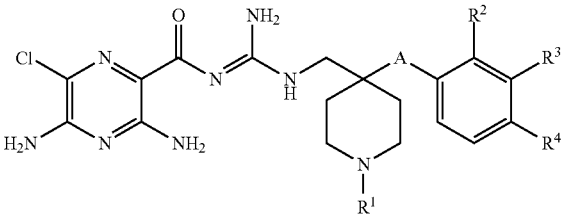

| Example | A | R¹ | R² | R³ | R⁴ | Starting material | IC50 [µM] | ESI+ (M + H)+ | Ret. [min] | Methode HPLC |
|---------|---|----|----|----|----|-------------------|-----------|---------------|------------|--------------|
| 5.1 | —CH₂—CH₂— | 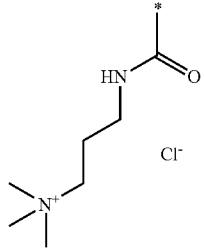 | H | H | H | 1.39 | 0.027 | 573 (M+) | 1.013 | M7 |

TABLE 5-continued

| Example | A | R¹ | R² | R³ | R⁴ | Starting material | IC50 [μM] | ESI+ (M + H)+ | Ret. [min] | Methode HPLC |
|---|---|---|---|---|---|---|---|---|---|---|
| 5.2 | —CH₂—CH₂— | *-C(O)-NH-CH₂-CH₂-N⁺(CH₃)₃ Cl⁻ | H | H | COOMe | 1.51 | 0.074 | 617 | 1.01 | M7 |
| 5.3 | —CH₂—CH₂— | *-C(O)-NH-CH₂-CH₂-N⁺(CH₃)₃ Cl⁻ | H | H | CONH2 | 1.52 | 0.12 | 301 (M++) | 0.80 | M7 |
| 5.4 | —CH₂—CH₂— | *-C(O)-piperazine-N⁺(CH₃)₂ Cl⁻ | H | H | H | 1.53 | 0.051 | 571 | 2.80 | M9 |
| 5.5 | —CH₂—CH₂— | *-C(O)-NH-piperidine-N⁺(CH₃)₂ I⁻ | H | H | H | 1.54 | 0.052 | 585 | 3.47 | M11 |
| 5.6 | — | *-C(O)-NH-CH₂-CH₂-N⁺(CH₃)₃ HCOO⁻ | H | H | H | 1.56 | n.a. | 531 | 4.88 | M11 |

Example 6

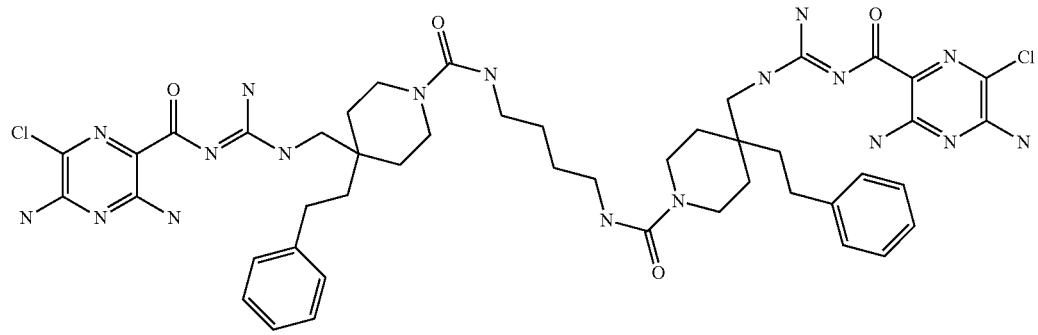 [SMILES: N/C(=N\C(=O)c1nc(Cl)c(N)nc1N)NCC1(CCc2ccccc2)CCN(C(=O)NCCCCNC(=O)N2CCC(CCc3ccccc3)(CN/C(N)=N/C(=O)c3nc(Cl)c(N)nc3N)CC2)CC1]

A mixture of 115 mg A.48 and 104 mg (0.3 mmol) 1-(3,5-Diamino-6-chloro-pyrazine-2-carbonyl)-2-methyl-isothiourea in 25 ml THF are stirred at 70° C. for 80 hours. Then the reaction mixture is concentrated under reduced pressure and the residue is purified via chromatography (Silica, dichloromethane/methanol plus 10% ammonia 9:1 to 6/4). Fractions containing the title compound were concentrated under reduced pressure.

Yield: 27 mg.

ESI mass spectrum: $[M+H]^+=1001$

Retention time HPLC: 1.41 min (method M2).

The following compounds are prepared accordingly from starting materials as indicated:

TABLE 6

| Example | Structure | Starting material | IC50 [μM] | ESI+ (M + H)+ | Ret. [min] | Methode HPLC |
|---|---|---|---|---|---|---|
| 6.1 | 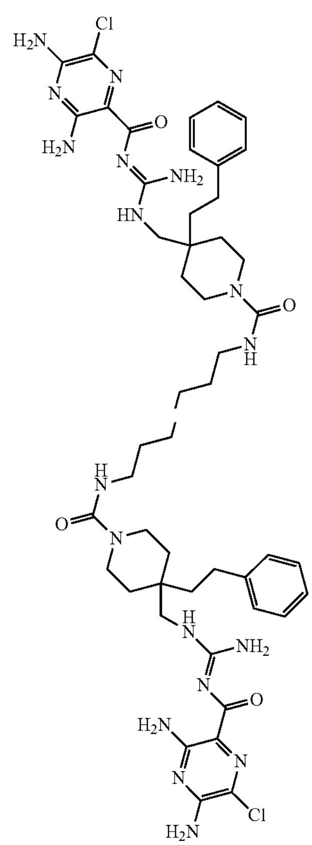 | A.49 | 0.097 | (M + H)/2 + 515 | 1.52 | M2 |

Example 7

N-(3,5-Diamino-6-chloro-pyrazine-2-carbonyl)-N'-(4-phenethyl-1-phenylacetyl-piperidin-4-ylmethyl)-guanidine

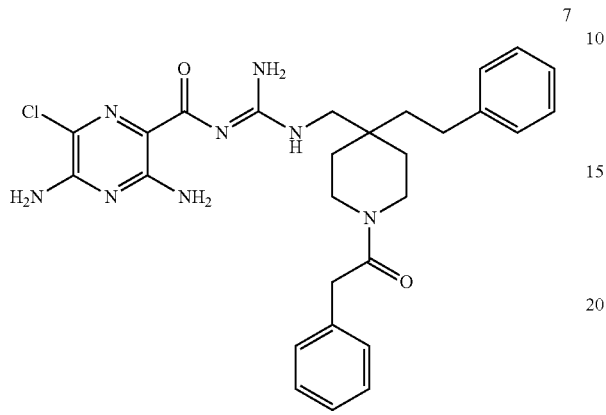

To a mixture of 70 mg (0.14 mmol) N-(3,5-diamino-6-chloro-pyrazine-2-carbonyl)-N'-(4-phenethyl-piperidin-4-ylmethyl)-guanidine (example 2) and 118 µl Hunig's base in 5 ml dichloromethane 27 µM (0.21 mmol) phenacetylchloride is dropwise added and stirred at room temperature overnight. Then the mixture concentrated under reduced pressure. The residue is purified via preparative reverse phase HPLC (gradient of acetonitrile and water+0.2% trifluoroacetic acid, 25° C.). Fractions containing the title compound were concentrated under reduced pressure.
Yield: 9 mg.
ESI mass spectrum: $[M+H]^+=549$
Retention time HPLC: 1.42 min (method M2)

Example 8

4-[N'-(3,5-Diamino-6-chloro-pyrazine-2-carbonyl)-guanidinomethyl]-4-phenethyl-piperidine-1-carboxylic acid propylamide

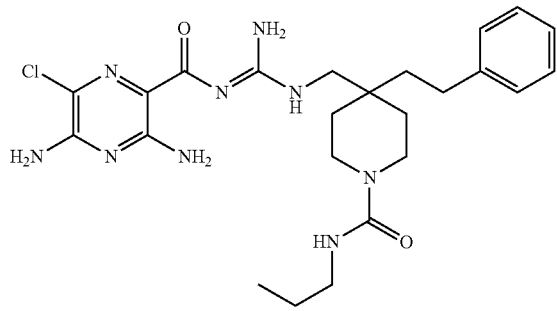

To a mixture of 100 mg (0.198 mmol) N-(3,5-diamino-6-chloro-pyrazine-2-carbonyl)-N'-(4-phenethyl-piperidin-4-ylmethyl)-guanidine (example 2) and 29 µl DBU in 5 ml THF 12 µM (0.2 mmol) N-propylisocyanat is dropwise added and stirred at room temperature for 2 h. Then the mixture is concentrated under reduced pressure. The residue is purified via preparative reverse phase HPLC (gradient of acetonitrile and water+0.2% trifluoroacetic acid, 25° C.). Fractions containing the title compound were concentrated under reduced pressure.
Yield: 10 mg.
ESI mass spectrum: $[M+H]^+=516$
Retention time HPLC: 2.2 min (method M1)

Example 9

N-[1-(2-Amino-acetyl)-4-phenethyl-piperidin-4-ylmethyl-N'-(3,5-diamino-6-chloro-pyrazine-2-carbonyl)-guanidine

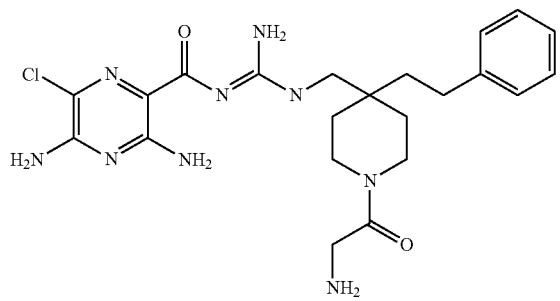

A mixture of 130 mg (0.35 mmol) [2-(4-aminomethyl-4-phenethyl-piperidin-1-yl)-2-oxo-ethyl]-carbamic acid tert-butyl ester (A.50) and 80 mg (0.3 mmol) 1-(3,5-diamino-6-chloro-pyrazine-2-carbonyl)-2-methyl-isothiourea in 5 ml tetrahydrofuran is stirred at 70° C. overnight. Then the reaction mixture is concentrated under reduced pressure and the residue is purified via preparative reverse phase HPLC (gradient of acetonitrile and water+0.2% trifluoroacetic acid, 25° C.). Fractions containing the title compound were concentrated under reduced pressure. Then the residue is co-evaporated with methanolic hydrochloric acid in order to remove the protecting group.
Yield: 37 mg.
ESI mass spectrum: $[M+H]^+=488$
Retention time HPLC: 1.08 min (method M7).

Example 10

4-{4-[N'-(3,5-Diamino-6-bromo-pyrazine-2-carbonyl)-guanidinomethyl]-4-phenethyl-piperidin-1-yl}-4-oxo-butyric acid methyl ester

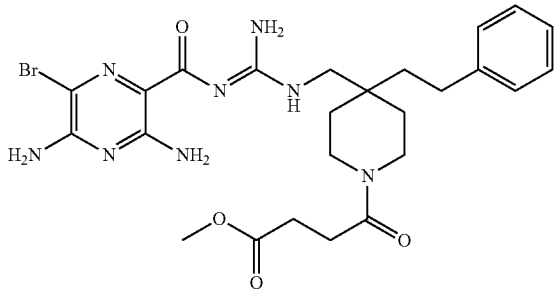

The compound is prepared as described for example 1.14 applying 3,5-diamino-6-bromo-N-[(methylsulfanyl)methanimidoyl]pyrazine-2-carboxamide (intermediate C.62) instead of intermediate C.61.

ESI mass spectrum: $[M+H]^+=589$
Retention time HPLC: 0.72 min (method M12)
IC50[μM]=0.032

Example 11

4-{4-[N'-(3,5-Diamino-6-bromo-pyrazine-2-carbonyl)-guanidinomethyl]-4-phenethyl-piperidin-1-yl}-4-oxo-butyric acid

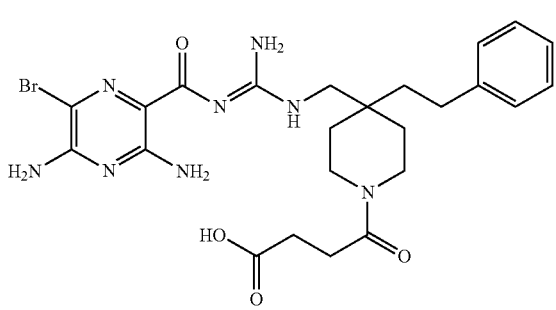

The compound is prepared analogously to the procedure described for the synthesis of example 3, applying example 10 as starting material.

ESI mass spectrum: $[M+H]^+=575$
Retention time HPLC: 0.49 min (method M13)
IC50[μM]=0.502

8. ANALYTICAL METHODS

HPLC/MS Methods
Method: M1
Waters ZQ2000; Waters 1515 pump, Waters PDA 996 Detector, Waters 2747 Injector
Mobile Phase: A: Water+0.1% formic acid
B: Acetonitrile+0.1% formic acid
Gradient:

| time in min | % A | % B | flow rate in ml/min |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 |

Stationary Phase: X-terra™ MS C18 2.5 μm 4.6 mm×30 mm
Column temperature about 25° C.
Diode array detection wave length range 210-420 nm
mass range m/z 80 to 800
Ionization: ESI positive
Method: M2
Waters ZQ2000; Waters 1515 Pump, Waters PDA 996 Detector, Waters 2747 Injector
Mobile Phase: A: water+0.1% formic acid
B: Acetonitrile+0.1% formic acid
Gradient:

| time in min | % A | % B | flow rate in ml/min |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Stationary Phase: X-terra™ MS C18 2.5 μm 4.6 mm×30 mm
Column temperature about 25° C.
Diode array detection range 210-420 nm
Mass range m/z 80 to 800
Ionization: ESI positive/negative
Method: M3
Analytical column: XBridge C18 (Waters technologies)
XBridge C18, 4.6×30 mm, 2.5 μm column temperature 60° C.
Mobile phase A: H2O: trifluoroacetic acid 99.9:0.1
Mobile phase B: Methanol: trifluoroacetic acid 99.9:0.1
Gradient:

| time in min | % A | % B | flow rate in ml/min |
|---|---|---|---|
| 0.0 | 95 | 5 | 4 |
| 0.05 | 95 | 5 | 3 |
| 2.05 | 0 | 100 | 3 |
| 2.10 | 0 | 100 | 4 |
| 2.35 | 0 | 100 | 4 |

Method: M4
Analytical column: XBridge 018 (Waters technologies)
XBridge C18, 4.6×30 mm, 2.5 μm column temperature 60° C.
Mobile phase A: $H_2O$: trifluoroacetic acid 99.9:0.1
Mobile phase B: Methanol: 100
Gradient:

| time in min | % A | % B | flow rate in ml/min |
|---|---|---|---|
| 0.0 | 95 | 5 | 4 |
| 0.05 | 95 | 5 | 3 |
| 2.05 | 0 | 100 | 3 |
| 2.10 | 0 | 100 | 4.5 |
| 2.40 | 0 | 100 | 4.5 |

Method: M5
Analytical column: Sunfire C18 (Waters technologies)
Sunfire C18, 4.6×30 mm, 2.5 µm column temperature 60° C.
Mobile phase A: H$_2$O: trifluoroacetic acid 99.9:0.1
Mobile phase B: Methanol: 100
Gradient:

| time in min | % A | % B | flow rate in ml/min |
|---|---|---|---|
| 0.0 | 95 | 5 | 4 |
| 0.05 | 95 | 5 | 3 |
| 2.05 | 0 | 100 | 3 |
| 2.10 | 0 | 100 | 4.5 |
| 2.40 | 0 | 100 | 4.5 |

Method: M6
Analytical column: XBridge C18 (Waters technologies)
XBridge C18, 3.0×30 mm, 2.5 µm column temperature 60° C.
Mobile phase A: H$_2$O: trifluoroacetic acid 99.9:0.1
Mobile phase B: Methanol: 100
Gradient:

| time in min | % A | % B | flow rate in ml/min |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.65 | 0 | 100 | 2.9 |

Method: M7
Analytical column: Sunfire C18 (Waters technologies)
Sunfire C18, 3.0×30 mm, 2.5 µm column temperature 60° C.
Mobile phase A: H2O: trifluoroacetic acid 99.9:0.1
Mobile phase B: Methanol: 100
Gradient:

| time in min | % A | % B | flow rate in ml/min |
|---|---|---|---|
| 0.0 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Method: M8
Analytical column: XBridge C18 (Waters technologies)
XBridge C18, 3.0×30 mm, 2.5 µm column temperature 60° C.
Mobile phase A: H2O: Ammonia 99.9:0.1
Mobile phase B: Methanol: 100
Gradient:

| time in min | % A | % B | flow rate in ml/min |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Method: M9
Instrument: LC/MS ThermoFinnigan HPLC Surveyor DAD, MSQ single quadrupole
Column: Synergi Hydro RP100A, 2.5 µm, 3×50 mm
Mobile phase: A=H2O 90%+10% CH3CN+NH4COOH 5 mM
B=CH3CN 90%+H2O 10%
Gradient:

| time in min | % A | % B | flow rate in ml/min |
|---|---|---|---|
| 0.0 | 100 | 0 | 1.2 |
| 4.00 | 0 | 100 | 1.2 |
| 5.30 | 0 | 100 | 1.2 |
| 5.50 | 100 | 0 | 1.2 |
| 6.00 | 100 | 0 | 1.2 |

Detection: UV 254 nm
Detection: Finnigan MSQ, single quadrupole
Ion source: APCI+/APCI−
Scan range: 100-900 amu

Method: M10
Instrument: LC/MS ThermoFinnigan HPLC Surveyor DAD, MSQ single quadrupole
Column: Synergi Hydro RP100A, 2.5 µm, 3×50 mm
Mobile phase: A=H2O 90%+10% CH3CN+NH4COOH 5 mM
B=CH3CN 90%+H2O 10%
Gradient:

| time in min | % A | % B | flow rate in ml/min |
|---|---|---|---|
| 0.0 | 100 | 0 | 1.2 |
| 1.5 | 100 | 0 | 1.2 |
| 9.00 | 0 | 100 | 1.2 |
| 10.50 | 0 | 100 | 1.2 |
| 11.00 | 100 | 0 | 1.2 |
| 12.00 | 100 | 0 | 1.2 |

Detection: UV 254 nm
Detection: Finnigan MSQ, single quadrupole
Ion source: APCI+/APCI−
Scan range: 100-900 amu

Method: M11
Instrument: LC/MS Waters Alliance 2695 HPLC System DAD, Quattro Micro Triple quadrupole
Column: Atlantis dC18 5 m 4.6×50 mm, Temp 35° C.
Mobile phase: A=H$_2$O 90%+10% CH$_3$CN+CF$_3$COOH 0.05%
B=CH$_3$CN 90%+10% H$_2$O
Gradient:

| time in min | % A | % B | flow rate in ml/min |
|---|---|---|---|
| 0.0 | 100 | 0 | 1.3 |
| 0.70 | 100 | 0 | 1.3 |
| 4.5 | 0 | 100 | 1.3 |
| 5.8 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu

Method: M12

| Column: | Sunfire, 3 × 30 mm, 2.5 µm (Waters) | | | |
|---|---|---|---|---|
| Gradient time [min] | % Sol [H2O, 0.1% TFA] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: M13

| Column: | Sunfire C18, 2.1 × 30 mm, 2.5 μm (Waters) | | | |
|---|---|---|---|---|
| Gradient time [min] | % Sol [H2O, 0.1% TFA] | % Sol [Acetonitrile] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

9. PHARMACOLOGICAL TEST METHOD

Ussing Chamber: Mouse kidney M-1 cells were cultivated in DMEM containing 5% FCS and 5 μM dexamethasone for 10 to 12 days on polyester transwell filters. Filters were inserted into a teflon-coated well-plate which fit into the in-house ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode using an in-house built amplifier (Boehringer Ingelheim, Biberach) with the software package Lab View for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as IC50. Results are listed in tables 1 to 5 and further examples listed above.

10. INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways, Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis, asthma, particularly COPD, chronic bronchitis, cystic fibrosis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmacologically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and 1-(2-chloro-4-hydroxyphenyl)-t-butylaminoethanole, (−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate, 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinoline-2-one 4-Hydroxy-7-[2-{[2-{[3-(2-phenylethoxy)propyl] sulfonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino] ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole
5-Hydroxy-8-(1-hydroxy-2-isopropylaminobutyl)-2H-1,4-benzoxazin-3-(4H)-one
1-(4-Amino-3-chloro-5-trifluormethylphenyl)-2-tert.-butylamino)ethanole
6-Hydroxy-8-{1-hydroxy-2-[2-(4-methoxy-phenyl)-1,1-dimethyl-ethylamino]-ethyl}-4H-benzo[1,4]oxazin-3-one
6-Hydroxy-8-{1-hydroxy-2-[2-(4-phenoxy-acetic acid ethylester)-1,1-dimethyl-ethylamino]-ethyl}-4H-benzo[1,4]oxazin-3-one
6-Hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-Dimethyl-2-(2,4,6-trimethylphenyl)-ethylamino]-1-hydroxy-ethyl}-6-hydroxy-4H-benzo[1,4]oxazin-3-one
6-Hydroxy-8-{1-hydroxy-2-[2-(4-hydroxy-phenyl)-1,1-dimethyl-ethylamino]-ethyl}-4H-benzo[1,4]oxazin-3-one
6-Hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-Ethyl-phenyl)-1,1-dimethyl-ethylamino]-1-hydroxy-ethyl}-6-hydroxy-4H-benzo[1,4]oxazin-3-one
8-{2-[2-(4-Ethoxy-phenyl)-1,1-dimethyl-ethylamino]-1-hydroxy-ethyl}-6-hydroxy-4H-benzo[1,4]oxazin-3-one
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-Difluor-phenyl)-1,1-dimethyl-ethylamino]-1-hydroxy-ethyl}-6-hydroxy-4H-benzo[1,4]oxazin-3-one
1-(4-Ethoxy-carbonylamino-3-cyano-5-fluorophenyl)-2-(tert.-butylamino)ethanole
N-[2-Hydroxy-5-(1-hydroxy-2-{2-[4-(2-hydroxy-2-phenyl-ethylamino)-phenyl]-ethylamino}-ethyl)-phenyl]-formamide
8-Hydroxy-5-(1-hydroxy-2-{2-[4-(6-methoxy-biphenyl-3-ylamino)-phenyl]-ethylamino}-ethyl)-1H-quinolin-2-one
8-Hydroxy-5-[1-hydroxy-2-(6-phenethylamino-hexylamino)-ethyl]-1H-quinolin-2-one
5-[2-(2-{4-[4-(2-Amino-2-methyl-propoxy)-phenylamino]-phenyl}-ethylamino)-1-hydroxy-ethyl]-8-hydroxy-1H-quinolin-2-one
[3-(4-{6-[2-Hydroxy-2-(4-hydroxy-3-hydroxymethyl-phenyl)-ethylamino]hexyloxy}-butyl)-5-methyl-phenyl]-urea
4-(2-{6-[2-(2,6-Dichloro-benzyloxy)-ethoxy]-hexylamino}-1-hydroxy-ethyl)-2-hydroxymethyl-phenole
3-(4-{6-[2-Hydroxy-2-(4-hydroxy-3-hydroxymethyl-phenyl)-ethylamino]-hexyloxy}-butyl)-benzenesulfonamide
3-(3-{7-[2-Hydroxy-2-(4-hydroxy-3-hydroxymethyl-phenyl)-ethylamino]-heptyloxy}-propyl)-benzenesulfonamide
4-(2-{6-[4-(3-Cyclopentanesulfonyl-phenyl)-butoxy]-hexylamino}-1-hydroxy-ethyl)-2-hydroxymethyl-phenole
N-Adamantan-2-yl-2-(3-{2-[2-hydroxy-2-(4-hydroxy-3-hydroxymethyl-phenyl)-ethylamino]-propyl}-phenyl)-acetamide
(R,S)-4-(2-{[6-(2,2-Difluoro-4-phenylbutoxy)hexyl]amino}-1-hydroxy-ethyl)-2-(hydroxymethyl)phenole
(R,S)-4-(2-{[6-(2,2-Difluoro-2-phenylethoxy)hexyl]amino}-1-hydroxy-ethyl)-2-(hydroxymethyl)phenole
(R,S)-4-(2-{[4,4-Difluoro-6-(4-phenylbutoxy)hexyl]amino}-1-hydroxy-ethyl)-2-(hydroxymethyl)phenole
(R,S)-4-(2-{[6-(4,4-Difluoro-4-phenylbutoxy)hexyl]amino}-1-hydroxy-ethyl)-2-(hydroxymethyl)phenole
(R,S)-5-(2-{[6-(2,2-Difluoro-2-phenylethoxy)hexyl]amino}-1-hydroxy-ethyl)-8-hydroxyquinolin-2(1H)-one
(R,S)-[2-({6-[2,2-Difluoro-2-(3-methylphenyl)ethoxy]hexyl}amino)-1-hydroxyethyl]-2-(hydroxymethyl)phenole
4-(1R)-2-{[6-(2,2-Difluoro-2-phenylethoxy)hexyl]amino}-1-hydroxyethyl)-2-(hydroxymethyl)phenol
(R,S)-2-(Hydroxymethyl)-4-(1-hydroxy-2-{[4,4,5,5-tetrafluoro-6-(3-phenylpropoxy)-hexyl]amino}ethyl)phenole
(R,S)-[5-(2-{[6-(2,2-Difluoro-2-phenylethoxy)hexyl]amino}-1-hydroxy-ethyl)-2-hydroxyphenyl]formamide
(R,S)-4-2-({6-[2-(3-Bromophenyl)-2,2-difluoroethoxy]hexyl}amino)-1-hydroxyethyl]-2-(hydroxymethyl)phenole
(R,S)-N-[3-(1,1-Difluoro-2-{[6-({2-hydroxy-2-[4-hydroxy-3-(hydroxymethyl)phenyl]-ethyl}amino)hexyl]oxy}ethyl)phenyl]urea
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione
(R,S)-4-[2-({6-[2,2-difluoro-2-(3-methoxyphenyl)ethoxy]hexyl}amino)-1-hydroxyethyl]-2-(hydroxymethyl)phenole
5-((1R)-2-{[6-(2,2-difluoro-2-phenylethoxy)hexyl]amino}-1-hydroxyethyl)-8-hydroxyquinolin-2(1 H)-one
4-((1R)-2-{[4,4-Difluoro-6-(4-phenylbutoxy)hexyl]amino}-1-hydroxy-ethyl)-2-(hydroxymethyl)phenole
(R,S)-4-(2-{[6-(3,3-Difluoro-3-phenylpropoxy)hexyl]amino}-1-hydroxy-ethyl)-2-(hydroxymethyl)phenole
(R,S)-(2-{[6-(2,2-Difluoro-2-phenylethoxy)-4,4-difluorohexyl]amino}-1-hydroxyethyl)-2-(hydroxymethyl)phenole
(R,S)-4-(2-{[6-(2,2-difluoro-3-phenylpropoxy)hexyl]amino}-1-hydroxy ethyl)-2-(hydroxymethyl)phenole
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide
N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide
7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Aclidinium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide 2,2-Diphenylpropionic acid scopine ester-methobromide
2-Fluor-2,2-Diphenylacetic acid scopine ester-methobromide
2-Fluor-2,2-Diphenylacetic acid tropenole ester-methobromide
3,3',4,4'-Tetrafluorbenzil acid tropenole ester-methobromide
3,3',4,4'-Tetrafluorbenzil acid scopine ester-methobromide
4,4'-Difluorbenzil acid tropenole ester-methobromide
4,4'-Difluorbenzil acid scopine ester-methobromide
3,3'-Difluorbenzil acid tropenole ester-methobromide
3,3'-Difluorbenzil acid scopine ester-methobromide
9-Hydroxy-fluorene-9-carbon acid tropenole ester-methobromide
9-Fluor-fluorene-9-carbon acid tropenole ester-methobromide
9-Hydroxy-fluorene-9-carbon acid scopine ester-methobromide
9-Fluor-fluorene-9-carbon acid scopine ester-methobromide
9-Methyl-fluorene-9-carbon acid tropenole ester-methobromide
9-Methyl-fluorene-9-carbon acid scopine ester-methobromide
Benzil acid cyclopropyl tropine ester-methobromide
2,2-Diphenylpropionic acid cyclopropyl tropine ester-methobromide
9-Hydroxy-xanthene-9-carbon acid cyclopropyl tropine ester-methobromide
9-Methyl-fluorene-9-carbon acid cyclopropyl tropine ester-methobromide
9-Methyl-xanthene-9-carbon acid cyclopropyl tropine ester-methobromide
9-Hydroxy-fluorene-9-carbon acid cyclopropyl tropine ester-methobromide
4,4'-Difluorbenzil acid methylester cyclopropyl tropine ester-methobromide
9-Hydroxy-xanthene-9-carbon acid tropenole ester-methobromide
9-Hydroxy-xanthene-9-carbon acid scopine ester-methobromide
9-Methyl-xanthene-9-carbon acid tropenole ester-methobromide
9-Methyl-xanthene-9-carbon acid scopine ester-methobromide
9-Ethyl-xanthene-9-carbon acid tropenole ester-methobromide
9-Difluormethyl-xanthene-9-carbon acid tropenole ester-methobromide
9-Hydroxymethyl-xanthene-9-carbon acid scopine ester-methobromide.

Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, and
{20R-16alpha,17alpha-[butylidenebis(oxy)]-6alpha,9alpha-difluoro-11beta-hydroxy-17beta-(methylthio)androsta-4-en-3-one},
9-fluoro-11beta,17,21-trihydroxy-16alpha-methylpregna-1,4-diene-3,20-dione 21-cyclohexanecarboxylate 17-cyclopropanecarboxylate,
16,17-butylidene dioxy-6,9-difluoro-11-hydroxy-17-(methylthio)androst-4-en-3-one
Flunisolide-21-[4'-(nitrooxymethyl)benzoate]
6,9-Difluoro-17-[(2-furanylcarbonyl)oxy]-11-hydroxy-16-methyl-3-oxo-androsta-1,4-dien-17-carbothion acid (S)-fluoromethylester,
6,9-Difluoro-11-hydroxy-16-methyl-3-oxo-17-propionyloxy-androsta-1,4-dien-17-carbothion acid (S)-(2-oxo-tetrahydro-furan-3S-yl)ester, and
6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester optionally in racemic form, as enantiomers, diastereomers or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibtors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and
5-[(N-(2,5-dichloro-3-pyridinyl)-carboxamide]-8-methoxyquinoline
5-[N-(3,5-dichloro-1-oxido-4-pyridinyl)-carboxamide]-8-methoxy-2-(trifluoromethyl)-quinoline
N-(3,5-dichloropyrid-4-yl)-[1-(4-fluorobenzyl)-5-hydroxy-indole-3-yl]glyoxyl acid amide), 9-[(2-fluorophenyl)methyl]-N-methyl-2-(trifluoromethyl)-9H-purine-6-amine
4-[(2R)-2-[3-(cyclopentyloxy)-4-methoxyphenyl]-2-phenylethyl]-pyridine,
N-[(3R)-3,4,6,7-tetrahydro-9-methyl-4-oxo-1-phenylpyrrolo[3,2,1-jk][1,4]benzodiazepin-3-yl]-4-Pyridinecarboxamide,
4-[6,7-diethoxy-2,3-bis(hydroxymethyl)-1-naphthalenyl]-1-(2-methoxyethyl)-2(1H)-pyridinone,
2-[4-[6,7-diethoxy-2,3-bis(hydroxymethyl)-1-naphthalenyl]-2-pyridinyl]-4-(3-pyridinyl)-1(2H)-Phthalazinone,
(3-(3-cyclopenyloxy-4-methoxybenzyl)-6-ethylamino-8-isopropyl-3H-purine,
beta-[3-(cyclopentyloxy)-4-methoxyphenyl]-1,3-dihydro-1,3-dioxo-2H-isoindole-2-propanamide,
9-ethyl-2-methoxy-7-methyl-5-propyl-imidazo[1,5-a]pyrido[3,2-e]pyrazin-6(5H)-one
5-[3-(cyclopentyloxy)-4-methoxyphenyl]-3-[(3-methylphenyl)methyl] (3S,5S)-2-piperidinone,
4-[1-[3,4-bis(difluoromethoxy)phenyl]-2-(3-methyl-1-oxido-4-pyridinyhethyl]-alpha,alpha-bis(trifluoromethyl)-Benzenemethanol
N-(3,5-Dichloro-1-oxo-pyridine-4-yl)-4-difluoromethoxy-3-cyclopropylmethoxybenzamide
(−)p-[(4aR*,10bS*)-9-Ethoxy-1,2,3,4,4a,10b-hexahydro-8-methoxy-2-methylbenzo[s][1,6]naphthyridin-6-yl]N,N-diisopropylbenzamide
(R)-(+)-1-(4-Bromobenzyl)-4-[(3-cyclopentyloxy)-4-methoxyphenyl]-2-pyrrolidone
3-(Cyclopentyloxy-4-methoxyphenyl)-1-(4-N'-[N-2-cyano-5-methyl-isothioureido]benzyl)-2-pyrrolidone
cis[4-Cyano-4-(3-cyclopentyloxy-4-methoxyphenyl)cyclohexan-1-carbon acid]
2-carbomethoxy-4-cyano-4-(3-cyclopropylmethoxy-4-difluoromethoxyphenyl)cyclohexan-1-one
cis[4-Cyano-4-(3-cyclopropylmethoxy-4-difluoromethoxyphenyl)cyclohexan-1-ol]
(R)-(+)-Ethyl[4-(3-cyclopentyloxy-4-methoxyphenyl)pyrrolidine-2-yliden]acetate
(S)-(−)-Ethyl[4-(3-cyclopentyloxy-4-methoxyphenyl)pyrrolidine-2-yliden]acetate 9-Cyclopentyl-5,6-dihydro-7-ethyl-3-(2-thienyl)-9H-pyrazolo[3,4-c]-1,2,4-triazolo[4,3-a]pyridine 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukast, Pranlukast, Zafirlukast, Masikulast, L-733321 (see compound 2ab of D. Guay et al, Bioorg. Med. Chem. Lett. 8 (1998) 453-458) and (E)-8-[2-[4-[4-(4-Fluorophenyl)butoxy]phenyl]ethenyl]-2-(1H-tetrazole-5-yl)-4H-1-benzopyran-4-one (MEN-91507)

4-[6-Acetyl-3-[3-(4-acetyl-3-hydroxy-2-propylphenylthio) propoxy]-2-propylphenoxy]-butyric acid (MN-001)

1-(((R)-(3-(2-(6,7-Difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid

[2-[[2-(4-tert-Butyl-2-thiazolyl)-5-benzofuranyl]oxymethyl]phenyl]acetic acid optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximab, Trastuzumab, Panitumumab Gefitinib, Canertinib, Erlotinib, Mab ICR-62 and 4-[(3-Chlor-4-fluorphenyl)amino]-6-{[4-(morpholine-4-yl)-1-oxo-2-butene-1-yl]amino}-7-cyclopropylmethoxy-quinazoline 4-[(3-Chlor-4-fluorphenyl)amino]-6-{[4-(N,N-diethylamino)-1-oxo-2-butene-1-yl]amino}-7-cyclopropyl-methoxy-quinazoline 4-[(3-Chlor-4-fluorphenyl)amino]-6-{[4-(N,N-dimethylamino)-1-oxo-2-butene-1-yl]amino}-7-cyclopropyl-methoxy-quinazoline 4-[(R)-(1-Phenyl-ethyl)amino]-6-{[4-(morpholine-4-yl)-1-oxo-2-butene-1-yl]amino}-7-cyclopentyloxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-cyclopropylmethoxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline 4-[(3-Chlor-4-fluor-phenyl)amino]-6-{[4-((R)-2-methoxymethyl-6-oxo-morpholine-4-yl)-1-oxo-2-butene-1-yl]amino}-7-cyclopropylmethoxy-quinazoline 4-[(3-Chlor-4-fluor-phenyl)amino]-6-[2-((S)-6-methyl-2-oxo-morpholine-4-yl)-ethoxy]-7-methoxy-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopentyloxy-quinazoline 4-[(R)-(1-Phenyl-ethyl)amino]-6-{[4-(N,N-bis-(2-methoxy-ethyl)-amino]-1-oxo-2-butene-1-yl]amino}-7-cyclopropylmethoxy-quinazoline 4-[(R)-(1-Phenyl-ethyl)amino]-6-({4-[N-(2-methoxy-ethyl)-N-ethyl-amino]-1-oxo-2-butene-1-yl}amino)-7-cyclopropylmethoxy-quinazoline 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-((R)-tetrahydrofuran-3-yloxy)-quinazoline 4-[(3-Chlor-4-fluorphenyl)amino]-6-{[4-(N,N-dimethylamino)-1-oxo-2-butene-1-yl]amino}-7-((S)-tetrahydrofuran-3-yloxy)-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopentyloxy-quinazoline 4-[(3-Chlor-4-fluorphenyl)amino]-6-{[4-(N-cyclopropyl-N-methyl-amino)-1-oxo-2-butene-1-yl]amino}-7-cyclopentyloxy-quinazoline 4-[(3-Chlor-4-fluorphenyl)amino]-6-{[4-(N,N-dimethylamino)-1-oxo-2-butene-1-yl]amino}-7-[(R)-(tetrahydrofuran-2-yl)methoxy]quinazoline 4-[(3-Chlor-4-fluorphenyl)amino]-6-{[4-(N,N-dimethylamino)-1-oxo-2-butene-1-yl]amino}-7-[(S)-(tetrahydrofuran-2-yl)methoxy]-quinazoline 4-[(3-Ethinyl-phenyl)amino]-6,7-bis-(2-methoxy-ethoxy)-quinazoline 4-[(3-Chlor-4-fluorphenyl)amino]-7-[3-(morpholine-4-yl)-propyloxy]-6-[(vinylcarbonyl)amino]-quinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-butene-1-yl]amino}-7-ethoxyquinoline 4-{[3-Chlor-4-(3-fluor-benzyloxy)-phenyl]amino}-6-(5-{[(2-methansulfonyl-ethyl)amino]methyl}-furan-2-yl) quinazoline 4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorphenyl)amino]-6-{[4-(morpholine-4-yl)-1-oxo-2-butene-1-yl]amino}-7-[(tetrahydrofuran-2-yl)methoxy]-quinazoline 4-[(3-Chlor-4-fluorphenyl)amino]-6-({4-[N,N-bis-(2-methoxy-ethyl)-amino]-1-oxo-2-butene-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-butene-1-yl]amino}-quinazoline 4-[(3-Chlor-4-fluor-phenyl)amino]-6-[2-(2,2-dimethyl-6-oxo-morpholine-4-yl)-ethoxy]-7-methoxy-quinazoline 4-[(3-Chlor-4-fluor-phenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluor-phenyl)amino]-7-[2-(2,2-dimethyl-6-oxo-morpholine-4-yl)-ethoxy]-6-[(S)-(tetrahydrofuran-2-yl)methoxy]-quinazoline
4-[(3-Chlor-4-fluor-phenyl)amino]-6-{2-[4-(2-oxo-morpholine-4-yl)-piperidin-1-yl]-ethoxy}-7-methoxy-quinazoline
4-[(3-Chlor-4-fluor-phenyl)amino]-6-[1-(tert.-butyloxycarbonyl)-piperidine-4-yloxy]-7-methoxy-quinazoline
4-[(3-Chlor-4-fluor-phenyl)amino]-6-(trans-4-amino-cyclohexane-1-yloxy)-7-methoxy-quinazoline
4-[(3-Chlor-4-fluor-phenyl)amino]-6-(trans-4-methansulfonylamino-cyclohexane-1-yloxy)-7-methoxy-quinazoline
4-[(3-Chlor-4-fluor-phenyl)amino]-6-(tetrahydropyran-3-yloxy)-7-methoxy-quinazoline
4-[(3-Chlor-4-fluor-phenyl)amino]-6-(1-methyl-piperidine-4-yloxy)-7-methoxy-quinazoline
4-[(3-Chlor-4-fluor-phenyl)amino]-6-{1-[(morpholine-4-yl)carbonyl]-piperidine-4-yloxy}-7-methoxy-quinazoline
4-[(3-Chlor-4-fluor-phenyl)amino]-6-{1-[(methoxymethyl)carbonyl]-piperidine-4-yloxy}-7-methoxy-quinazoline
4-[(3-Chlor-4-fluor-phenyl)amino]-6-(piperidine-3-yloxy)-7-methoxy-quinazoline
4-[(3-Chlor-4-fluor-phenyl)amino]-6-[1-(2-acetylamino-ethyl)-piperidine-4-yloxy]-7-methoxy-quinazoline
4-[(3-Chlor-4-fluor-phenyl)amino]-6-(tetrahydropyran-4-yloxy)-7-ethoxy-quinazoline
4-[(3-Chlor-4-fluor-phenyl)amino]-6-((S)-tetrahydrofuran-3-yloxy)-7-hydroxy-quinazoline
4-[(3-Chlor-4-fluor-phenyl)amino]-6-(tetrahydropyran-4-yloxy)-7-(2-methoxy-ethoxy)-quinazoline
4-[(3-Chlor-4-fluor-phenyl)amino]-6-{trans-4-[(dimethylamino)sulfonylamino]-cyclohexane-1-yloxy}-7-methoxy-quinazoline
4-[(3-Chlor-4-fluor-phenyl)amino]-6-{trans-4-[(morpholine-4-yl)carbonylamino]-cyclohexane-1-yloxy}-7-methoxy-quinazoline
4-[(3-Chlor-4-fluor-phenyl)amino]-6-{trans-4-[(morpholine-4-yl)sulfonylamino]-cyclohexane-1-yloxy}-7-methoxy-quinazoline
4-[(3-Chlor-4-fluor-phenyl)amino]-6-(tetrahydropyran-4-yloxy)-7-(2-acetylamino-ethoxy)-quinazoline
4-[(3-Chlor-4-fluor-phenyl)amino]-6-(tetrahydropyran-4-yloxy)-7-(2-methansulfonylamino-ethoxy)-quinazoline
4-[(3-Chlor-4-fluor-phenyl)amino]-6-{1-[(piperidine-1-yl)carbonyl]-piperidine-4-yloxy}-7-methoxy-quinazoline
4-[(3-Chlor-4-fluor-phenyl)amino]-6-(1-aminocarbonylmethyl-piperidine-4-yloxy)-7-methoxy-quinazoline
4-[(3-Chlor-4-fluor-phenyl)amino]-6-(cis-4-{N-[(tetrahydropyran-4-yl)carbonyl]-N-methyl-amino}-cyclohexane-1-yloxy)-7-methoxy quinazoline
4-[(3-Chlor-4-fluor-phenyl)amino]-6-(cis-4-{N-[(morpholine-4-yl)carbonyl]-N-methyl-amino}-cyclohexane-1-yloxy)-7-methoxy-quinazoline
4-[(3-Chlor-4-fluor-phenyl)amino]-6-(cis-4-{N-[(morpholine-4-yl)sulfonyl]-N-methyl-amino}-cyclohexane-1-yloxy)-7-methoxy-quinazoline
4-[(3-Chlor-4-fluor-phenyl)amino]-6-(trans-4-ethansulfonylamino-cyclohexane-1-yloxy)-7-methoxy-quinazoline
4-[(3-Chlor-4-fluor-phenyl)amino]-6-(1-methansulfonyl-piperidine-4-yloxy)-7-ethoxy-quinazoline
4-[(3-Chlor-4-fluor-phenyl)amino]-6-(1-methansulfonyl-piperidine-4-yloxy)-7-(2-methoxy-ethoxy)-quinazoline
4-[(3-Chlor-4-fluor-phenyl)amino]-6-[1-(2-methoxy-acetyl)-piperidine-4-yloxy]-7-(2-methoxy-ethoxy)-quinazoline
4-[(3-Chlor-4-fluor-phenyl)amino]-6-(cis-4-acetylamino-cyclohexane-1-yloxy)-7-methoxy-quinazoline
4-[(3-Ethinyl-phenyl)amino]-6-[1-(tert-butyloxycarbonyl)-piperidine-4-yloxy]-7-methoxy-quinazoline
4-[(3-Ethinyl-phenyl)amino]-6-(tetrahydropyran-4-yloxy]-7-methoxy-quinazoline
4-[(3-Chlor-4-fluor-phenyl)amino]-6-(cis-4-{N-[(piperidine-1-yl)carbonyl]-N-methyl-amino}-cyclohexane-1-yloxy)-7-methoxy-quinazoline
4-[(3-Chlor-4-fluor-phenyl)amino]-6-(cis-4-{N-[4-methyl-piperazine-1-yl)carbonyl]-N-methyl-amino}-cyclohexane-1-yloxy)-7-methoxy-quinazoline
4-[(3-Chlor-4-fluor-phenyl)amino]-6-{cis-4-[(morpholine-4-yl)carbonylamino]-cyclohexane-1-yloxy}-7-methoxy-quinazoline
4-[(3-Chlor-4-fluor-phenyl)amino]-6-{1-[2-(2-oxopyrrolidine-1-yl)ethyl]-piperidine-4-yloxy}-7-methoxy-quinazoline
4-[(3-Chlor-4-fluor-phenyl)amino]-6-{1-[(morpholine-4-yl)carbonyl]-piperidine-4-yloxy}-7-(2-methoxy-ethoxy)-quinazoline
4-[(3-Ethinyl-phenyl)amino]-6-(1-acetyl-piperidine-4-yloxy)-7-methoxy-quinazoline
4-[(3-Ethinyl-phenyl)amino]-6-(1-methyl-piperidine-4-yloxy)-7-methoxy-quinazoline
4-[(3-Ethinyl-phenyl)amino]-6-(1-methansulfonyl-piperidine-4-yloxy)-7-methoxy-quinazoline
4-[(3-Chlor-4-fluor-phenyl)amino]-6-(1-methyl-piperidine-4-yloxy)-7(2-methoxy-ethoxy)-quinazoline
4-[(3-Chlor-4-fluor-phenyl)amino]-6-(1-isopropyloxycarbonyl-piperidine-4-yloxy)-7-methoxy-quinazoline
4-[(3-Chlor-4-fluor-phenyl)amino]-6-(cis-4-methylamino-cyclohexane-1-yloxy)-7-methoxy-chinazoline
4-[(3-Chlor-4-fluor-phenyl)amino]-6-{cis-4-[N-(2-methoxy-acetyl)-N-methyl-amino]-cyclohexane-1-yloxy}-7-methoxy-quinazoline
4-[(3-Ethinyl-phenyl)amino]-6-(piperidine-4-yloxy)-7-methoxy-quinazoline
4-[(3-Ethinyl-phenyl)amino]-6-[1-(2-methoxy-acetyl)-piperidine-4-yloxy]-7-methoxy-quinazoline
4-[(3-Ethinyl-phenyl)amino]-6-{1-[(morpholine-4-yl)carbonyl]-piperidine-4-yloxy}-7-methoxy-quinazoline
4-[(3-Chlor-4-fluor-phenyl)amino]-6-{1-[(cis-2,6-dimethyl-morpholine-4-yl)carbonyl]-piperidine-4-yloxy}-7-methoxy-quinazoline
4-[(3-Chlor-4-fluor-phenyl)amino]-6-{1-[(2-methyl-morpholine-4-yl)carbonyl]-piperidine-4-yloxy}-7-methoxy-quinazoline
4-[(3-Chlor-4-fluor-phenyl)amino]-6-{1-[(S,S)-(2-oxa-5-aza-bicyclo[2.2.1]hept-5-yl)carbonyl]-piperidine-4-yloxy}-7-methoxy-quinazoline
4-[(3-Chlor-4-fluor-phenyl)amino]-6-{1-[(N-methyl-N-2-methoxyethyl-amino)carbonyl]-piperidine-4-yloxy}-7-methoxy-quinazoline
4-[(3-Chlor-4-fluor-phenyl)amino]-6-(1-ethyl-piperidine-4-yloxy)-7-methoxy-quinazoline
4-[(3-Chlor-4-fluor-phenyl)amino]-6-{1-[(2-methoxyethyl)carbonyl]-piperidine-4-yloxy}-7-methoxy-quinazoline
4-[(3-Chlor-4-fluor-phenyl)amino]-6-{1-[(3-methoxypropyl-amino)-carbonyl]-piperidine-4-yloxy}-7-methoxy-quinazoline
4-[(3-Chlor-4-fluor-phenyl)amino]-6-[cis-4-(N-methansulfonyl-N-methyl-amino)-cyclohexane-1-yloxy]-7-methoxy-quinazoline
4-[(3-Chlor-4-fluor-phenyl)amino]-6-[cis-4-(N-acetyl-N-methyl-amino)-cyclohexane-1-yloxy]-7-methoxy-quinazoline
4-[(3-Chlor-4-fluor-phenyl)amino]-6-(trans-4-methylamino-cyclohexane-1-yloxy)-7-methoxy-quinazoline 4-[(3-Chlor-4-fluor-phenyl)amino]-6-[trans-4-(N-methansulfonyl-N-methyl-amino)-cyclohexane-1-yloxy]-7-methoxy-quinazoline 4-[(3-Chlor-4-fluor-phenyl)amino]-6-(trans-4-dimethylamino-cyclohexane-1-yloxy)-7-methoxy-quinazoline 4-[(3-Chlor-4-fluor-phenyl)amino]-6-(trans-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-[2-(2,2-dimethyl-6-oxo-morpholine-4-yl)-ethoxy]-7-[(S)-(tetrahydrofuran-2-yl)methoxy]-quinazoline 4-[(3-Chlor-4-fluor-phenyl)amino]-6-(1-methansulfonyl-piperidine-4-yloxy)-7-methoxy-quinazoline 4-[(3-Chlor-4-fluor-phenyl)amino]-6-(1-cyano-piperidine-4-yloxy)-7-methoxy-quinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred dopamine antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred PAF antagonists which may be mentioned include Lexipafante and 4-(2-Chlorphenyl)-9-methyl-2-[3(4-morpholinyl)-3-propanone-1-yl]-6H-thieno-[3,2-f]-[1,2,4]triazolo[4,3-a][1,4]diazepine 6-(2-Chlorphenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinypethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409), optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred MRP4 inhibitors which may be mentioned include N-Acetyl-dinitrophenyl-Cysteine, cGMP, Cholate, Diclofenac, Dehydroepiandrosterone 3-glucuronide, Dehydroepiandrosterone 3-sulfate, Dilazep, Dinitrophenyl-S-glutathione, Estradiol 17-beta-glucuronide, Estradiol 3,17-disulfate, Estradiol 3-glucuronide, Estradiol 3-sulfate, Estrone 3-sulfate, Flurbiprofen, Folate, N5-formyl-tetrahydrofolate, Glycocholate, Glycolithocholic acid sulfate, Ibuprofen, Indomethacin, Indoprofen, Ketoprofen, Lithocholic acid sulfate, Methotrexate, (E)-3-[[[3-[2-(7-Chloro-2-quinolinypethenyl]phenyl]-[[3-dimethylamino)-3-oxopropyl]thio]methyl]thio]-propanoic acid alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulfate, Topotecan, Trequinsin, Zaprinast and Dipyridamol, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred iNOS-Inhibitors which may be mentioned include S-(2-Aminoethyl)isothio-urea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA ($N^{\omega}$-Nitro-L-arginin), L-NAME ($N^{\omega}$-Nitro-L-argininmethylester), L-NMMA ($N^{\omega}$-Monomethyl-L-arginin), L-NIO ($N^{\omega}$-Iminoethyl-L-ornithin), L-NIL ($N^{\omega}$-iminoethyl-lysin), (S)-6-Acetimidoylamino-2-aminohexanoic acid (1H-tetrazole-5-yl)-amide N-[[3-(aminomethyl)phenyl]methyl]-ethanimidamide, (S)-4-(2-acetimidoylamino-ethylsulfanyl)-2-amino-buturic acid, 2-[2-(4-Methoxy-pyridine-2-yl)-ethyl]-3H-imidazo[4,5-b]pyridine, 2-((R)-3-amino-1-phenyl-propoxy)-4-chlor-5-fluorbenzonitrile, 2-((1R,3S)-3-amino-4-hydroxy-1-thiazole-5-yl-butylsulfanyl)-6-trifluoromethyl-nicotinonitrile, 2-((1R,3S)-3-amino-4-hydroxy-1-thiazole-5-yl-butylsulfanyl)-4-chlor-benzonitrile, 2-((1R,3S)-3-amino-4-hydroxy-1- thiazole-5-yl-butylsulfanyl)-5-chlor-benzonitrile, (2S,4R)-2-amino-4-(2-chlor-5-trifluoromethyl-phenylsulfanyl)-4-thiazole-5-yl-butane-1-ol, 2-((1R,3S)-3-amino-4-hydroxy-1-thiazole-5-yl-butylsulfanyl)-5-chlor-nicotinonitrile, 4-((S)-3-amino-4-hydroxy-1-phenyl-butylsulfanyl)-6-methoxy-nicotinonitrile and substituted 3-phenyl-3,4-dihydro-1-isoquinolinamine as for instance 1S,5S,6R)-7-Chlor-5-methyl-2-aza-bicyclo[4.1.0]hept-2-ene-3-ylamin (4R,5R)-5-Ethyl-4-methyl-thiazolidine-2-ylideneamine, (1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethyl-phenoxy)-ethoxy]-2-phenyl-pyridine, 3-{[(Benzo[1,3]dioxol-5-ylmethyl)-carbamoyl]-methyl}-4-(2-imidazole-1-yl-pyrimidine-4-yl)-piperazine-1-carbon acid methylester, (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Further examples of preferred iNOS-Inhibitors which may be mentioned include antisense-Oligonucleotide, especially those antisense-Oligonucleotide bindung iNOS-coding nucleinic acids, examples therefore are disclosed in WO 01/52902.

Examples of preferred SYK-inhibitors which may be mentioned include
2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5-yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propanediamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propanediamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenylmethyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamin,
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;

N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;
[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred cystic fibrosis transmembrane regulators (CFTR) and CFTR potentiators which may be mentioned include, preferably VX-770 and VX-809

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulfuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or is prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation 1 capsule contains:

| active substance | 0.5 mg |
|---|---|
| lactose for inhalation | 5.0 mg |
| | 5.5 mg |

Preparation

The active substance is mixed with lactose for inhalation. The mixture is packed into capsules in a capsule-making machine (weight of the empty capsule approx. 50 mg).

| weight of capsule: | 55.5 mg |
|---|---|
| size of capsule = | 3 |

The invention claimed is:

1. A compound of formula (I)

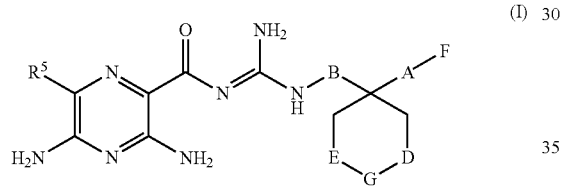

(I)

wherein

A denotes a bond or is selected from the group consisting of O, —$CH_2$—, —$CH_2CH_2$—, —$CH_2CH_2CH_2$—, —$CH_2$—O—, —$CH_2$—$NR^{41}$— and —$NR^{41}$—, wherein $R^{41}$ denotes hydrogen or $C_{1-6}$-alkyl, B denotes —$CH_2$— or —$CH_2CH_2$—, or provided that A is not O or —$NR^{41}$, B denotes a bond D, E denote independently from each other a bond or —$CH_2$—, F denotes optionally substituted aryl, or optionally substituted heteroaryl, G denotes a group of formula (g.1), (g.2) or (g.3)

(g.1)

(g.2)

(g.3)

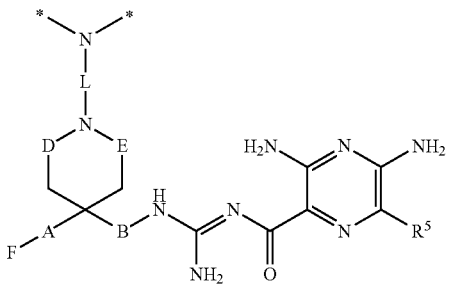

wherein $R^1$ is selected from the group consisting of hydrogen, $C_{1-6}$alkyl, optionally substituted piperidinyl-CO—, optionally substituted piperazinyl-CO—, $R^{1.1}$—$SO_2$—, $R^{1.2}$—$C_{2-4}$-alkyl-NH—CO—, $H_3C$—NH—CO—, $R^{1.2.4}$—O—CO—$CH_2$—NH—CO—, $R^{1.2}$—$C_{2-4}$-alkyl-N($C_{1-4}$-alkyl)-CO—, $H_3C$ -N($C_{1-4}$-alkyl)-CO—, $R^{1.2.4}$—O—CO—$CH_2$—N($C_{1-4}$-alkyl)-CO—, $R^{1.3}$—$C_{1-6}$-alkyl-CO—, $R^{1.4}$—$C_{2-6}$-alkyl-, optionally substituted phenyl-$CH_2$—, $R^{1.4.3}$—O—CO—$CH_2$—, HO—CO—$CH_2$— and $HOSO_2$—$CH_2$—, $R^{1.5}$—$C_{1-6}$-alkyl-CO— and $R^{1.6}$—C(NH)—, wherein $R^{1.1}$ is selected from the group consisting of $C_{1-4}$-alkyl-, $H_2NC(NH)NH$—$C_{1-6}$-alkyl-, $R^{1.2.1}R^{1.2.2}N$—$C_{1-4}$-alkyl-, $R^{1.2.1}R^{1.2.2}R^{1.2.3}N^+$—$C_{1-4}$-alkyl, HOCO—$C_{1-4}$-alkyl- and $C_{1-3}$-alkyl-OCO—$C_{1-4}$-alkyl-, $R^{1.2}$ is selected from the group consisting of hydrogen, $H_2NC(NH)NH$—, $R^{1.2.1}R^{1.2.2}N$—, $R^{1.2.1}R^{1.2.2}R^{1.2.3}N^+$—, $R^{1.2.3}$—HN—C($NR^{1.2.3}$)—NH—, $R^{1.2.4}$—O—CO—, $R^{1.2.5}$—O—CO—NH— and HO—CO—, $HOSO_2$—, wherein $R^{1.2.1}$ denotes hydrogen or $C_{1-6}$-alkyl, $R^{1.2.2}$ denotes hydrogen or $C_{1-6}$-alkyl, or $R^{1.2.1}$ and $R^{1.2.2}$ together form a 4- to 7- membered heterocyclic ring containing one N-atom, $R^{1.2.3}$ denotes hydrogen or $C_{1-6}$-alkyl, $R^{1.2.4}$ denotes hydrogen or $C_{1-6}$-alkyl, $R^{1.2.5}$ denotes hydrogen or $C_{1-6}$-alkyl, $R^{1.3}$ is selected from the group consisting of hydrogen, $C_{1-6}$-alkyl, $C_{1-6}$-alkyl-O—, optionally substituted phenyl, $R^{1.3.1}R^{1.3.2}N$—, $R^{1.2.1}R^{1.2.2}R^{1.2.3}N^+$—, $R^{1.2.3}$—HN—C($NR^{1.2.3}$)—NH—, $H_2NC(NH)NH$—, $R^{1.2.4}$—O—CO—, HO—CO— and $HOSO_2$—, wherein $R^{1.3.1}$ denotes hydrogen or $C_{1-6}$-alkyl, $R^{1.3.2}$ denotes hydrogen or $C_{1-6}$-alkyl, or $R^{1.3.1}$ and $R^{1.3.2}$ together form a 4- to 7- membered hetercyclic ring containing one N-atom, $R^{1.4}$ is selected from the group consisting of hydrogen, $R^{1.4.1}R^{1.4.2}N$—, $R^{1.4.1}R^{1.4.2}R^{1.4.3}N^+$—, $H_2N$—C(NH)—NH—, $R^{1.4.3}$—HN—C($NR^{1.4.4}$)—NH—, optionally substituted phenyl, $R^{1.4.3}$—O—CO—, $R^{1.4.4}$—O—CO—NH—, HO—CO— and $HOSO_2$—, wherein $R^{1.4.1}$ denotes hydrogen or $C_{1-6}$-alkyl, $R^{1.4.2}$ denotes hydrogen or $C_{1-6}$-alkyl, $R^{1.4.3}$ denotes hydrogen or $C_{1-6}$-alkyl, $R^{1.4.4}$ denotes hydrogen or $C_{1-6}$-alkyl, $R^{1.5}$ is selected from the group consisting of hydrogen, $C_{1-6}$-alkyl-O—,
$R^{1.5.1}R^{1.5.2}N$—, $R^{1.5.1}R^{1.5.2}R^{1.5.3}N^+$—, $H_2N$—C(NH)—NH—, optionally substituted phenyl, $R^{1.5.3}$—O—CO—, $R^{1.5.4}$—O—CO—NH—, HO—CO— and $HOSO_2$—,
wherein
$R^{1.5.1}$ denotes hydrogen or $C_{1-6}$-alkyl,
$R^{1.5.2}$ denotes hydrogen or $C_{1-6}$-alkyl,
$R^{1.5.3}$ denotes hydrogen or $C_{1-6}$-alkyl,
$R^{1.5.4}$ denotes hydrogen or $C_{1-6}$-alkyl,
$R^{1.6}$ denotes $R^{1.6.1}R^{1.6.2}N$—,
wherein
$R^{1.6.1}$ denotes hydrogen or $C_{1-6}$-alkyl;
$R^{1.6.2}$ denotes hydrogen or $C_{1-6}$-alkyl;
$R^{1b}$ is selected from the group consisting of $C_{1-4}$-alkyl, $R^{1.4}$—$C_{2-6}$-alkyl-, optionally substituted phenyl-$CH_2$—, $R^{1.4.3}$—O—CO—$CH_2$— and HO—CO—$CH_2$—
$R^{1s}$ denotes $C_{1-6}$-alkyl,
$X^-$ denotes any anion forming a pharmaceutically acceptable salt,
L denotes a bridging group —CO—NH—$C_{2-6}$-alkyl-NH—CO—, —$COC_{1-6}$-alkyl-CO—, —$C_{2-6}$-alkyl-,
forming a compound of formula (IC),
whereby the molecular entities of formula (IC) connected by L may be identical or different

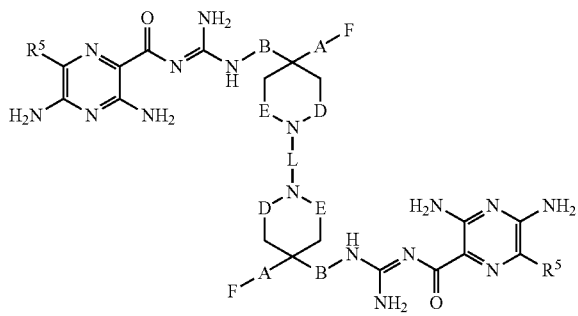

(IC)

$R^5$ denotes Cl or Br,
and the pharmacologically acceptable acid addition salts thereof.

2. The compound of formula (IA), (IB) or (IC.1) according to claim 1, characterized in that

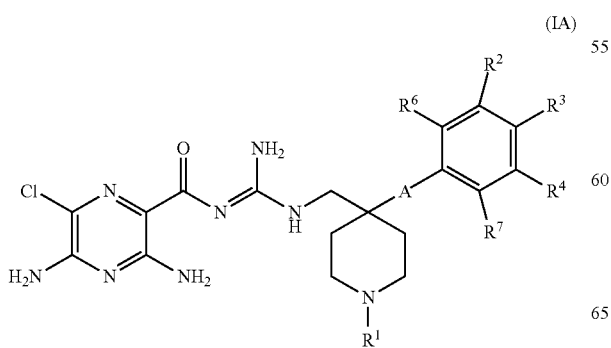

(IA)

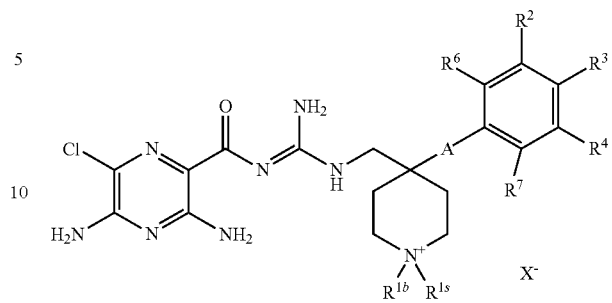

(IB)

A denotes a bond, —$CH_2$— or —$CH_2CH_2$—, —CH2—O—,
$R^1$ is selected from the group consisting of
hydrogen, $C_{1-6}$alkyl, $R^{1.1}$—$SO_2$—, $R^{1.2}$—$C_{2-4}$-alkyl-NH—CO—, $H_3C$—NH—CO—, $R^{1.2.4}$—O—CO—$CH_2$—NH—CO—, $R^{1.2}$—$C_{2-4}$-alkyl-N($C_{1-4}$-alkyl)-CO—, $H_3C$—N($C_{1-4}$-alkyl)-CO—, $R^{1.2.4}$—O—CO—$CH_2$—N($C_{1-4}$-alkyl)-CO—, $R^{1.3}$—$C_{1-6}$-alkyl-CO—, $R^{1.4}$—$C_{2-6}$-alkyl-, optionally substituted phenyl-$CH_2$—, $R^{1.4.3}$—O—CO—$CH_2$—, $C_{1-6}$-alkyl-CO—, HO—CO—$CH_2$— and $HOSO_2$—$CH_2$—, $R^{1.5}$—$C_{1-6}$-alkyl-CO— and $R^{1.6}$—C(NH)—,
wherein
$R^{1.1}$ denotes $C_{1-4}$-alkyl-;
$R^{1.2}$ is selected from the group consisting of
hydrogen, $R^{1.2.1}R^{1.2.2}N$—, $R^{1.2.1}R^{1.2.2}R^{1.2.3}N^+$—, $R^{1.2.4}$—O—CO—, HO—CO— and $R^{1.2.5}$—O—CO—NH—,
wherein
$R^{1.2.1}$ denotes hydrogen or $C_{1-6}$-alkyl,
$R^{1.2.2}$ denotes hydrogen or $C_{1-6}$-alkyl,
$R^{1.2.3}$ denotes hydrogen or $C_{1-6}$-alkyl,
$R^{1.2.4}$ denotes $C_{1-6}$-alkyl,
$R^{1.2.5}$ denotes $C_{1-6}$-alkyl,
$R^{1.3}$ is selected from the group consisting of hydrogen, $C_{1-6}$-alkyl, $C_{1-6}$-alkyl-O—, and optionally substituted phenyl
$R^{1.4}$ is selected from the group consisting of hydrogen, $R^{1.4.1}R^{1.4.2}N$—, $R^{1.4.1}R^{1.4.2}R^{1.4.3}N^+$—, $H_2N$—C(NH)—NH—, $R^{1.4.3}$—HN—C($NR^{1.4.4}$)—NH—, optionally substituted phenyl, $R^{1.4.3}$—O—CO—, $R^{1.4.4}$—O—CO—NH—, HO—CO— and $HOSO_2$—,
wherein
$R^{1.4.1}$ denotes hydrogen or $C_{1-6}$-alkyl,
$R^{1.4.2}$ denotes hydrogen or $C_{1-6}$-alkyl,
$R^{1.4.3}$ denotes hydrogen or $C_{1-6}$-alkyl,
$R^{1.4.4}$ denotes hydrogen or $C_{1-6}$-alkyl,
$R^{1.5}$ is selected from the group consisting of hydrogen, $C_{1-6}$-alkyl-O—, $R^{1.5.1}R^{1.5.2}N$—, $R^{1.2.1}R^{1.2.2}R^{1.2.3}N^+$—, $H_2N$—C(NH)—NH—, $R^{1.5.3}$—O—CO—, $R^{1.5.4}$—O—CO—NH—, optionally substituted phenyl,
wherein
$R^{1.5.1}$ denotes hydrogen or $C_{1-6}$-alkyl,
$R^{1.5.2}$ denotes hydrogen or $C_{1-6}$-alkyl,
$R^{1.5.3}$ denotes hydrogen or $C_{1-6}$-alkyl,
$R^{1.5.4}$ denotes hydrogen or $C_{1-6}$-alkyl,
$R^{1.6}$ denotes of $R^{1.6.1}R^{1.6.2}N$—, wherein
$R^{1.6.1}$ denotes hydrogen or $C_{1-6}$-alkyl;
$R^{1.6.2}$ denotes hydrogen or $C_{1-6}$-alkyl,
$R^{1b}$ is selected from the group consisting of $C_{1-4}$-alkyl,
$R^{1s}$ denotes $C_{1-6}$-alkyl,
$X^-$ denotes any anion forming a pharmaceutically acceptable salt,
L denotes a bridging group —CO—NH—$C_{2-6}$-alkyl-NH—CO—, —COC$_{1-6}$-alkyl-CO— or —$C_{2-6}$-alkyl-, forming a compound of formula (IC.1),
whereby the molecular entities of formula (IC.1) connected by L may be identical or different

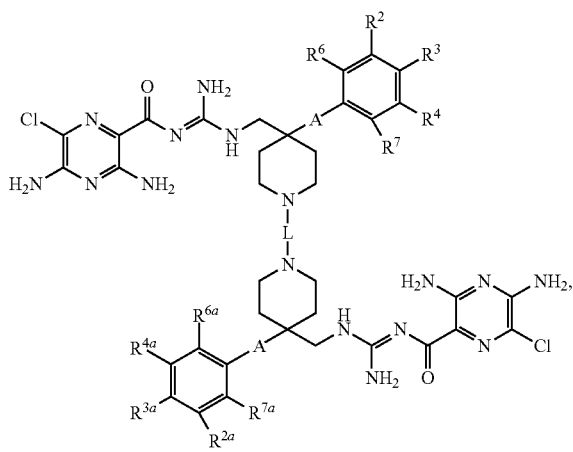

(IC.1)

$R^2$, $R^3$, $R^4$, $R^6$, $R^7$, $R^{2a}$, $R^{3a}$, $R^{4a}$, $R^{6a}$, $R^{7a}$ independently from each other are selected from the group consisting of hydrogen, halogen, CN, $C_{1-4}$alkyl, $C_{1-3}$-alkyl-O—, $C_{1-3}$-alkyl-OCO—, —COOR$^{4.1}$, —CONR$^{4.2}$R$^{4.3}$ and —OR$^{4.1}$,
wherein
$R^{4.1}$ denotes hydrogen or $C_{1-4}$-alkyl,
$R^{4.2}$ denotes hydrogen or $C_{1-4}$-alkyl,
$R^{4.3}$ denotes hydrogen or $C_{1-4}$-alkyl,
or
$R^3$ and $R^4$ or $R^{3a}$ and $R^{4a}$ together denote —O—$C_{1-3}$-alkyl-O—;
and the pharmacologically acceptable acid addition salts thereof.

3. The compound of formula (IA) according to claim 2, characterized in that
A denotes a bond, —CH$_2$— or —CH$_2$CH$_2$—,
$R^1$ is selected from the group consisting of
hydrogen, $C_{1-6}$-alkyl, $C_{1-4}$-alkyl-SO$_2$—, $C_{1-4}$-alkyl-NH—CO—, H$_2$N—CO—, H$_2$N—$C_{1-4}$-alkyl-, H$_2$N—$C_{1-4}$-alkyl-CO—, H$_2$N—$C_{1-4}$-alkyl-NH—CO—, Phenyl-CO—, Phenyl-CH$_2$—CO—, Phenyl-CH$_2$—, $C_{1-6}$-alkyl-CO—, $C_{1-6}$-alkyl-O—$C_{1-4}$-alkyl-CO—, (CH$_3$)$_2$N—$C_{1-4}$-alkyl-,(CH$_3$)$_2$N—$C_{1-4}$-alkyl-NH—CO—, (CH$_3$)$_3$N$^+$—$C_{1-4}$-alkyl-NH—CO—,(CH$_3$)$_3$N$^+$—$C_{1-4}$-alkyl-CO—, (CH$_3$)$_3$N$^+$—$C_{2-4}$-alkyl-, (CH$_3$)N$^+$—$C_{1-4}$-alkyl-N(C$_{1-4}$-alkyl)-CO—, H$_2$N—C(NH)—NH—$C_{1-6}$—NH—CO—, $C_{1-6}$-alkyl-O—CO—,$C_{1-6}$-alkyl-O—CO—$C_{1-4}$-alkyl-, $C_{1-6}$-alkyl-O—CO—$C_{1-4}$-alkyl-CO—, $C_{1-6}$-alkyl-O—CO—$C_{1-4}$-alkyl-NH—CO—, $C_{1-6}$-alkyl-O—CO—NH—$C_{1-4}$-alkyl-, $C_{1-6}$-alkyl-O—CO—NH—$C_{1-4}$-alkyl-CO—, $C_{1-6}$-alkyl-O—CO—NH—$C_{1-4}$-alkyl-NH—CO—, HOCO—$C_{1-4}$-alkyl-, HOCO—$C_{1-4}$-alkyl-CO—, HOCO—$C_{1-4}$-alkyl-NH—CO— and H$_2$N—CNH—, H$_2$NC(NH)NH—$C_{1-6}$-alkyl-CO—,
$R^2$ independently from each other are selected from the group consisting of hydrogen, halogen, CN, $C_{1-4}$-alkyl and $C_1$-alkyl-O—,
$R^6$ independently from each other are selected from the group consisting of hydrogen, halogen, CN, $C_{1-4}$-alkyl and $C_1$-alkyl-O—
$R^3$ are selected from the group consisting of hydrogen halogen, CN and $C_{1-4}$-alkyl,
$R^4$ independently from each other are selected from the group consisting of hydrogen halogen, CN, $C_{1-4}$-alkyl, $C_{1-4}$-alkyl-OCO—, —COOR$^{4.1}$ and —CONR$^{4.2}$R$^{4.3}$,
wherein
$R^{4.1}$ denotes hydrogen or $C_{1-4}$-alkyl,
$R^{4.2}$ denotes hydrogen or $C_{1-4}$-alkyl,
$R^{4.3}$ denotes hydrogen or $C_{1-4}$-alkyl,
or
$R^3$ and $R^4$ together denote —O—$C_{1-3}$-alkyl-O—;
and the pharmacologically acceptable acid addition salts thereof.

4. The compound of formula (IC.1) according to claim 2, characterized in that
A denotes a bond, —CH$_2$— or —CH$_2$CH$_2$—,
L denotes a bridging group —CO—NH—$C_{2-6}$-alkyl-NH—CO—,
forming a compound of formula IC or IC.1,
$R^2$, $R^{2a}$ independently from each other are selected from the group consisting of hydrogen, halogen, CN, $C_{1-4}$-alkyl and $C_1$-alkyl-O—,
$R^6$, $R^{6a}$ independently from each other are selected from the group consisting of hydrogen, halogen, CN, $C_{1-4}$-alkyl and $C_1$-alkyl-O—
$R^3$, $R^{3a}$ are selected from the group consisting of hydrogen halogen, CN and $C_{1-4}$-alkyl,
$R^4$, $R^{4a}$ independently from each other are selected from the group consisting of hydrogen halogen, CN, $C_{1-4}$-alkyl, $C_{1-4}$-alkyl-OCO—, —COOR$^{4.1}$ and —CONR$^{4.2}$R$^{4.3}$,
wherein
$R^{4.1}$ denotes hydrogen or $C_{1-4}$-alkyl,
$R^{4.2}$ denotes hydrogen or $C_{1-4}$-alkyl,
$R^{4.3}$ denotes hydrogen or $C_{1-4}$-alkyl,
or
$R^3$ and $R^4$ or $R^{3a}$ and $R^{4a}$ together denote —O—$C_{1-3}$-alkyl-O—;
and the pharmacologically acceptable acid addition salts thereof.

5. The compound of formula (IB) according to claim 2, characterized in that
$R^{1b}$ denotes $C_{1-4}$-alkyl, and
$R^{1s}$ denotes $C_{1-6}$-alkyl,
and the pharmaceutically acceptable acid addition salts thereof.

6. The compound of formula (IC) according to claim 2, characterized in that
L denotes a bridging group —CO—NH—$C_{2-6}$-alkyl-NH—CO—,
forming a compound of formula (IC) or (IC.1),
and the pharmaceutically acceptable acid addition salts thereof.

7. The compound according to claim 2, characterized in that
R², R³, R⁴, R⁶, R⁷ denote hydrogen.
8. The compound according to claim 1, characterized in that
A denotes —CH₂CH₂—, and
E, D denote —CH₂—.
9. The compound according to claim 1, characterized in that the compound is selected from the group consisting of compounds (1) to (12):
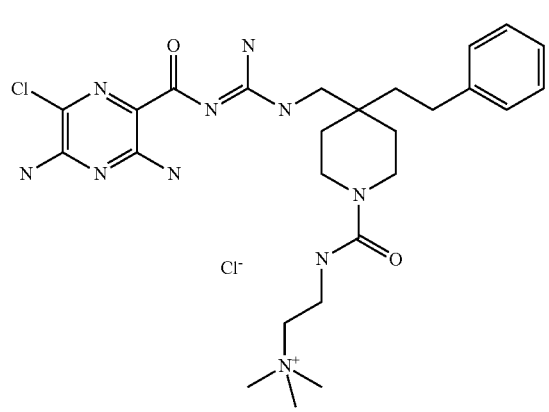
(1)
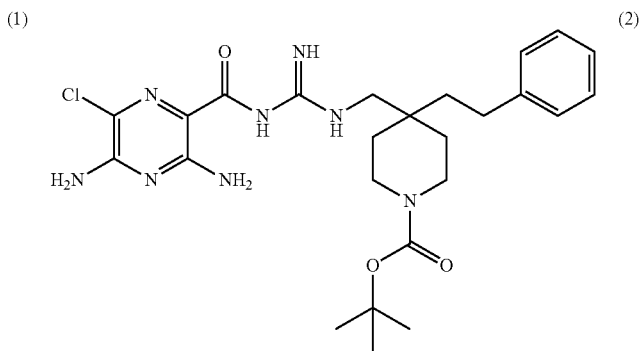
(2)
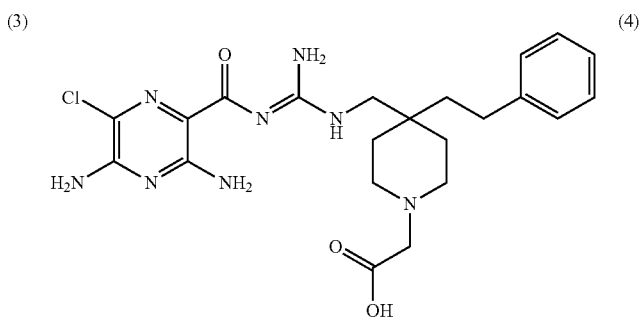
(3)
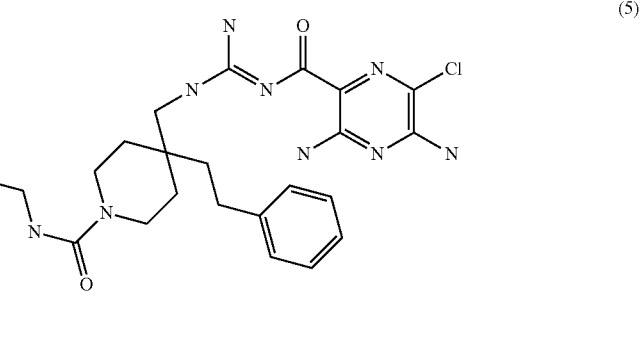
(4)
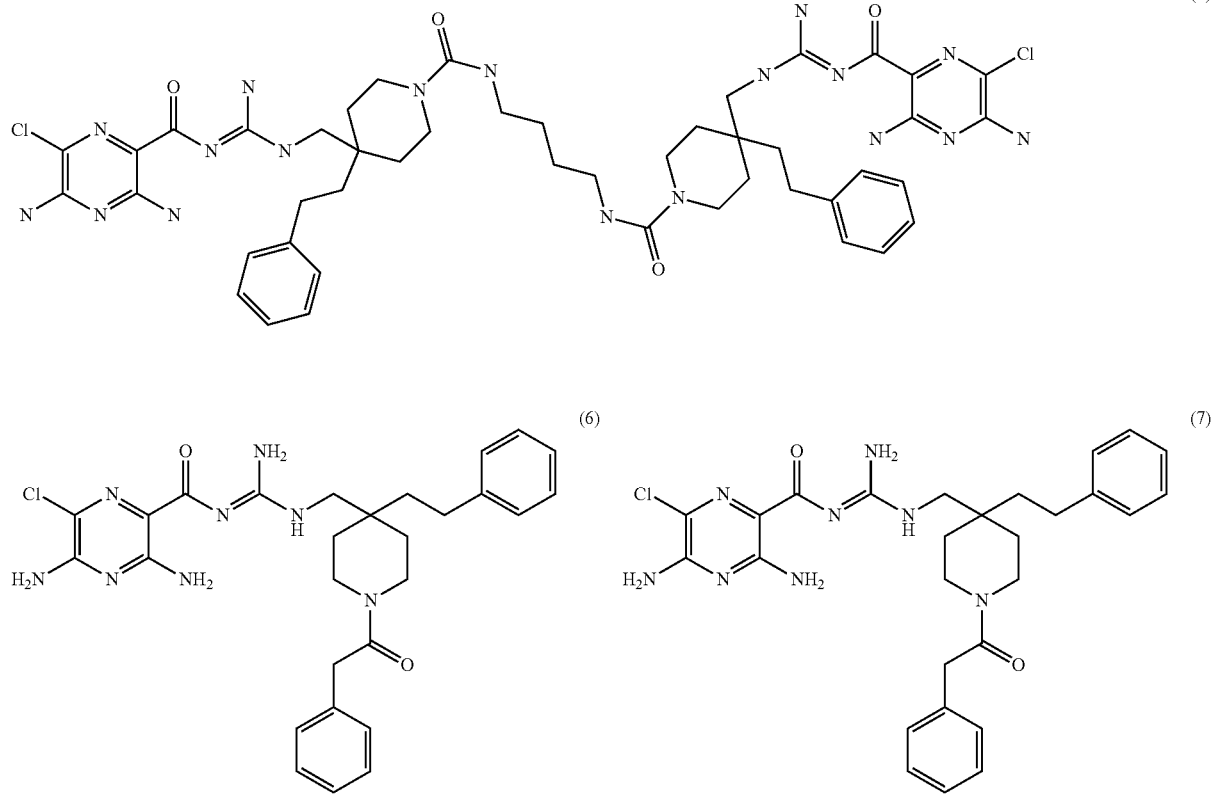
(5)
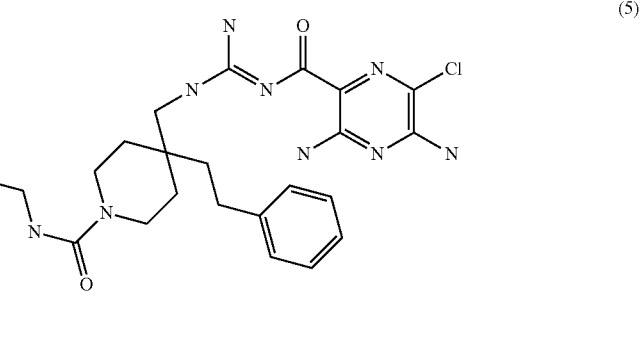
(6)
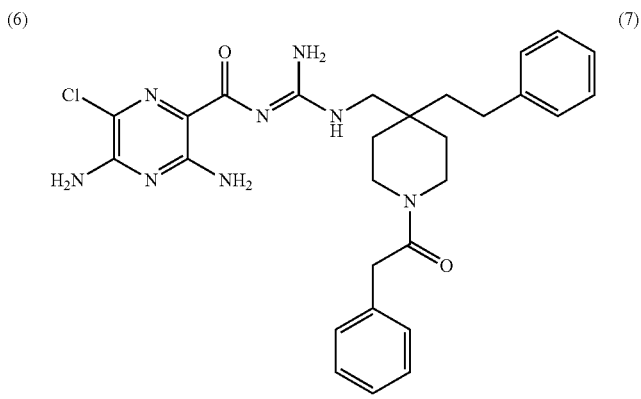
(7)

-continued

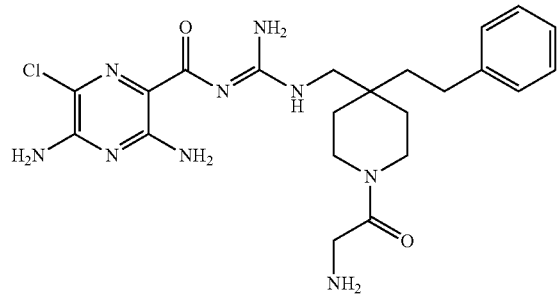
(8)

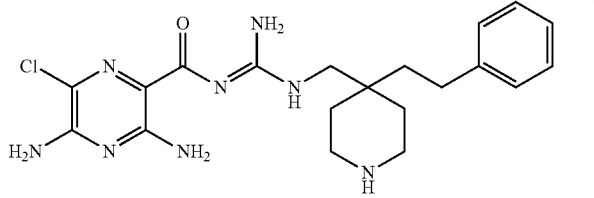
(9)

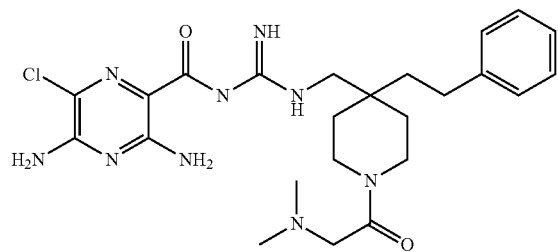
(10)

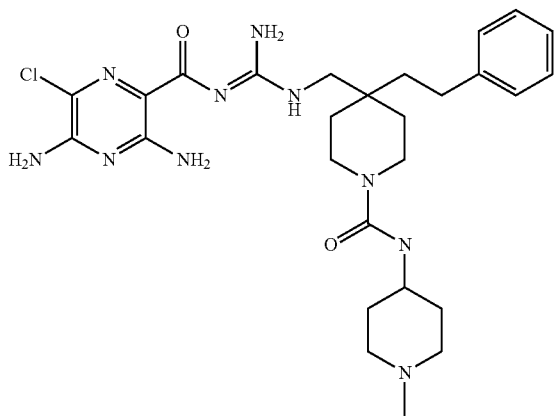
(11)

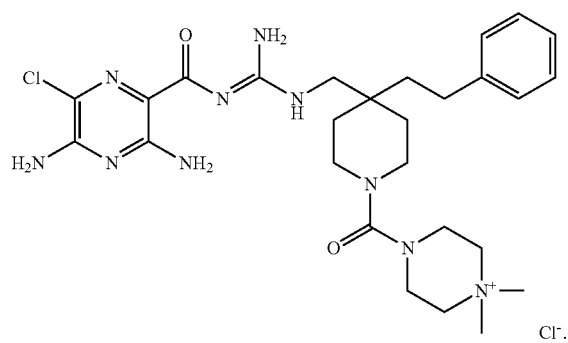
(12)

10. A pharmaceutical composition comprising a compound according to claim 1 or a pharmaceutically acceptable salt thereof and a pharmaceutically acceptable carrier.

11. A pharmaceutical composition according to claim 10, comprising, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

* * * * *

UNITED STATES PATENT AND TRADEMARK OFFICE
CERTIFICATE OF CORRECTION

| | | |
|---|---|---|
| PATENT NO. | : 8,759,349 B2 | Page 1 of 1 |
| APPLICATION NO. | : 13/662791 | |
| DATED | : June 24, 2014 | |
| INVENTOR(S) | : Armin Heckel et al. | |

It is certified that error appears in the above-identified patent and that said Letters Patent is hereby corrected as shown below:

In the claims

In claim 1, column 134, definition of R1, lines 16-19, change the text reading

"$R^1$ is selected from the group consisting of hydrogen, $C_{1-6}$alkyl, optionally substituted piperidinyl-CO-, optionally substituted piperazinyl-CO-, $R^{1.1}$-$SO_2$-,"

to

--$R^1$ is selected from the group consisting of hydrogen, $C_{1-6}$alkyl, optionally substituted piperidinyl-CO-, optionally substituted piperazinyl-CO-, optionally substituted piperidinyl-NH-CO-, $R^{1.1}$-$SO_2$-,--

Signed and Sealed this
Fifteenth Day of March, 2016

Michelle K. Lee
*Director of the United States Patent and Trademark Office*